US010858444B2

(12) United States Patent
Scheinberg et al.

(10) Patent No.: US 10,858,444 B2
(45) Date of Patent: *Dec. 8, 2020

(54) T CELL RECEPTOR-LIKE ANTIBODIES SPECIFIC FOR A WT1 PEPTIDE PRESENTED BY HLA-A2

(71) Applicants: Memorial Sloan Kettering Cancer Center, New York, NY (US); Eureka Therapeutics, Inc., Emeryville, CA (US)

(72) Inventors: David Scheinberg, New York, NY (US); Tao Dao, New York, NY (US); Cheng Liu, Emeryville, CA (US); Su Yan, Emeryville, CA (US)

(73) Assignees: Memorial Sloan Kettering Cancer Center, New York, NY (US); Eureka Therapeutics, Inc., Emeryville, CA (US)

( * ) Notice: Subject to any disclaimer, the term of this patent is extended or adjusted under 35 U.S.C. 154(b) by 73 days.

This patent is subject to a terminal disclaimer.

(21) Appl. No.: 16/055,535

(22) Filed: Aug. 6, 2018

(65) Prior Publication Data
US 2019/0144563 A1 May 16, 2019

Related U.S. Application Data

(63) Continuation of application No. 15/364,953, filed on Nov. 30, 2016, now Pat. No. 10,040,865, which is a continuation of application No. 14/724,155, filed on May 28, 2015, now Pat. No. 9,540,448, which is a continuation of application No. 14/008,447, filed as application No. PCT/US2012/031892 on Apr. 2, 2012, now Pat. No. 9,074,000.

(60) Provisional application No. 61/470,635, filed on Apr. 1, 2011, provisional application No. 61/491,392, filed on May 31, 2011.

(51) Int. Cl.
| A61K 39/00 | (2006.01) |
| C07K 16/32 | (2006.01) |
| A61K 47/68 | (2017.01) |
| C07K 16/28 | (2006.01) |
| C07K 16/18 | (2006.01) |
| G01N 33/574 | (2006.01) |

(52) U.S. Cl.
CPC .......... *C07K 16/32* (2013.01); *A61K 47/6849* (2017.08); *A61K 47/6851* (2017.08); *C07K 16/18* (2013.01); *C07K 16/2809* (2013.01); *C07K 16/2833* (2013.01); *G01N 33/5748* (2013.01); *A61K 2039/505* (2013.01); *C07K 2317/21* (2013.01); *C07K 2317/31* (2013.01); *C07K 2317/34* (2013.01); *C07K 2317/56* (2013.01); *C07K 2317/565* (2013.01); *C07K 2317/567* (2013.01); *C07K 2317/622* (2013.01); *C07K 2317/732* (2013.01)

(58) Field of Classification Search
CPC ..................................................... C07K 16/32
See application file for complete search history.

(56) References Cited

U.S. PATENT DOCUMENTS

| 6,225,051 B1 | 5/2001 | Sugiyama et al. |
| 9,074,000 B2 | 7/2015 | Scheinberg et al. |
| 9,540,448 B2 | 1/2017 | Scheinberg et al. |
| 10,239,952 B2 * | 3/2019 | Scheinberg ............ C07K 16/32 |

FOREIGN PATENT DOCUMENTS

| WO | WO-00/18795 A2 | 4/2000 |
| WO | WO-03/068201 A2 | 8/2003 |
| WO | WO-03/070752 A2 | 8/2003 |
| WO | WO-2005/056595 A2 | 6/2005 |
| WO | WO-2009/108372 A2 | 9/2009 |

OTHER PUBLICATIONS

Denkberg G et al: "Recombinant antibodies 1-15 with T-cell receptor-like specificity: Novel tools to study MHC class I presentation", Autoimmunity Reviews, Elsevier, Amsterdam, NL, vol. 5, No. 4, Apr. 1, 2006 (Apr. 1, 2006), pp. 252-257, XP024977451, ISSN: 1568-9972, DOI: 10.1016/J.AUTREV.2005.07.004 [retrieved on Apr. 1, 2006] *the whole document*.
Oka Y et al: "Development of WT1 Peptide Cancer Vaccine Against Hematopoietic Malignancies and Solid Cancers", Current Medicinal Chemistry, Bentham Science Publishers BV, BE, vol. 13, Jan. 1, 2006 (Jan. 1, 2006), pp. 2345-2352, XP007906253, ISSN: 0929-8673, DOI: 10.2174/092986706777935104 *the whole document*.
Ralph Willemsen et al: "Selection of human antibody fragments directed against tumor T-cell epitopes for adoptive T-cell therapy", Cytometry Part A, vol. 73A, No. 11, Nov. 1, 2008 (Nov. 1, 2008), pp. 1093-1099, XP055028814, ISSN: 1552-4922, DOI: 10.1002/cyto.a.20644 *the whole document*.

(Continued)

Primary Examiner — Sheela J. Huff
(74) Attorney, Agent, or Firm — Foley & Lardner LLP

(57) ABSTRACT

The present invention provides antigen binding proteins that specifically bind to Wilms' tumor protein (WT1), including humanized, chimeric and fully human antibodies against WT1, antibody fragments, chimeric antigen receptors (CARs), fusion proteins, and conjugates thereof. The antigen binding proteins and antibodies bind to HLA-A0201-restricted WT1 peptide. Such antibodies, fragments, fusion proteins and conjugates thereof are useful for the treatment of WT1 associated cancers, including for example, breast cancer, ovarian cancer, prostate cancer, chronic myelocytic leukemia, multiple myeloma, acute lymphoblastic leukemia (ALL), acute myeloid/myelogenous leukemia (AML) and myelodysplastic syndrome (MDS). In more particular embodiments, the anti-WT1/A antibodies may comprise one or more framework region amino acid substitutions designed to improve protein stability, antibody binding and/or expression levels.

10 Claims, 34 Drawing Sheets
Specification includes a Sequence Listing.

(56) References Cited

OTHER PUBLICATIONS

U, Keilholz et al: "A clinical and immunologic phase 2 trial of Wilms tumor gene product 1 (WT1) peptide vaccination in patients with AML and MDS", Blood, vol. 113, No. 26, Jun. 25, 2009 (Jun. 25, 2009), pp. 6541-6548, XP055045499, ISSN: 0006-4971, DOI: 10.1182/blood-2009-02-202598 *abstract* *p. 6541, left-hand column, paragraph 2—p. 6542, left-hand column, paragraph 2*.
International Search Report and Written Opinion, PCT/US2012/031892, Memorial Sloan Kettering Cancer Center (dated Dec. 18, 2012).

\* cited by examiner

```
  1 mgsdvrdlna llpavpslgg gggcalpvsg aaqwapvldf appgasaygs lggpapppap
 61 pppppppphs fikqepswgg aepheeqcls aftvhfsgqf tgtagacryg pfgppppsqa
121 ssgqarmfpn apylpscles qpairnqgys tvtfdgtpsy ghtpshhaaq fpnhsfkhed
181 pmgqqgslge qqysvpppvy gchtptdsct gsqalllrtp yssdnlyqmt sqlecmtwnq
241 mnlgatlkgv aagssssvkw tegqsnhstg yesdnhttpi lcgaqyriht hgvfrgiqdv
301 rrvpgvaptl vrsasetsek rpfmcaypgc nkryfklshl qmhsrkhtge kpyqcdfkdc
361 errfsrsdql krhqrrhtgv kpfqcktcqr kfsrsdhlkt htrthtgkts ekpfscrwps
421 cqkkfarsde lvrhhnmhqr nmtklqlal (SEQ ID NO: 118)
```

Figure 1

Flow cytometric titration of mAb #13 on T2 cells pulsed w/ WT1 peptide

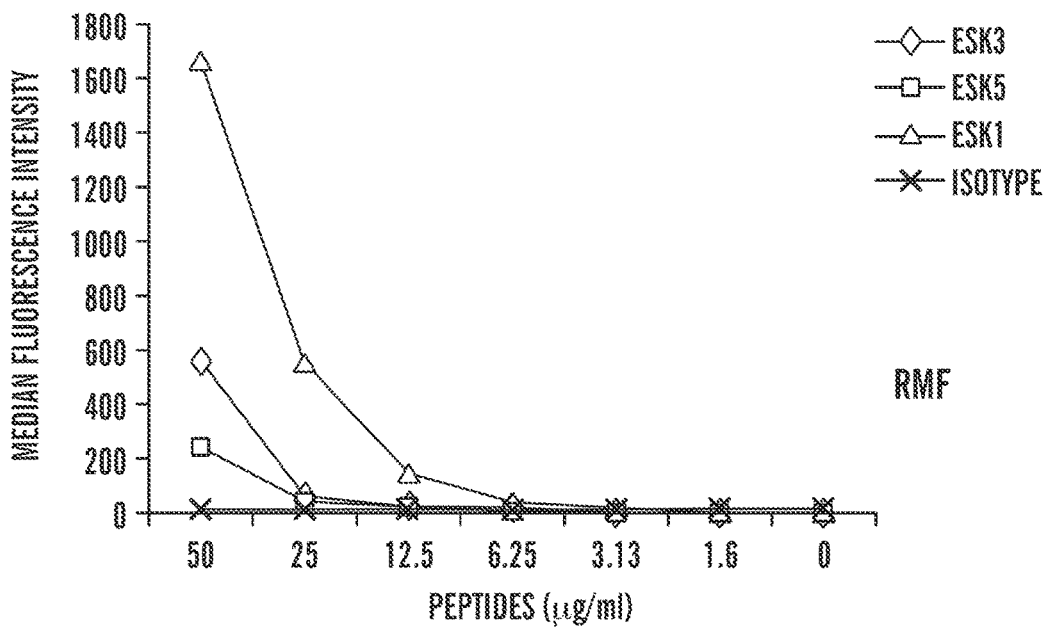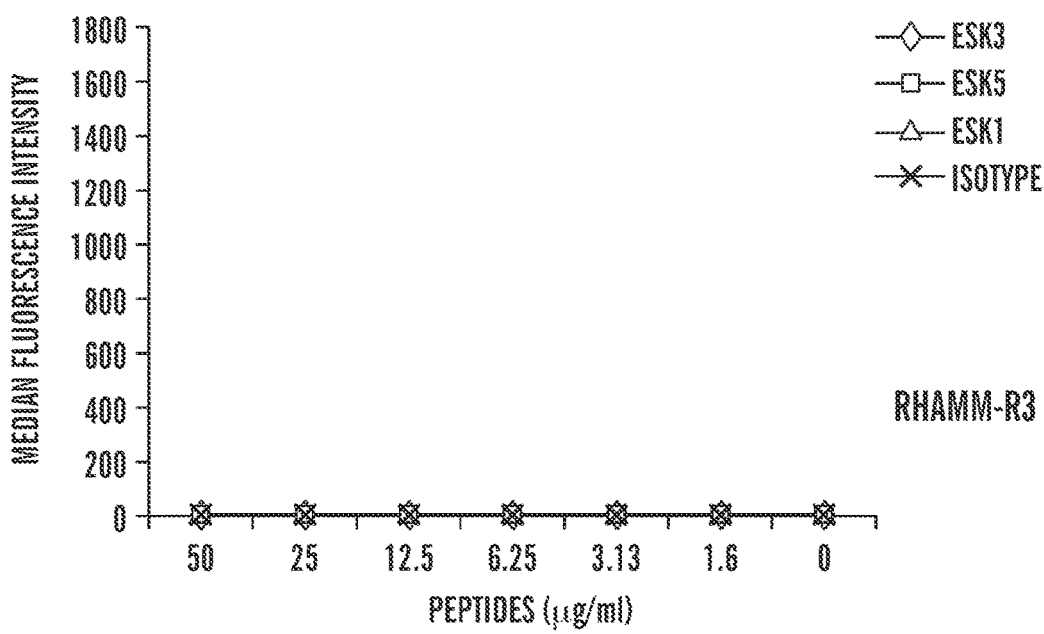
*Figure 6*

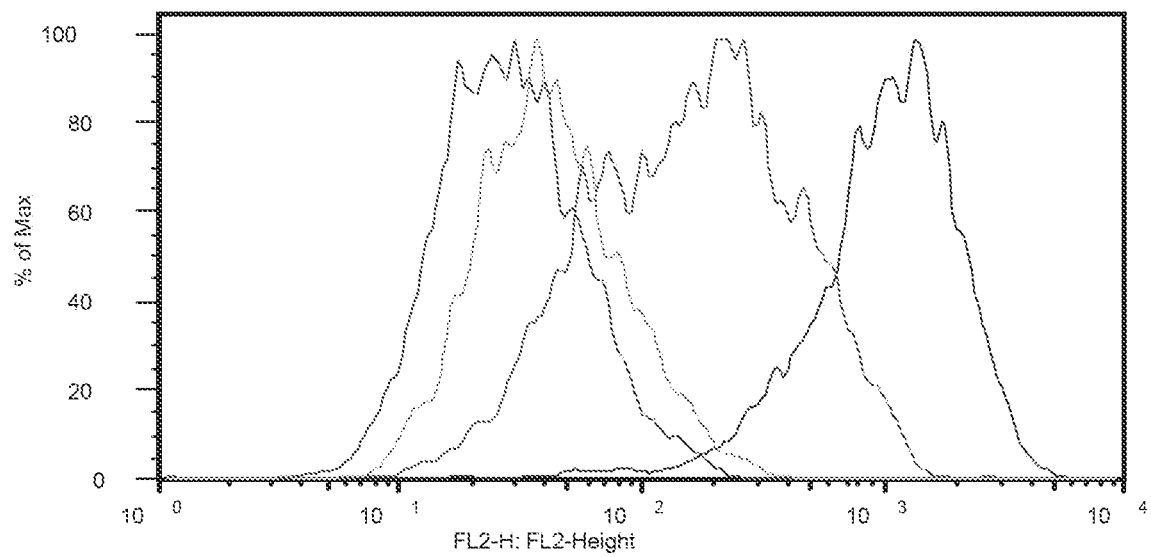
50 ug/ml
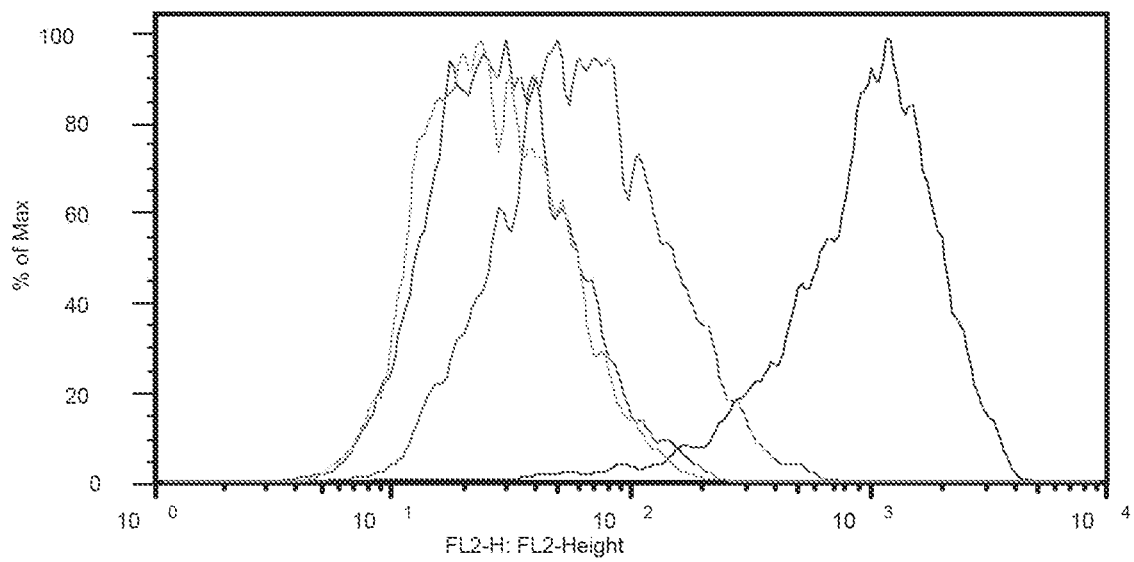
25 ug/ml
Figure 14

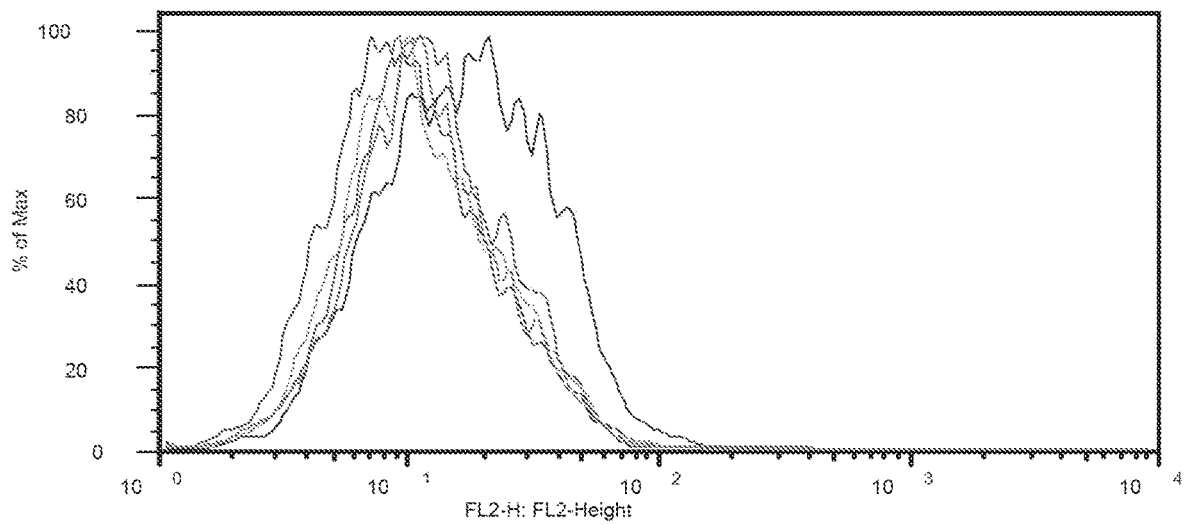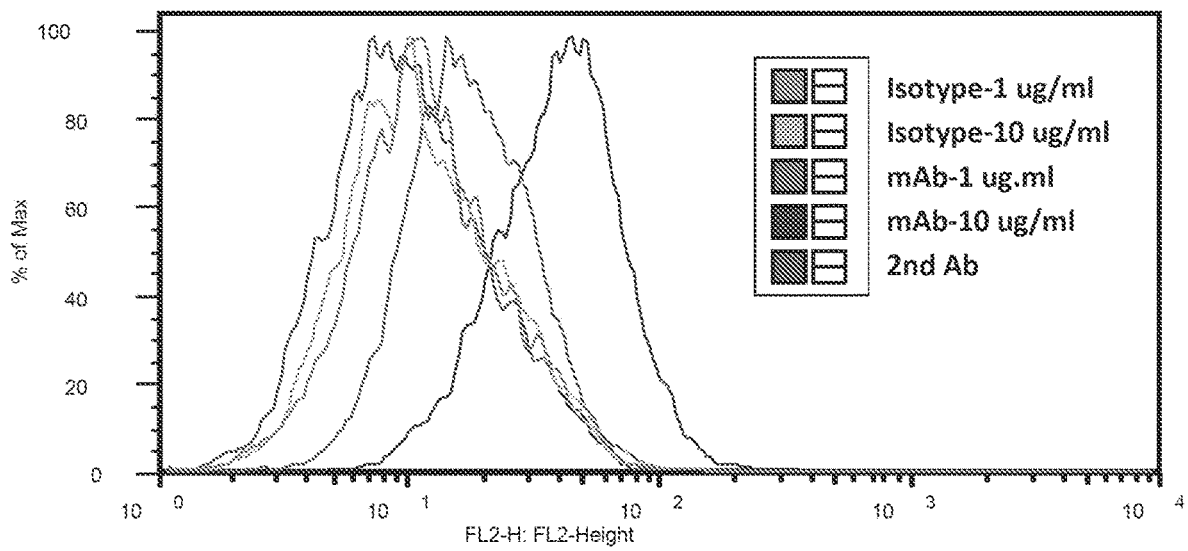
Figure 16

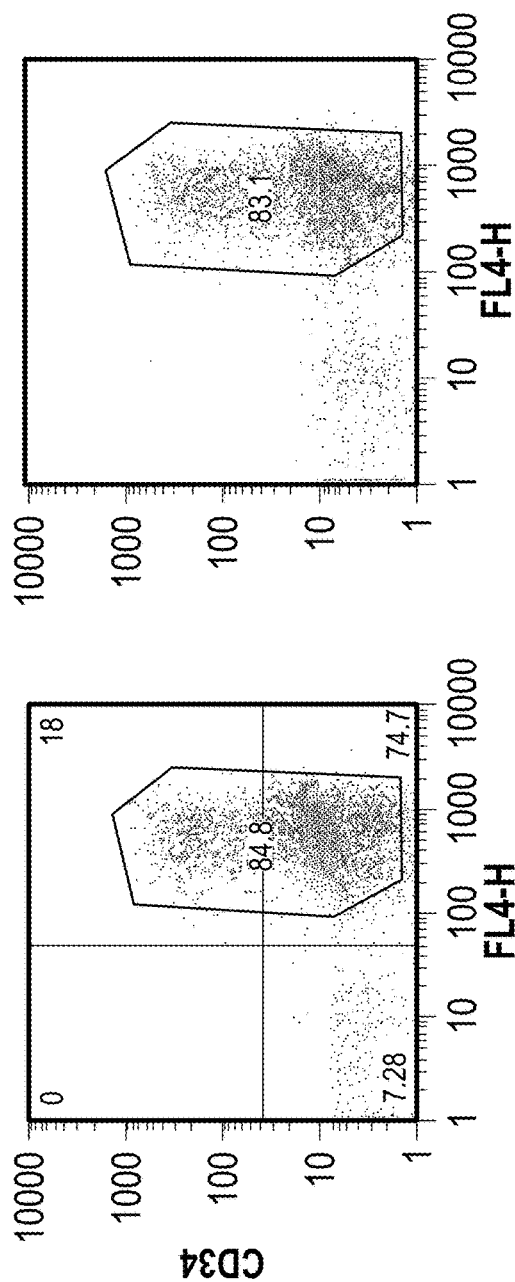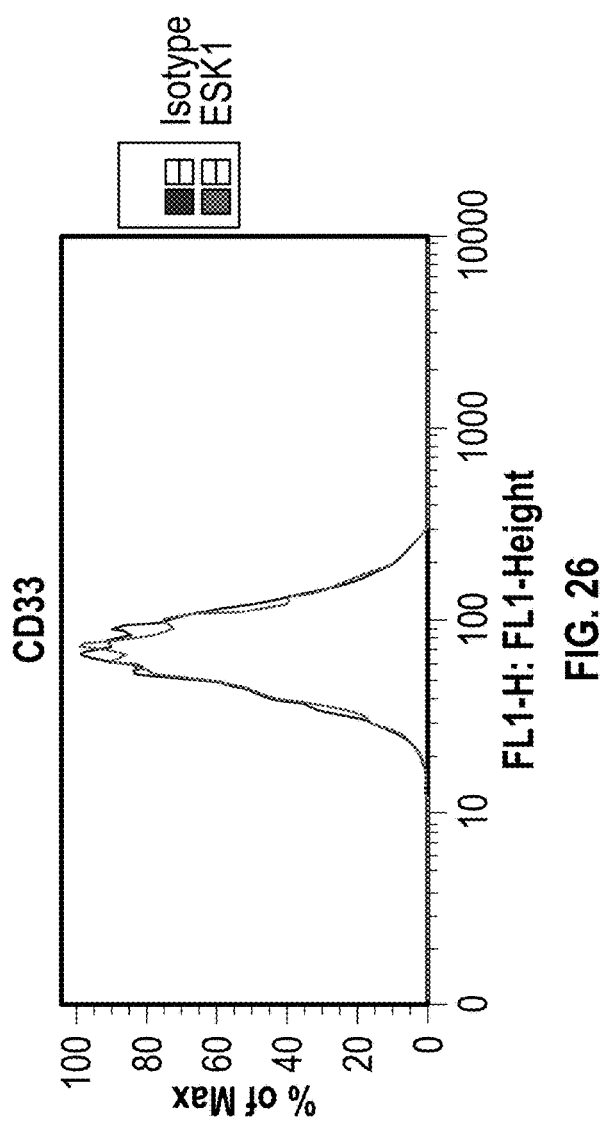
FIG. 26

|  | HEK297-mAbs | CHO-mAbs | Cho-MAGE |
|---|---|---|---|
| No mAb | 1 | 1 | 1 |
| #13-10ug/ml | 1 | 13 | 11 |
| #13-3ug/m | 8 | 8 | 15 |
| #13-1ug/m | 3 | 2 | 12 |
| #13-0.3ug/ml | 0 |  | 14 |
| #13-0.1ug/m | 3 |  | 5 |
| #13-0.03ug/m | 0 |  | 0 |
| hIgG1-10ug/ml |  | 0 | 0 |
| hIgG1-3ug/ml |  | 0 | 0 |
| hIgG1-1ug/ml |  | 0 | 0 |
| hIgG1-0.3ug/ml |  |  | 0 |
| hIgG1-0.1ug/ml |  |  | 2 |
| hIgG1-0.03ug/ml |  |  | 0 |

T CELL RECEPTOR-LIKE ANTIBODIES SPECIFIC FOR A WT1 PEPTIDE PRESENTED BY HLA-A2

CROSS-REFERENCE TO RELATED APPLICATIONS

This application is a continuation of U.S. Patent application Ser. No. 15/364,953, filed Nov. 30, 2016, which is a continuation of U.S. Patent application Ser. No. 14/724,155, filed May 28, 2015, which is a continuation of U.S. Patent application Ser. No. 14/008,447, filed Dec. 10, 2013, which is a National Phase filing under 35 U.S.C. § 371 of PCT International Application No. PCT/US2012/31892, filed Apr. 2, 2012, which claims the benefit of and priority to U.S. Provisional Application No. 61/470,635, filed Apr. 1, 2011, and U.S. Provisional Application No. 61/491,392 filed May 31, 2011, all of which are hereby incorporated by reference in their entireties.

STATEMENT OF RIGHTS UNDER FEDERALLY-SPONSORED RESEARCH

This invention was made with government support under grants CA023766 and CA055349 awarded by the National Institutes of Health. The government has certain rights in the invention.

SEQUENCE LISTING

This application contains a Sequence Listing, created on Nov. 13, 2018; the file, in ASCII format, is named 115872-0392_Seqlisting.txt, and is 80 KB in size. The file is hereby incorporated by reference in its entirety into the application.

TECHNICAL FIELD

The present invention relates generally to antibodies against cytosolic proteins. More particularly, the invention relates to antibodies against Wilm's tumor oncogene protein (WT1), specifically antibodies that recognize a WT1 peptide in conjunction with a major histocompatability antigen.

BACKGROUND OF THE INVENTION

The Wilms' tumor oncogene protein (WT1) is an attractive target for immunotherapy for most leukemias and a wide range of cancers. WT1 is a zinc finger transcription factor that is normally expressed in mesodermal tissues during embryogenesis. In normal adult tissue, WT1 expression is limited to low levels in $CD34^+$ hematopoietic stem cells but is over-expressed in leukemias of multiple lineages and a wide range of solid tumors (1-2). More recently, WT1 expression has been reported to be a marker of minimal residual disease. Increasing transcript levels in patients with acute myeloid leukemia (AML) in morphologic remission have been predictive of overt clinical relapse (3, 4). Furthermore, antibodies to WT1 are detected in patients with hematopoietic malignancies and solid tumors, indicating that WT1 is a highly immunogenic antigen (7).

For the most part, clinically approved therapeutic monoclonal antibodies (mAbs) recognize structures of cell surface proteins. WT1, however, is a nuclear protein and, therefore, is inaccessible to classical antibody therapy. Up until now, immunotherapy targeting WT1 has been limited to cellular approaches, exclusively aimed at generating WT1-specific cytotoxic CD8 T cell (CTL) responses that recognize peptides presented on the cell surface by MHC class I molecules.

For induction of CTL responses, intracellular proteins are usually degraded by the proteasome or endo/lysosomes, and the resulting peptide fragments bind to MHC class I or II molecules. These peptide-MHC complexes are displayed at the cell surface where they provide targets for T cell recognition via a peptide-MHC (pMHC)-T cell receptor (TCR) interaction (8, 9). Vaccinations with peptides derived from the WT1 protein induce HLA-restricted cytotoxic CD8 T cells, which are capable of killing tumor cells.

To improve efficacy, cancer antigens can be targeted with monoclonal antibody therapy. Monoclonal antibody (mAb) therapy has been shown to exert powerful antitumor effects by multiple mechanisms, including complement-dependent cytotoxicity (CDC), antibody-dependent cellular cytotoxicity (ADCC) and direct cell inhibition or apoptosis-inducing effects on tumor cells that over-express the target molecules. Furthermore, mAb can be used as carriers to specifically deliver a cytotoxic moiety such as a radionuclide, cytotoxic drug or toxin to the tumor cells (18).

A tremendous benefit would exist if, in addition to a cellular immunotherapy approach, a humoral immunotherapy approach was available to target non-cell surface tumor antigens. Therefore, a monoclonal antibody (mAb) that mimics a T cell receptor in that it is specific for a target comprising a fragment of an intracellular protein in conjunction with an MHC molecule, for example, a WT1 peptide/HLA-A2 complex, would be a novel and effective therapeutic agent alone or as a vehicle capable of delivering potent anti-cancer reagents, such as drugs, toxins and radioactive elements. Such mAbs would also be useful as diagnostic or prognostic tools.

SUMMARY OF THE INVENTION

The present disclosure identifies and characterizes antigen-binding proteins, such as antibodies, that are able to target cytosolic/intracellular proteins, for example, the WT1 oncoprotein. The disclosed antibodies target a peptide/MHC complex as it would typically appear on the surface of a cell following antigen processing of WT1 protein and presentation by the cell. In that regard, the antibodies mimic T-cell receptors in that the antibodies have the ability to specifically recognize and bind to a peptide in an MHC-restricted fashion, that is, when the peptide is bound to an MHC antigen. The peptide/MHC complex recapitulates the antigen as it would typically appear on the surface of a cell following antigen processing and presentation of the WT1 protein to a T-cell.

The antibodies disclosed specifically recognize and bind to epitopes of a peptide/HLA-A2 complex, particularly a WT1/HLA-A0201 complex. Examples of peptides that are recognized by the antigen-binding proteins of the invention as part of an HLA-peptide complex include, but are not limited to, those shown in Table 7, for example, a peptide with the amino acid sequence RMFPNAPYL (SEQ ID NO: 1.)

In one aspect, therefore, the invention relates to an isolated antibody, or antigen-binding fragment thereof, that binds to a peptide with the amino acid sequence, RMFP-NAPYL, when said peptide is bound to an MHC antigen, such as HLA-A2.

In another aspect, the invention relates to an isolated antigen-binding protein, antibody, or antigen-binding fragment thereof, comprising (A) (i) a heavy chain (HC) variable region comprising HC-CDR1, HC-CDR2 and HC-CDR3 respectively, comprising amino acid sequences SEQ ID NOS: 2, 3, and 4; and a light chain (LC) variable region comprising LC-CDR1, LC-CDR2 and LC-CDR3 respectively, comprising amino acid sequences SEQ ID NOS: 8, 9 and 10; (ii) a heavy chain (HC) variable region comprising HC-CDR1, HC-CDR2 and HC-CDR3 respectively, comprising amino acid sequences SEQ ID NOS: 20, 21 and 22; and a light chain (LC) variable region comprising LC-CDR1, LC-CDR2 and LC-CDR3 respectively, comprising amino acid sequences SEQ ID NOS: 26, 27 and 28; (iii) a heavy chain (HC) variable region comprising HC-CDR1, HC-CDR2 and HC-CDR3 respectively, comprising amino acid sequences SEQ ID NOS: 38, 39 and 40; and a light chain (LC) variable region comprising LC-CDR1, LC-CDR2 and LC-CDR3 respectively, comprising amino acid sequences selected from SEQ ID NOS: 44, 45 and 46; (iv) a heavy chain (HC) variable region comprising HC-CDR1, HC-CDR2 and HC-CDR3 respectively, comprising amino acid sequences SEQ ID NOS: 56, 57 and 58; and a light chain (LC) variable region comprising LC-CDR1, LC-CDR2 and LC-CDR3 respectively, comprising amino acid sequences SEQ ID NOS: 62, 63 and 64; (v) a heavy chain (HC) variable region comprising HC-CDR1, HC-CDR2 and HC-CDR3 respectively, comprising amino acid sequences SEQ ID NOS: 74, 75 and 76; and a light chain (LC) variable region comprising LC-CDR1, LC-CDR2 and LC-CDR3 respectively, comprising amino acid sequences SEQ ID NOS: 80, 81 and 82; or (vi) a heavy chain (HC) variable region comprising HC-CDR1, HC-CDR2 and HC-CDR3 respectively, comprising amino acid sequences SEQ ID NOS: 92, 93 and 94; and a light chain (LC) variable region comprising LC-CDR1, LC-CDR2 and LC-CDR3 respectively, comprising amino acid sequences SEQ ID NOS: 98, 99 and 100.

In another aspect, the invention relates to an isolated antigen-binding protein, antibody, or antigen-binding fragment thereof, comprising a $V_H$ and $V_L$ comprising first and second amino acid sequences, respectively, selected from SEQ ID NOS: 14 and 16; 32 and 34; 50 and 52; 68 and 70; 86 and 88; and 104 and 106.

In yet another aspect, the invention relates to an isolated antigen-binding protein, antibody, or antigen-binding fragment thereof, comprising an amino acid sequence selected from SEQ ID NOS: 18, 36, 54, 72, 90, and 108.

In a related aspect, the isolated antigen-binding protein comprises an antigen-binding region as disclosed in any of Tables 1-8. The antigen-binding protein may be a fusion protein.

In another aspect, the invention relates to an immunoconjugate comprising a first component which is an antigen-binding protein, antibody or antigen-binding fragment thereof as disclosed herein. The immunoconjugate comprises a second component that is a cytotoxin, a detectable label, a radioisotope, a therapeutic agent, a binding protein or a molecule having a second amino acid sequence. Where the second component is a binding protein or second antibody, the binding protein or second antibody has binding specificity for a target that is different from the HLA-peptide complex for which the first is specific.

In a related aspect, therefore, the present invention relates to bispecific antibody comprising an antigen-binding protein or functional fragment thereof as described herein.

In yet another aspect, the invention relates to nucleic acids that encode antigen binding proteins, including antibodies and chimeric antigen receptors specific for a WT1 peptide/HLA complex, in particular the complex of WT1 peptide RMFPNAPYL/HLA-A0201.

In another related aspect, the invention relates to cells comprising the nucleic acids or antigen binding proteins disclosed herein, including recombinant immune effector cells, such as, T-cells genetically modified to express a chimeric antigen receptor comprising an antigen binding region in accordance with the present disclosure. Cells which have been engineered to produce antibodies in accordance with the disclosure are also encompassed by the invention.

In a related aspect, the invention relates to vectors comprising the nucleic acids to encode the antigen binding proteins disclosed herein, including vectors to facilitate expression and/or secretion of an antigen binding protein such as an antibody or chimeric antigen receptor in accordance with the present disclosure.

In a related aspect, the invention relates to pharmaceutical compositions comprising the antigen binding proteins, antibodies, nucleic acids, vectors or cells comprising the nucleic acids or antigen binding proteins disclosed herein, together with a pharmaceutically acceptable carrier.

In another aspect, the invention relates to a method for detecting WT1 on the surface of cells or tissues using WT1 antibodies of the invention.

In yet another aspect, the invention relates to methods for treatment of a subject having a WT1-positive disease, comprising administering to the subject a therapeutically effective amount of an antigen binding protein, antibody or antigen binding fragment thereof, nucleic acid encoding the antigen binding protein or antibody or a cell comprising the nucleic acids or proteins as disclosed herein. The WT1-positive disease is a chronic leukemia, acute leukemia or WT1$^+$ cancer selected from the group consisting of chronic myelocytic leukemia, multiple myeloma (MM), acute lymphoblastic leukemia (ALL), acute myeloid/myelogenous leukemia (AML), myelodysplastic syndrome (MDS), mesothelioma, ovarian cancer, gastrointestinal cancers, breast cancer, prostate cancer and glioblastoma. In some embodiments, the antigen binding protein or antibody is a conjugate thereof having a cytotoxic moiety linked thereto.

BRIEF DESCRIPTION OF THE DRAWINGS

FIG. 1 shows the amino acid sequence of Wilms tumor protein, (GenBank Accession No. P19544) with some HLA-restricted peptides bolded. The 121-140 peptide further encompasses a 9-mer (underlined), RMFPNAPYL (SEQ ID NO: 1), which, in addition to analogs thereof, has been shown to induce WT1-specific cytotoxic T-cell activity.

FIG. 6 shows the dependence on density of RMF/HLA-A0201 complex recognized by WT1 antibody on T2 cells pulsed with RMF (upper panel) or control, RHAMM-R3 (lower panel).

FIG. 14 shows the binding specificity of one embodiment, mAb 15, at different concentrations (50 µg/ml upper; 25 µg/ml lower) of peptide (R3, WT1-A1, WT1-A or no peptide).

FIG. 16 shows binding of mAbs 5 and 15 to U266, a myeloma cell line.

FIG. 26 shows the results of flow cytometric analyses gated on CD33 and CD34 double positive AML blast cells from an HLA-A2 negative patient. WT1 mAb ESK1 did not bind to the blasts.

DETAILED DESCRIPTION OF THE INVENTION

Figure 2:
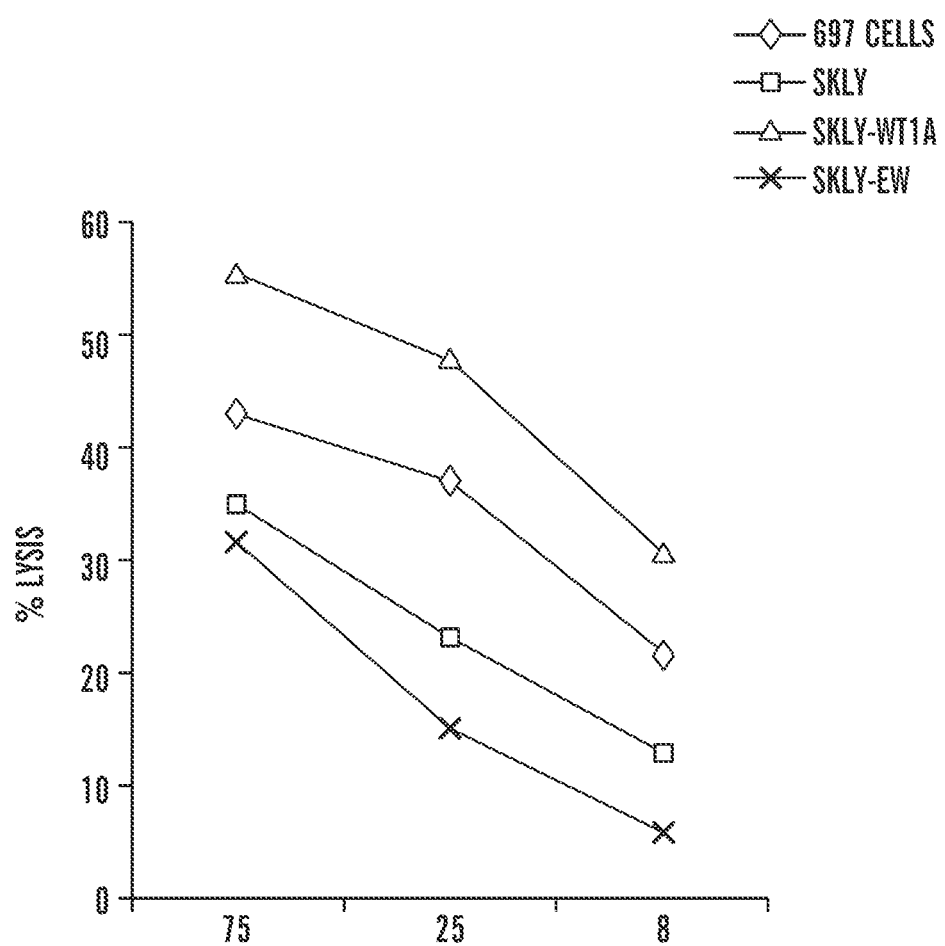
FIG. 2 is a graph showing that vaccination with WT1 peptides induces cytotoxic T cells against WT1$^+$ leukemia cells.

All publications, patents and other references cited herein are incorporated by reference in their entirety into the present disclosure.

In practicing the present invention, many conventional techniques in molecular biology, microbiology, cell biology, biochemistry, and immunology are used, which are within the skill of the art. These techniques are described in greater detail in, for example, Molecular Cloning: a Laboratory Manual 3rd edition, J. F. Sambrook and D. W. Russell, ed. Cold Spring Harbor Laboratory Press 2001; Recombinant Antibodies for Immunotherapy, Melvyn Little, ed. Cambridge University Press 2009; "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., ed., 1994); "A Practical Guide to Molecular Cloning" (Perbal Bernard V., 1988); "Phage Display: A Laboratory Manual" (Barbas et al., 2001). The contents of these references and other references containing standard protocols, widely known to and relied upon by those of skill in the art, including manufacturers' instructions are hereby incorporated by reference as part of the present disclosure. The following abbreviations are used throughout the application:

Ab: Antibody
ADCC: Antibody-dependent cellular cytotoxicity
ALL: Acute lymphocytic leukemia
AML: Acute myeloid leukemia
APC: Antigen presenting cell
β2M: Beta-2-microglobulin
BiTE: Bi-specific T cell engaging antibody
CAR: Chimeric antigen receptor
CDC: Complement dependent cytotoxicity
CMC: Complement mediated cytotoxicity
CDR: Complementarity determining region (see also HVR below)
$C_L$: Constant domain of the light chain
$CH_1$: $1^{st}$ constant domain of the heavy chain $CH_{1,2,3}$: 1st, 2nd and 3rd constant domains of the heavy chain
$CH_{2,3}$: 2nd and 3rd constant domains of the heavy chain
CHO: Chinese hamster ovary
CTL: Cytotoxic T cell
E:T Ratio: Effector:Target ratio
Fab: Antibody binding fragment
FACS: Flow assisted cytometric cell sorting
FBS: Fetal bovine serum
FR: Framework region
HC: Heavy chain
HLA: Human leukocyte antigen
HVR-H: Hypervariable region-heavy chain (see also CDR)
HVR-L: Hypervariable region-light chain (see also CDR)
Ig: Immunoglobulin
IRES: Internal ribosome entry site
$K_D$: Dissociation constant
$k_{off}$: Dissociation rate
$k_{on}$: Association rate
MHC: Major histocompatibility complex
MM: Multiple myeloma
scFv: Single-chain variable fragment
TCR: T cell receptor
$V_H$: Variable heavy chain includes heavy chain hypervariable region and heavy chain variable framework region
$V_L$: Variable light chain includes light chain hypervariable region and light chain variable framework region
WT1: Wilms tumor protein 1

In the description that follows, certain conventions will be followed as regards the usage of terminology. Generally, terms used herein are intended to be interpreted consistently with the meaning of those terms as they are known to those of skill in the art.

An "antigen-binding protein" is a protein or polypeptide that comprises an antigen-binding region or antigen-binding portion, that is, has a strong affinity to another molecule to which it binds. Antigen-binding proteins encompass antibodies, chimeric antigen receptors (CARs) and fusion proteins.

"Antibody" and "antibodies" as those terms are known in the art refer to antigen binding proteins of the immune system. The term "antibody" as referred to herein includes whole, full length antibodies having an antigen-binding region, and any fragment thereof in which the "antigen-binding portion" or "antigen-binding region" is retained, or single chains, for example, single chain variable fragment (scFv), thereof. A naturally occurring "antibody" is a glycoprotein comprising at least two heavy (H) chains and two light (L) chains inter-connected by disulfide bonds. Each heavy chain is comprised of a heavy chain variable region (abbreviated herein as $V_H$) and a heavy chain constant (CH) region. The heavy chain constant region is comprised of three domains, CH1, CH2 and CH3. Each light chain is comprised of a light chain variable region (abbreviated herein as $V_L$) and a light chain constant $C_L$ region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen-binding portion" or "antigen-binding region" of an antibody, as used herein, refers to that region or portion of the antibody that binds to the antigen and which confers antigen specificity to the antibody; fragments of antigen-binding proteins, for example, antibodies includes one or more fragments of an antibody that retain the ability to specifically bind to an antigen (e.g., an peptide/HLA complex). It has been shown that the antigen-binding function of an antibody can be performed by fragments of a full-length antibody. Examples of antigen-binding fragments encompassed within the term "antibody fragments" of an antibody include a Fab fragment, a monovalent fragment consisting of the $V_L$, $V_H$, $C_L$ and CH1 domains; a $F(ab)_2$ fragment, a bivalent fragment comprising two Fab fragments linked by a disulfide bridge at the hinge region; a Fd fragment consisting of the $V_H$ and CH1 domains; a Fv fragment consisting of the $V_L$ and $V_H$ domains of a single arm of an antibody; a dAb fragment (Ward et al., 1989 Nature 341:544-546), which consists of a $V_H$ domain; and an isolated complementarity determining region (CDR).

Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules. These are known as single chain Fv (scFv); see e.g., Bird et al., 1988 Science 242:423-426; and Huston et al., 1988 Proc. Natl. Acad. Sci. 85:5879-5883. These antibody fragments are obtained using conventional techniques known to those of skill in the art, and the fragments are screened for utility in the same manner as are intact antibodies.

An "isolated antibody" or "isolated antigen-binding protein" is one which has been identified and separated and/or recovered from a component of its natural environment. "Synthetic antibodies" or "recombinant antibodies" are generally generated using recombinant technology or using peptide synthetic techniques known to those of skill in the art.

Traditionally, the MHC-peptide complex could only be recognized by a T-cell receptor (TCR), limiting our ability to detect an epitope of interest using T cell-based readout assays. In the present disclosure, antigen binding proteins, including antibodies, having an antigen-binding region based on scFvs that are selected from human scFv phage display libraries using recombinant HLA-peptide complexes are described. These molecules demonstrated exquisite specificity, for example as shown with anti-WT1 antibodies that recognize only HLA-A2-RMFPNAPYL complexes. In addition, along with their inability to bind to HLA-complexes containing other peptides, the molecules were also unable to bind to the peptides themselves, further demonstrating their TCR-like specificity.

The scFvs of the disclosure selected by phage display were initially tested for their ability to bind to peptide presented on the surface of HLA-positive cells. After T2 cells were incubated in the presence of peptide, fluorescently labeled antibodies could be used to selectively recognize the antigen pulsed cells using flow cytometry.

In some embodiments, the invention includes antibodies that have the scFv sequence fused to one or more constant domains of the heavy to form an antibody with an Fc region of a human immunoglobulin to yield a bivalent protein, increasing the overall avidity and stability of the antibody. In addition, the Fc portion allows the direct conjugation of other molecules, including but not limited to fluorescent dyes, cytotoxins, radioisotopes etc. to the antibody for example, for use in antigen quantitation studies, to immobilize the antibody for affinity measurements, for targeted delivery of a therapeutic agent, to test for Fc-mediated cytotoxicity using immune effector cells and many other applications.

The results presented here highlight the specificity, sensitivity and utility of the antibodies of the invention in targeting MHC-peptide complexes.

The molecules of the invention are based on the identification and selection of single chain variable fragments (scFv) using phage display, the amino acid sequence of which confers the molecules' specificity for the MHC restricted peptide of interest and forms the basis of all antigen binding proteins of the disclosure. The scFv, therefore, can be used to design a diverse array of "antibody" molecules, including, for example, full length antibodies, fragments thereof, such as Fab and F(ab')$_2$, minibodies, fusion proteins, including scFv-Fc fusions, multivalent antibodies, that is, antibodies that have more than one specificity for the same antigen or different antigens, for example, bispecific T-cell engaging antibodies (BiTe), tribodies, etc. (see Cuesta et al., *Multivalent antibodies: when design surpasses evolution. Trends in Biotechnology* 28:355-362 2010).

In an embodiment in which the antigen-binding protein is a full length antibody, the heavy and light chains of an antibody of the invention may be full-length (e.g., an antibody can include at least one, and preferably two, complete heavy chains, and at least one, and preferably two, complete light chains) or may include an antigen-binding portion (a Fab, F(ab')$_2$, Fv or a single chain Fv fragment ("scFv")). In other embodiments, the antibody heavy chain constant region is chosen from, e.g., IgG1, IgG2, IgG3, IgG4, IgM, IgA1, IgA2, IgD, and IgE. In some embodiments, the immunoglobulin isotype is selected from IgG1, IgG2, IgG3, and IgG4, more particularly, IgG1 (e.g., human IgG1). The choice of antibody type will depend on the immune effector function that the antibody is designed to elicit.

In constructing a recombinant immunoglobulin, appropriate amino acid sequences for constant regions of various immunoglobulin isotypes and methods for the production of a wide array of antibodies are known to those of skill in the art.

In one embodiment, the antibody or other antigen binding protein is an anti-WT1/HLA-A2 scFv or antigen-binding fragment thereof having an antigen binding region that comprises the amino acid sequence of SEQ ID NO: 18 and specifically binds to a peptide with the amino acid sequence RMFPNAPYL (SEQ ID NO: 1) in conjunction with HLA-A0201. In some embodiments, the anti-WT1 antibody is a scFv-Fc fusion protein or full length human IgG with VH and VL regions or CDRs selected from Table 1.

TABLE 1

| Antigen Peptide | WT1 (Ext002 #3) RMFPNAPYL (SEQ ID NO: 1) | | |
|---|---|---|---|
| CDRs: | 1 | 2 | 3 |
| VH | GGTFSSYAIS (SEQ ID NO: 2) | GIIPIFGTANYAQKFQG (SEQ ID NO: 3) | RIPPYYGMDV (SEQ ID NO: 4) |
| DNA | ggaggcaccttcagcag ctatgctatcagc (SEQ ID NO: 5) | gggatcatccctatctttggtac agcaaactacgcacagaagtt ccagggc (SEQ ID NO: 6) | cggattccccgtactacggtat ggacgtc (SEQ ID NO: 7) |
| VL | SGSSSNIGSNYVY (SEQ ID NO: 8) | RSNQRPS (SEQ ID NO: 9) | AAWDDSLNGVV (SEQ ID NO: 10) |
| DNA | tctggaagcagctccaac atcggaagtaattatgtat ac (SEQ ID NO: 11) | aggagtaatcagcggccctca (SEQ ID NO: 12) | gcagcatgggatgacagcctg aatggtgtggta (SEQ ID NO: 13) |
| Full VH | QVQLVQSGAEVKKPGSSVKVSCKASGGTFSSYAISWVRQAPGQGLE WMGGIIPIFGTANYAQKFQGRVTITADESTSTAYMELSSLRSEDTAVYY CARRIPPYYGMDVWGQGTTVTVSS (SEQ ID NO: 14) | | |
| DNA | caggtgcagctggtgcagtctggggctgaggtgaagaagcctggggtcctcggtgaaggtctcctgc aaggcttctggaggcaccttcagcagctatgctatcagctgggtgcgacaggcccctggacaagg gcttgagtggatgggagggatcatccctatctttggtacagcaaactacgcacagaagttccaggg cagagtcacgattaccgcggacgaatccacgagcacagcctacatggagctgagcagcctgag atctgaggacacggccgtgtattactgtgcgagacggattccccgtactacggtatggacgtctgg ggccaagggaccacggtcaccgtctcctca (SEQ ID NO: 15) | | |
| Full VL | QTVVTQPPSASGTPGQRVTISCSGSSSNIGSNYVYWYQQLPGTAPKL LIYRSNQRPSGVPDRFSGSKSGTSASLAISGPRSVDEADYYCAAWDD SLNGVVFGGGTKLTVLG (SEQ ID NO: 16) | | |
| DNA | cagactgtggtgactcagccaccctcagcgtctgggaccccgggcagagggtcaccatctcttgtt ctggaagcagctccaacatcggaagtaattatgtatactggtaccaacagctcccaggaacggcc cccaaactcctcatctataggagtaatcagcggccctcaggggtccctgaccgattctctggctcca | | |

TABLE 1-continued

```
         agtctggcacctcagcctccctggccatcagtgggccccggtccgtggatgaggctgattattactgt
         gcagcatgggatgacagcctgaatggtgtggtattcggcggagggaccaagctgaccgtcctagg
         t
         (SEQ ID NO: 17)

scFv     QTVVTQPPSASGTPGQRVTISCSGSSSNIGSNYVYWYQQLPGTAPKL
         LIYRSNQRPSGVPDRFSGSKSGTSASLAISGPRSVDEADYYCAAWDD
         SLNGVVFGGGTKLTVLGSRGGGGSGGGGSGGGSLEMAQVQLVQSG
         AEVKKPGSSVKVSCKASGGTFSSYAISWVRQAPGQGLEWMGGIIPIFG
         TANYAQKFQGRVTITADESTSTAYMELSSLRSEDTAVYYCARRIPPYY
         GMDVWGQGTTVTVSS
         (SEQ ID NO: 18)

DNA      cagactgtggtgactcagccaccctcagcgtctgggaccccgggcagagggtcaccatctcttgtt
         ctggaagcagctccaacatcggaagtaattatgtatactggtaccaacagctcccaggaacggcc
         cccaaactcctcatctataggagtaatcagcggccctcaggggtccctgaccgattctctggctcca
         agtctggcacctcagcctccctggccatcagtgggccccggtccgtggatgaggctgattattactgt
         gcagcatgggatgacagcctgaatggtgtggtattcggcggagggaccaagctgaccgtcctagg
         ttctagaggtggtggtggtagcggcggcggcggctctggtggtggatccctcgagatggc
         ccaggtgcagctggtgcagtctggggctgaggtgaagaagcctgggtcctcggtgaaggtctcctg
         caaggcttctggaggcacctTcagcagctatgctatcagctggtgcgacaggcccctggacaag
         ggcttgagtggatgggagggatcatccctatctttggtacagcaaactacgcacagaagttccagg
         gcagagtcacgattaccgcggacgaatccacgagcacagcctacatggagctgagcagcctga
         gatctgaggacacggccgtgtattactgtgcgagacggattccccgtactacggtatggacgtctg
         gggccaagggaccacggtcaccgtctcctca
         (SEQ ID NO: 19)
```

In another embodiment, the antibody or antigen binding protein is an anti-WT1 scFv or antigen-binding fragment thereof that has an antigen binding region that comprises the amino acid sequence of SEQ ID NO: 36 and specifically binds to a peptide with the amino acid sequence RMFP-NAPYL (SEQ ID NO: 1) in conjunction with HLA-A0201. In other embodiments, the anti-WT-1 antibody is a scFv-Fc fusion protein or full length human IgG with VH and VL regions or CDRs selected from Table 2.

TABLE 2

| Antigen Peptide | WT1 (Ext002 #5) RMFPNAPYL (SEQ ID NO: 1) | | |
|---|---|---|---|
| CDRs: | 1 | 2 | 3 |
| VH | GDSVSSNSAAWN (SEQ ID NO: 20) | RTYYGSKWYNDYAVS VKS (SEQ ID NO: 21) | GRLGDAFDI (SEQ ID NO: 22) |
| DNA | ggggacagtgtctctagc aacagtgctgcttggaac (SEQ ID NO: 23) | aggacatactacgggtccaag tggtataatgattatgcagtatct gtgaaaagt (SEQ ID NO: 24) | ggtcgcttaggggatgcttttga tatc (SEQ ID NO: 25) |
| VL | RASQSISSYLN (SEQ ID NO: 26) | AASSLQS (SEQ ID NO: 27) | QQSYSTPLT (SEQ ID NO: 28) |
| DNA | cgggcaagtcagagcatt agcagctatttaaat (SEQ ID NO: 29) | gctgcatccagtttgcaaagt (SEQ ID NO: 30) | caacagagttacagtaccct ctcact (SEQ ID NO: 31) |
| Full VH | QVQLQQSGPGLVKPSQTLSLTCAISGDSVSSNSAAWNWIRQSPSRGL EWLGRTYYGSKWYNDYAVSVKSRITINPDTSKNQFSLQLNSVTPEDTA VYYCARGRLGDAFDIWGQGTMVTVSS (SEQ ID NO: 32) | | |
| DNA | caggtacagctgcagcagtcaggtccaggactggtgaagccctcgcagaccctctcactcacctgt gccatctccggggacagtgtctctagcaacagtgctgcttggaactggatcaggcagtccccatcg agaggccttgagtggctgggaaggacatactacgggtccaagtggtataatgattatgcagtatctg tgaaaagtcgaataaccatcaacccagacacatccaagaaccagttctccctgcagctgaactct gtgactcccgaggacacggctgtgtattactgtgcaagaggtcgcttaggggatgcttttgatatctgg ggccaagggacaatggtcaccgtctcttca (SEQ ID NO: 33) | | |
| Full VL | DIQMTQSPSSLSASVGDRVTITCRASQSISSYLNWYQQKPGKAPKLLIY AASSLQSGVPSRFSGSGSGTDFTLTISSLQPEDFATYYCQQSYSTPLT FGGGTKVDIKR (SEQ ID NO: 34) | | |
| DNA | gacatccagatgacccagtctccatcctccctgtctgcatctgtaggagacagagtcaccatcacttg ccgggcaagtcagagcattagcagctatttaaattggtatcagcagaaaccagggaaagccccta agctcctgatctatgctgcatccagtttgcaaagtggggtcccatcaaggttcagtggcagtggatct | | |

TABLE 2-continued

```
             gggacagatttcactctcaccatcagcagtctgcaacctgaagattttgcaacttactactgtcaaca
             gagttacagtacccctctcactttcggcggagggaccaaagtggatatcaaacgt
             (SEQ ID NO: 35)
``` scFv         DIQMTQSPSSLSASVGDRVTITCRASQSISSYLNWYQQKPGKAPKLLIY
             AASSLQSGVPSRFSGSGSGTDFTLTISSLQPEDFATYYCQQSYSTPLT
             FGGGTKVDIKRSRGGGGSGGGGSGGGGSLEMAQVQLQQSGPGLVK
             PSQTLSLTCAISGDSVSSNSAAWNWIRQSPSRGLEWLGRTYYGSKWY
             NDYAVSVKSRITINPDTSKNQFSLQLNSVTPEDTAVYYCARGRLGDAF
             DIWGQGTMVTVSS
             (SEQ ID NO: 36)

DNA          gacatccagatgacccagtctccatcctccctgtctgcatctgtaggagacagagtcaccatcacttg
             ccgggcaagtcagagcattagcagctatttaaattggtatcagcagaaaccagggaaagccccta
             agctcctgatctatgctgcatccagtttgcaaagtggggtcccatcaaggttcagtggcagtggatct
             gggacagatttcactctcaccatcagcagtctgcaacctgaagattttgcaacttactactgtcaaca
             gagttacagtacccctctcactttcggcggagggaccaaagtggatatcaaacgttctagaggtg
             gtggtggtagcggcggcggcggctctggtggtggtggatccctcgagatggcccaggtac
             agctgcagcagtcaggtccaggactggtgaagccctcgcagaccctctcactcacctgtgccatct
             ccggggacagtgtctctagcaacagtgctgcttggaactggatcaggcagtccccatcgagagc
             cttgagtggctgggaaggacatactacgggtccaagtggtataatgattatgcagtatctgtgaaaa
             gtcgaataaccatcaacccagacacatccaagaaccagttctccctgcagctgaactctgtgactc
             ccgaggacacggctgtgtattactgtgcaagaggtcgcttaggggatgcttttgatatctggggccaa
             gggacaatggtcaccgtctcttca
             (SEQ ID NO: 37)

In another embodiment, the antibody or antigen binding protein is an anti-WT1 scFv or antigen binding fragment thereof that has an antigen binding region that comprises the amino acid sequence of SEQ ID NO: 54 and specifically binds to a peptide with the amino acid sequence RMFP-NAPYL (SEQ ID NO: 1) in conjunction with HLA-A0201. In other embodiments, the anti-WT-1 antibody is a scFv-Fc fusion protein or full length human IgG with VH and VL regions or CDRs selected from Table 3.

TABLE 3

| Antigen Peptide | WT1 (Ext002 #13) RMFPNAPYL (SEQ ID NO: 1) | | |
|---|---|---|---|
| CDRs: | 1 | 2 | 3 |
| VH | GYSFTNFWIS (SEQ ID NO: 38) | RVDPGYSYSTYSPSF QG (SEQ ID NO: 39) | VQYSGYYDWFDP (SEQ ID NO: 40) |
| DNA | ggatacagcttcaccaact tctggatcagc (SEQ ID NO: 41) | agggttgatcctggctactctta tagcacctacagcccgtccttc caaggc (SEQ ID NO: 42) | gtacaatatagtggctactatg actggttcgacccc (SEQ ID NO: 43) |
| VL | SGSSSNIGSNTVN (SEQ ID NO: 44) | SNNQRPS (SEQ ID NO: 45) | AAWDDSLNGWV (SEQ ID NO: 46) |
| DNA | tctggaagcagctccaac atcggaagtaatactgtaa ac (SEQ ID NO: 47) | agtaataatcagcggccctca (SEQ ID NO: 48) | gcagcatgggatgacagcct gaatggttgggtg (SEQ ID NO: 49) |
| Full VH | QMQLVQSGAEVKEPGESLRISCKGSGYSFTNFWISWVRQMPGKGLE WMGRVDPGYSYSTYSPSFQGHVTISADKSTSTAYLQWNSLKASDTA MYYCARVQYSGYYDWFDPWGQGTLVTVSS (SEQ ID NO: 50) | | |
| DNA | cagatgcagctggtgcagtccggagcagaggtgaaagagcccggggagtctctgaggatctcct gtaagggttctggatacagcttcaccaacttctggatcagctgggtgcgccagatgcccgggaaa ggcctggagtggatggggagggttgatcctggctactcttatagcacctacagcccgtccttccaag gccacgtcaccatctcagctgacaagtcatccagcactgcctacctgcagtggaacagcctgaag gcctcggacaccgccatgtattactgtgcgagagtacaatatagtggctactatgactggttcgacc cctggggccagggaaccctggtcaccgtctcctca (SEQ ID NO: 51) | | |
| Full VL | QAVVTQPPSASGTPGQRVTISCSGSSSNIGSNTVNWYQQVPGTAPK LLIYSNNQRPSGVPDRFSGSKSGTSASLAISGLQSEDEADYYCAAWD DSLNGWVFGGGTKLTVLG (SEQ ID NO: 52) | | |
| DNA | caggctgtggtgactcagccaccctcagcgtctgggaccccgggcagagggtcaccatctcttgt tctggaagcagctccaacatcggaagtaatactgtaaactggtaccagcaggtcccaggaacgg cccccaaactcctcatctatagtaataatcagcggccctcaggggtccctgaccgattctctggctc | | |

TABLE 3-continued

```
            caagtctggcacctcagcctccctggccatcagtgggctccagtctgaggatgaggctgattattac
            tgtgcagcatgggatgacagcctgaatggttgggtgttcggcggagggaccaagctgaccgtcct
            aggt
            (SEQ ID NO: 53)

scFv        QAVVTQPPSASGTPGQRVTISCSGSSSNIGSNTVNWYQQVPGTAPK
            LLIYSNNQRPSGVPDRFSGSKSGTSASLAISGLQSEDEADYYCAAWD
            DSLNGWVFGGGTKLTVLGSRGGGGSGGGGSGGGGSLEMAQMQLV
            QSGAEVKEPGESLRISCKGSGYSFTNFWISWVRQMPGKGLEWMGR
            VDPGYSYSTYSPSFQGHVTISADKSTSTAYLQWNSLKASDTAMYYCA
            RVQYSGYYDWFDPWGQGTLVTVSS
            (SEQ ID NO: 54)

DNA         caggctgtggtgactcagccaccctcagcgtctgggaccccgggcagagggtcaccatctcttgt
            tctggaagcagctccaacatcggaagtaatactgtaaactggtaccagcaggtcccaggaacgg
            cccccaaactcctcatctatagtaataatcagcggccctcaggggtccctgaccgattctctggctc
            caagtctggcacctcagcctccctggccatcagtgggctccagtctgaggatgaggctgattattac
            tgtgcagcatgggatgacagcctgaatggttgggtgttcggcggagggaccaagctgaccgtcct
            aggttctagaggtggtggtggtagcggcggcggcggctctggtggtggtggatcctcagatgg
            cccagatgcagctggtgcagtccggagcagaggtgaaagagcccggggagtctctgaggatct
            cctgtaagggttctggatacagcttcaccaacttctggatcagctgggtgcgccagatgcccggga
            aggcctggagtggatggggaggttgatcctggctactcttatagcacctacagcccgtccttcca
            aggccacgtcaccatctcagctgacaagtctaccagcactgcctacctgcagtggaacagcctga
            aggcctcggacaccgccatgtattactgtgcgagagtacaatatagtggctactatgactggttcga
            cccctggggccagggaaccctggtcaccgtctcctca
            (SEQ ID NO: 55)
```

In another embodiment, the antibody or antigen binding protein is an anti-WT1 scFv or antigen binding fragment thereof that has an antigen binding region that comprises the amino acid sequence of SEQ ID NO: 72 and specifically binds to a peptide with the amino acid sequence RMFP-NAPYL (SEQ ID NO:1) in conjunction with HLA-A0201. In other embodiments, the anti-WT-1 antibody is a scFv-Fc fusion protein or full length human IgG with VH and VL regions or CDRs selected from Table 4.

TABLE 4

| Antigen Peptide | WT1 (Ext002 #15) RMFPNAPYL (SEQ ID NO: 1) | | |
|---|---|---|---|
| CDRs: | 1 | 2 | 3 |
| VH | GYNFSNKWIG (SEQ ID NO: 56) | IIYPGYSDITYSPSFQG (SEQ ID NO: 57) | HTALAGFDY (SEQ ID NO: 58) |
| DNA | ggctacaactttagcaaca agtggatcggc (SEQ ID NO: 59) | atcatctatcccggttactcgga catcacctacagcccgtccttc caaggc (SEQ ID NO: 60) | cacacagctttggccggctttg actac (SEQ ID NO: 61) |
| VL | RASQNINKWLA (SEQ ID NO: 62) | KASSLES (SEQ ID NO: 63) | QQYNSYAT (SEQ ID NO: 64) |
| DNA | Cgggccagtcagaatatc aataagtggctggcc (SEQ ID NO: 65) | aaggcgtctagtttagaaagt (SEQ ID NO: 66) | caacaatataatagttatgcga cg (SEQ ID NO: 67) |
| Full VH | QVQLVQSGAEVKKPGESLKISCKGSGYNFSNKWIGWVRQLPGRGLE WIAIIYPGYSDITYSPSFQGRVTISADTSINTAYLHWHSLKASDTAMYYC VRHTALAGFDYWGLGTLVTVSS (SEQ ID NO: 68) | | |
| DNA | caggtgcagctggtgcagtctggagcagaggtgaaaaagcccggagagtctctgaagatctcctg taagggttctggctacaactttagcaacaagtggatcggctgggtgcgccaattgcccgggagagg cctggagtggatagcaatcatctatcccggttactcggacatcacctacagcccgtccttccaaggc cgcgtcaccatctccgccgacacgtccattaacaccgcctacctgcactggcacagcctgaaggc ctcggacaccgccatgtattattgtgtgcgacacacagctttggccggctttgactactggggcctgg gcaccctggtcaccgtctcctca (SEQ ID NO: 69) | | |
| Full VL | DIQMTQSPSTLSASVGDRVTITCRASQNINKWLAWYQQRPGKAPQLLI YKASSLESGVPSRFSGSGSGTEYTLTISSLQPDDFATYYCQQYNSYAT FGQGTKVEIKR (SEQ ID NO: 70) | | |
| DNA | gacatccagatgacccagtctcctccaccctgtctgcatctgtaggagacagagtcacaatcacttg ccggggccagtcagaatatcaataagtggctggcctggtatcagcagagaccagggaaagcccct cagctcctgatctataaggcgtctagtttagaaagtggggtcccatctaggttcagcggcagtggatc tgggacagaatacactctcaccatcagcagcctgcagcctgatgattttgcaacttattactgccaac | | |

TABLE 4-continued

| | |
|---|---|
| | aatataatagttatgcgacgttcggccaagggaccaaggtggaaatcaaacgt<br>(SEQ ID NO: 71) |
| scFv | DIQMTQSPSTLSASVGDRVTITCRASQNINKWLAWYQQRPGKAPQLLI<br>YKASSLESGVPSRFSGSGSGTEYTLTISSLQPDDFATYYCQQYNSYAT<br>FGQGTKVEIKRSRGGGGSGGGGSGGGGSLEMAQVQLVQSGAEVKK<br>PGESLKISCKGSGYNFSNKWIGWVRQLPGRGLEWIAIIYPGYSDITYSP<br>SFQGRVTISADTSINTAYLHWHSLKASDTAMYYCVRHTALAGFDYWGL<br>GTLVTVSS<br>(SEQ ID NO: 72) |
| DNA | gacatccagatgacccagtctccttccaccctgtctgcatctgtaggagacagagtcacaatcacttg<br>ccgggccagtcagaatatcaataagtggctggcctggtatcagcagagaccagggaaagcccct<br>cagctcctgatctataaggcgtctagtttagaaagtggggtcccatctaggttcagcggcagtggatc<br>tgggacagaatacactctcaccatcagcagcctgcagcctgatgattttgcaacttattactgccaac<br>aatataatagttatgcgacgttcggccaagggaccaaggtggaaatcaaacgttctagaggtggt<br>ggtggtagcggcggcggctctggtggtggtggatccctcgagatggcccaggtgcag<br>ctggtgcagtctggagcagaggtgaaaaagcccggagagtctctgaagatctcctgtaagggttct<br>ggctacaactttagcaacaagtggatcggctgggtgcgccaattgcccgggagaggcctggagtg<br>gatagcaatcatctatcccggttactcggacatcacctacagcccgtccttccaaggccgcgtcacc<br>atctccgccgacacgtccattaacaccgcctacctgcactggcacagcctgaaggcctcggacac<br>cgccatgtattattgtgtgcgacacacagctttggccggctttgactactggggcctgggcaccctggt<br>caccgtctcctca<br>(SEQ ID NO: 73) |

In another embodiment, the antibody or antigen binding protein is an anti-WT1 scFv or antigen binding fragment thereof that has an antigen binding region that comprises the amino acid sequence of SEQ ID NO: 90 and specifically binds to a peptide with the amino acid sequence RMFP-NAPYL (SEQ ID NO: 1) in conjunction with HLA-A0201. In other embodiments, the anti-WT-1 antibody is a scFv-Fc fusion protein or full length human IgG with VH and VL regions or CDRs selected from Table 5.

TABLE 5

| Antigen<br>Peptide | WT1 (Ext002 #18)<br>RMFPNAPYL (SEQ ID NO: 1) | | |
|---|---|---|---|
| CDRs: | 1 | 2 | 3 |
| VH | GFTFDDYGMS<br>(SEQ ID NO: 74) | GINWNGGSTGYADS<br>VRG<br>(SEQ ID NO: 75) | ERGYGYHDPHDY<br>(SEQ ID NO: 76) |
| DNA | gggttcacctttgatgattat<br>ggcatgagc<br>(SEQ ID NO: 77) | ggtattaattggaatggtggt<br>agcacaggttatgcagactc<br>tgtgaggggc<br>(SEQ ID NO: 78) | gagcgtggctacgggtacca<br>tgatccccatgactac<br>(SEQ ID NO: 79) |
| VL | GRNNIGSKSVH<br>(SEQ ID NO: 80) | DDSDRPS<br>(SEQ ID NO: 81) | QVWDSSSDHVV<br>(SEQ ID NO: 82) |
| DNA | gggagaaacaacattgg<br>aagtaaaagtgtgcac<br>(SEQ ID NO: 83) | gatgatagcgaccggccctc<br>a<br>(SEQ ID NO: 84) | caggtgtgggatagtagtagt<br>gatcatgtggta<br>(SEQ ID NO: 85) |
| Full<br>VH | EVQLVQSGGGVVRPGGSLRLSCAASGFTFDDYGMSWVRQAPGKG<br>LEWVSGINWNGGSTGYADSVRGRFTISRDNAKNSLYLQMNSLRAE<br>DTALYYCARERGYGYHDPHDYWGQGTLVTVSS<br>(SEQ ID NO: 86) | | |
| DNA | gaagtgcagctggtgcagtctgggggaggtgtggtacggcctgggggtccctgagactctcct<br>gtgcagcctctgggttcacctttgatgattatggcatgagctgggtccgccaagctccagggaag<br>gggctggagtgggtctctggtattaattggaatggtggtagcacaggttatgcagactctgtgagg<br>ggccgattcaccatctccagagacaacgccaagaactccctgtatctgcaaatgaacagtctg<br>agagccgaggacacggccttgtattactgtgcgagagagcgtggctacgggtaccatgatccc<br>catgactactggggccaaggcaccctggtgaccgtctcctca<br>(SEQ ID NO: 87) | | |
| Full<br>VL | QSVVTQPPSVSVAPGKTARITCGRNNIGSKSVHWYQQKPGQAPVL<br>VVYDDSDRPSGIPERFSGSNSGNTATLTISRVEAGDEADYYCQVW<br>DSSSDHVVFGGGTKLTVLG<br>(SEQ ID NO: 88) | | |
| DNA | cagtctgtcgtgacgcagccgccctcggtgtcagtggccccaggaaagacggccaggattac<br>ctgtgggagaaacaacattggaagtaaaagtgtgcactggtaccagcagaagccaggccag<br>gcccctgtgctggtcgtctatgatgatagcgaccggccctcagggatccctgagcgattctctgg<br>ctccaactctgggaacacgccaccctgaccatcagcagggtcgaagccggggatgaggcc<br>gactattactgtcaggtgtgggatagtagtagtgatcatgtggtattcggcggagggaccaagct | | |

TABLE 5-continued

```
            gaccgtcctaggt
            (SEQ ID NO: 89)

scFv        QSVVTQPPSVSVAPGKTARITCGRNNIGSKSVHWYQQKPGQAPVL
            VVYDDSDRPSGIPERFSGSNSGNTATLTISRVEAGDEADYYCQVW
            DSSSDHVVFGGGTKLTVLGSRGGGGSGGGGSGGSLEMAEVQLVQ
            SGGGVVRPGGSLRLSCAASGFTFDDYGMSWVRQAPGKGLEWVS
            GINWNGGSTGYADSVRGRFTISRDNAKNSLYLQMNSLRAEDTALYY
            CARERGYGYHDPHDYWGQGTLVTVSS
            (SEQ ID NO: 90)

DNA         cagtctgtcgtgacgcagccgccctcggtgtcagtggcccaggaaagacggccaggattac
            ctgtgggagaaacaacattggaagtaaaagtgtgcactggtaccagcagaagccaggccag
            gcccctgtgctggtcgtctatgatgatagcgaccggccctcagggatccctgagcgattctctgg
            ctccaactctgggaacacggccaccctgaccatcagcagggtcgaagcggggatgaggcc
            gactattactgtcaggtgtgggatagtagtagtgatcatgtggtattcggcggagggaccaagct
            gaccgtcctaggttctagaggtggtggtggtagcggcggcggcggctctggtggatccc
            tcgagatggccgaagtgcagctggtgcagtctggggggaggtgtggtacggcctgggggtcc
            ctgagactctcctgtgcagcctctgggttcacctttgatgattatggcatgagctgggtccgccaag
            ctccagggaaggggctggagtgggtctctggtattaattggaatggtggtagcacaggttatgca
            gactctgtgaggggccgattcaccatctccagagacaacgccaagaactccctgtatctgcaa
            atgaacagtctgagagccgaggacacggccttgtattactgtgcgagagagcgtggctacggg
            taccatgatccccatgactactggggccaaggcaccctggtgaccgtctcctca
            (SEQ ID NO: 91)
```

In another embodiment, the antibody or antigen binding protein is an anti-WT1 scFv or antigen binding fragment thereof that has an antigen binding region that comprises the amino acid sequence of SEQ ID NO: 108 and specifically binds to a peptide with the amino acid sequence RMFP-NAPYL (SEQ ID NO: 1) in conjunction with HLA-A0201. In other embodiments, the anti-WT-1 antibody is a scFv-Fc fusion protein or full length human IgG with VH and VL regions or CDRs selected from Table 6.

TABLE 6

| Antigen Peptide | WT1 (Ext002 #23) RMFPNAPYL (SEQ ID NO. 1) | | |
|---|---|---|---|
| CDRs: | 1 | 2 | 3 |
| VH | GFSVSGTYMG (SEQ ID NO. 92) | LLYSGGGTYHPASLQG (SEQ ID NO. 93) | GGAGGGHFDS (SEQ ID NO. 94) |
| DNA | ggttctccgtcagtggcaccttctttatagtggtggcggcac ctacatgggc (SEQ ID NO. 95) | ataccacccagcgtccctgca gggc (SEQ ID NO. 96) | gaggggcaggaggtggcc actttgactcc (SEQ ID NO. 97) |
| VL | TGSSSNIGAGYDVH (SEQ ID NO. 98) | GNSNRPS (SEQ ID NO. 99) | AAWDDSLNGYV (SEQ ID NO. 100) |
| DNA | actgggagcagctccaac atcggggcaggttatgatgt acac (SEQ ID NO. 101) | ggtaacagcaatcggccctca (SEQ ID NO. 102) | gcagcatgggatgacagcct gaatggttatgtc (SEQ ID NO. 103) |
| Full VH | EVQLVETGGGLLQPGGSLRLSCAASGFSVSGTYMGWVRQAPGKGLE WVALLYSGGGTYHPASLQGRFIVSRDSSKNMVYLQMNSLKAEDTAVY YCAKGGAGGGHFDSWGQGTLVTVSS (SEQ ID NO. 104) | | |
| DNA | gaggtgcagctggtggagaccggaggaggcttgctccagccgggggggtccctcagactctcctg tgcagcctctgggttctccgtcagtggcacctacatgggctgggtccgccaggctccagggaaggg actggagtgggtcgcacttctttatagtggtggcggcacataccacccagcgtcctgcagggccg attcatcgtctccagagacagctccaagaatatggtctatcttcaaatgaatagcctgaaagccgag gacacggccgtctattactgtgcgaaaggaggggcaggaggtggccactttgactcctggggcca aggcaccctggtgaccgtctcctca (SEQ ID NO. 105) | | |
| Full VL | QSVLTQPPSVSGAPGQRVTISCTGSSSNIGAGYDVHWYQQLPGTAPK LLIYGNSNRPSGVPDRFSGSKSGTSASLAISGLQSEDEADYYCAAWD DSLNGYVFGTGTKLTVLG (SEQ ID NO. 106) | | |
| DNA | cagtctgtgttgacgcagccgccctcagtgtctggggcccagggcagagggtcaccatctcctgc actgggagcagctccaacatcggggcaggttatgatgtacactggtaccagcagcttccaggaac agccccccaaactcctcatctatggtaacagcaatcggccctcaggggtccctgaccgattctctggc tccaagtctggcacctcagcctccctggccatcagtgggctccagtctgaggatgaggctgattatta | | |

TABLE 6-continued

```
         ctgtgcagcatgggatgacagcctgaatggttatgtcttcggaactgggaccaagctgaccgtccta
         ggt
         (SEQ ID NO. 107)

scFv     QSVLTQPPSVSGAPGQRVTISCTGSSSNIGAGYDVHWYQQLPGTAPK
         LLIYGNSNRPSGVPDRFSGSKSGTSASLAISGLQSEDEADYYCAAWD
         DSLNGYVFG
         TGTKLTVLGSRGGGSGGGGSGGGGSLEMAEVQLVETGGGLLQPG
         GSLRLSCAASGFSVSGTYMGWVRQAPGKGLEWVALLYSGGGTYHPA
         SLQGRFIVSRDSSKNMVYLQMNSLKAEDTAVYYCAKGGAGGGHFDS
         WGQGTLVTVSS
         (SEQ ID NO. 108)

DNA      cagtctgtgttgacgcagccgccctcagtgtctggggcccagggcagagggtcaccatctcctgc
         actgggagcagctccaacatcggggcaggttatgatgtacactggtaccagcagcttccaggaac
         agcccccaaactcctcatctatggtaacagcaatcggccctcagggggtccctgaccgattctctggc
         tccaagtctggcacctcagcctcctggccatcagtgggctccagtctgaggatgaggctgattatta
         ctgtgcagcatgggatgacagcctgaatggttatgtcttcggaactgggaccaagctgaccgtccta
         ggttctagaggtggtggtggtagcggcggcggcggctctggtggtggtggatccctcgag
         atggccgaggtgcagctggtggagaccgaggaggcttgctccagccgggggggtccctcaga
         ctctcctgtgcagcctctgggttctccgtcagtggcacctacatgggctgggtccgccaggctccagg
         gaagggactggagtgggtcgcacttctttatagtggtggcggcacataccacccagctccctgca
         gggccgattcatcgtctccagagacagctccaagaatatggtctatcttcaaatgaatagcctgaaa
         gccgaggacacggccgtctattactgtgcgaaaggaggggcaggaggtggccactttgactcctg
         gggccaaggcaccctggtgaccgtctcctca
         (SEQ ID NO. 109)
```

Other embodiments of the disclosed antibodies and antigen binding proteins encompass those comprising light and heavy hypervariable regions and constant regions, for example as shown in Tables 7 (heavy chain), 8 (light chain) and 9 (constant regions).

TABLE 7

|  | CDR-H1 | CDR-H2 | CDR-H3 | SEQ ID NO. |
|---|---|---|---|---|
| Group I | | | | |
| EXT002-12(166) | SNAVAWN | RTYRGSTYY---ALSV | G-SNSAFDF | 119-121 |
| EXT002-5(184) | SNSAAWN | RTYYGSKWYNDYAVSV | GRLGDAFDI | 122-124 |
| EXT002-8(184) | SDGAAWN | RTYYRSKWYNDYAVSV | GDYYYGMDV | 125-127 |
| Consensus(191) | SNAAAWN | RTYYGSKWYNDYAVSV | G    AFDI | 128-130 |
| Group II | | | | |
| EXT002-14(163) | SYWIS | RIDPSDSYTNYSPSFQG | GD------YDFYLDP-- | 131-133 |
| EXT002-25(163) | SYGIS | WISAYNGNTNYAQKLQG | DLYSSGWYESYYYGMDV | 134-136 |
| EXT002-3(186) | SYAIS | GIIPIFGTANYAQKFQG | RIP-P------YYGMDV | 137-139 |
| EXT002-30(163) | SYGIS | WISAHNGNTNYAQKLQG | DR-------VWFGDLSD | 134, 140, 141 |
| EXT002-33(163) | SYAIS | GIIPIFGTANYAQKEQG | NYDFWSG-----DAFDI | 137, 142, 143 |
| Consensus(188) | SYAIS |  I P  G TNYAQKFQG |          FY GMDV | 137, 144, 145 |
| Group III | | | | |
| EXT002-34(161) | DYGMS | GINWNGGSTGYADSV | ERGY-GYHDPHDY | 146-148 |
| EXT002-40(157) | NYTMN | SISLSGAYIYYADSL | EGYSSSVYDAFDL | 149-151 |
| EXT002-45(165) | SYGMH | GILSDGGKDYYVDSV | CSSN-YGNDAFDI | 152-154 |
| EXT002-48(165) | TYSMN | SISSGAYSIFYADSV | DQYYGDKWDAFDI | 155-157 |
| Consensus(170) | SYGMN | SISS GGSIYYADSV | E YY   WDAFDI | 158-160 |

TABLE 8

| | CDR-L1 | CDR-L2 | CDR-L3 | SEQ ID NOS. |
|---|---|---|---|---|
| Group I | | | | |
| EXT002-1 (46) | CSGSSSNIGS-NTVNSNNQRPSG | AAWDDSLNG--WVFG | | 161-163 |
| EXT002-10 (46) | CSGSSSNIGS-NTVNSNNQRPSG | EAWDDSLKG--PVFG | | 161, 162, 164 |
| EXT002-12 (22) | CTGSSSNIGAGYDVHGNSNRPSG | QSYDSSLSADNYVFG | | 165-167 |
| EXT002-13 (46) | CSGSSSNIGS-NTVNSNNQRPSG | AAWDDSLNG--WVFG | | 161-163 |
| EXT002-2 (46) | CSGSSSNIGR-NIVNSNIERPSG | ASWDDSLNG--VLFG | | 168-170 |
| EXT002-20 (46) | CSGSRSNIAS-NGVGKNDQRPSG | SAWDDSLDGH-VVFG | | 171-173 |
| EXT002-23 (46) | CTGSSSNIGAGYDVHGNSNRPSG | AAWDDSLNG--YVFG | | 165, 166, 174 |
| EXT002-25 (22) | CSGSSSNIGS-STVNSNSQRPSG | AAWDDSLNG--VVFG | | 175-177 |
| EXT002-3 (46) | CSGSSSNIGS-NYVYRSNQRPSG | AAWDDSLNG--VVFG | | 178, 179, 177 |
| EXT002-30 (22) | CSGSSSNIGR-NTVNSNNQRPSG | AAWDDSLNG--YVFG | | 180, 162, 174 |
| EXT002-33 (22) | CSGSSSNIGN-DYVSDNNKRPSG | GTWDNSLSA--WVFG | | 181-183 |
| EXT002-36 (22) | CSGSSSNIGS-NSVYNNNQRPSG | ATWDDSLSG--WVFG | | 184-186 |
| EXT002-40 (22) | CSGSSSNIGS-NYVYRNNQRPSG | AAWDDSLSA--WVFG | | 178, 187, 188 |
| EXT002-42 (46) | CSGSTSNIGS-YYVSDNNNRPSG | GTWDSSLSA--WVFG | | 189-191 |
| EXT002-45 (22) | CSGSSSNIGN-NYVSDNNKRPSG | GTWDSSLSA--WVFG | | 192, 182, 191 |
| EXT002-48 (22) | CSGSNSNIGT-NTVTSNFERPSG | SAWDDSFNG--PVFG | | 193-195 |
| EXT002-6 (46) | CSGSSSNIGS-NYVSRNNQRPSG | AAWDDGLRG--YVFG | | 196, 187, 197 |
| EXT002-9 (22) | CSGSSSNIGS-NTVNSNNQRPSG | EAWDDSLKG--PVFG | | 161, 162, 164 |
| Consensus (46) | CSGSSSNIGS N V  NNQRPSG | AAWDDSL G  WVFG | | 161-163 |
| Group II | | | | |
| EXT002-24 (24) | RASQSISSYLN | AASSLQS | QQSYSTP--T | 198-200 |
| EXT002-31 (24) | RASQGISNYLA | AASTLQS | QKYNSAPGVT | 201-203 |
| EXT002-35 (24) | RASQSINGWLA | RASTLQS | QQSSSLP-FT | 204-206 |
| EXT002-5 (48) | RASQSISSYLN | AASSLQS | QQSYSTP-LT | 198-200 |
| EXT002-7 (48) | RASQGISYYLA | AASTLKS | QQLNSYP-LT | 207-209 |
| EXT002-B (48) | RASQSISSYLN | AASSLQS | QQSYSTP-WT | 198-200 |
| Consensus (48) | RASQSISSYLN | AASSLQS | QQSYSTP LT | 198-200 |
| Group III | | | | |
| EXT002-16 (23) | GGNNIGSKSVH | DDSDRPS | QVWDSSSDHPV | 210-212 |
| EXT002-17 (47) | GGNNIGSKSVH | DDSDRPS | QVWDSSGDHPV | 210, 211, 213 |
| EXT002-19 (47) | GGNNIGSKSVH | YDSDRPS | QVWDSSSDHPV | 210, 214, 212 |
| EXT002-21 (19) | GGTNIGSRFVH | DDSDRPS | QVWDSSGDHPV | 215, 211, 213 |

TABLE 8-continued

|  | CDR-L1 | CDR-L2 | CDR-L3 | SEQ ID NOS. |
|---|---|---|---|---|
| EXT002-22 (47) | GGNNVESKSVH | YDRDRPS | EVWDSGSDHPV | 216-218 |
| EXT002-32 (23) | GGKNIGSKSVH | YDSDRPS | QVWDSGSDHYV | 219, 214, 220 |
| EXT002-34 (23) | GGNNIGSKSVH | DDSDRPS | QVWISSGDRVI | 210, 211, 221 |
| EXT002-43 (23) | GGDNIGSQGVH | YDTDRPS | QVWGASSDHPV | 222-224 |
| Consensus (47) | GGNNIGSKSVH | YDSDRPS | QVWDSSSDHPV | 210, 214, 212 |
| Group IV |  |  |  |  |
| EXT002-11 (47) | TGTSSDVGGYNYVS | DVSKRPS | GIYTYSDSW--V | 225-227 |
| EXT002-14 (23) | TGTSSDVGGYNYVS | DVGNRPS | SSYTSSSTR--V | 225, 228, 229 |
| EXT002-26 (23) | TGTRSDVGLYNYVA | DVIYRPG | SSYTNTGTV--L | 230-232 |
| EXT002-4 (47) | TGTSSDFGDYDYVS | DVSDRPS | QSYDSSLSGSGV | 233-235 |
| Consensus (47) | TGTSSDVGGYNYVS | DVS RPS | SSYTSS S  V | 225, 234, 229 |

TABLE 9

Constant Regions

| Human heavy chain constant region and IgG1 Fc domain sequence | ASTKGPSVFPLAPSSKSTSGGTAALGCLVKDYFPEPVTV SWNSGALTSGVHTFPAVLQSSGLYSLSSVVTVPSSSLGT QTYICNVNHKPSNTKVDKRVEPKSCDKTHTCPPCPAPEL LGGPSVFLFPPKPKDTLMISRTPEVTCVVVDVSHEDPEV KFNWYVDGVEVHNAKTKPREEQYNSTYRVVSVLTVLHQD WLNGKEYKCKVSNKALPAPIEKTISKAKGQPREPQVYTL PPSRDELTKNQVSLTCLVKGFYPSDIAVEWESNGQPENN YKTTPPVLDSDGSFFLYSKLTVDKSRWQQGNVFSCSVMH EALHNHYTQKSLSLSPGK (SEQ ID NO. 236) |
|---|---|
| Human light chain (kappa) | TVAAPSVFIFPPSDEQLKSGTASVVCLLNNFYPREAKVQ WKVDNALQSGNSQESVTEQDSKDSTYSLSSTLTLSKADY EKHKVYACEVTHQGLSSPVTKSFNRGEC (SEQ ID NO. 237) |
| Human light chain (lambda) | QPKANPTVTLFPPSSEELQANKATLVCLISDFYPGAVTV AWKADGSPVKAGVETTKPSKQSNNKYAASSYLSLTPEQW KSHRSYSCQVTHEGSTVEKTVAPTECS (SEQ ID NO. 238) |

The invention relates to recombinant antigen-binding proteins, antibodies and antigen binding fragments thereof that specifically recognize epitopes of a complex of a peptide/protein fragment derived from an intracellular protein, and an MHC class I molecule, for example, as the complex might be displayed at the cell surface during antigen presentation. The heavy and light chains of an antibody of the invention may be full-length (e.g., an antibody can include at least one, and preferably two, complete heavy chains, and at least one, and preferably two, complete light chains) or may include an antigen-binding portion (a Fab, F(ab')$_2$, Fv or a single chain Fv fragment ("scFv")). In other embodiments, the antibody heavy chain constant region is chosen from, e.g., IgG1, IgG2, IgG3, IgG4, IgM, IgA1, IgA2, IgD, and IgE, particularly chosen from, e.g., IgG1, IgG2, IgG3, and IgG4, more particularly, IgG1 (e.g., human IgG1). In another embodiment, the antibody light chain constant region is chosen from, e.g., kappa or lambda, particularly kappa.

The antibodies and antigen binding proteins of the present invention are intended to encompass bispecific antibodies, including bispecific T-cell engaging antibodies, that is, antibodies comprising two antibody variable domains on a single polypeptide chain that are able to bind two separate antigens. Where a first portion of a bispecific antibody binds an antigen on a tumor cell for example and a second portion of a bispecific antibody recognizes an antigen on the surface of a human immune effector cell, the antibody is capable of recruiting the activity of that effector cell by specifically binding to the effector antigen on the human immune effector cell. In some instances, bispecific antibodies, therefore, are able to form a link between effector cells, for example, T cells and tumor cells, thereby enhancing effector function.

In one embodiment, the constant region/framework region is altered, for example, by amino acid substitution, to modify the properties of the antibody (e.g., to increase or decrease one or more of: antigen binding affinity, Fc receptor binding, antibody carbohydrate, for example, glycosylation, fucosylation etc, the number of cysteine residues, effector cell function, effector cell function, complement function or introduction of a conjugation site). Furthermore, conjugation of the antibody to a drug, toxin, radioisotope, cytokine, inflammatory peptide or cytotoxic agent is also contemplated.

In one embodiment, the antibody is an anti-WT1/A2 antibody and comprises the human IgG1 constant region and Fc domain shown in Table 9. In one embodiment, the anti-WT1/A2 antibody comprises a human kappa sequence, or a human lambda sequence having the sequence set forth in Table 9. The amino acid sequences for some complementarity determining regions (CDRs) of antibodies of the invention are shown in Tables 1-8.

The present invention is based on the identification of antigen-specific binding sequences from which a variety of antigen-binding proteins can be produced. In addition to antibodies specific for an antigen that represents a protein fragment (peptide)/HLA complex similar to that typically recognized by a T-cell receptor following antigen processing and presentation of the protein to the T-cell, identification of amino acid and nucleic sequences as disclosed herein for the preparation of antibodies can also be used to generate other antigen-binding molecules including chimeric antigen receptors (CARs), with specificity for the protein fragment (peptide)/HLA complex. These can be incorporated into cells to make them specifically cytotoxic to the antigen expressing cell.

The present invention employs a novel approach to obtaining therapeutic antibodies to any protein, including those proteins that are inaccessible because they are not expressed on the cell surface. Nearly any intracytoplasmic or intranuclear protein (in addition to cell surface proteins) is a potential target for the approach described herein. This includes, but is not limited to, oncogenic proteins, transcription factors, enzymes, etc.

In order to target tumor antigens derived from intracellular or nuclear proteins, development of a therapeutic antibody an uncommon approach was required. This approach is to generate recombinant mAbs that recognize the peptide/MHC complex expressed on the cell surface, with the same specificity as a T-cell receptor (TCR). Such mAbs share functional homology with TCRs regarding target recognition, but confer higher affinity and capabilities of arming with potent cytotoxic agents that antibodies feature. Technically, TCR-like mAbs may be generated by conventional hybridoma techniques known to those of skill in the art, to produce human, humanized or chimeric antibodies.

Furthermore, fully-human mAbs are preferred for therapeutic use in humans because murine antibodies cause an immunogenicity reaction, known as the HAMA (human anti-mouse antibodies) response (24, 25), when administered to humans, causing serious side effects, including anaphylaxis and hypersensitivity reactions. This immunogenicity reaction is triggered by the human immune system recognizing the murine antibodies as foreign because of slightly different amino acid sequences from natural human antibodies. Humanization methods known in the art (26, 27) can be employed to reduce the immunogenicity of murine-derived antibodies (28).

Recently, the use of phage display libraries has made it possible to select large numbers of Ab repertoires for unique and rare Abs against very defined epitopes (for more details on phage display see McCafferty et al., Phage antibodies: filamentous phage displaying antibody variable domains. *Nature,* 348: 552-554.) The rapid identification of human Fab or single chain Fv (ScFV) fragments highly specific for tumor antigen-derived peptide-MHC complex molecules has thus become possible (19-22). More recently, immunotoxins, generated by fusing TCR-like Fab specific for melanoma Ag MART-1 26-35/A2 or gp100 280-288/A2 to a truncated form of *Pseudomonas* endotoxin, have been shown to inhibit human melanoma growth both in vitro and in vivo (23). In addition, by engineering full-length mAb using the Fab fragments, it is possible to directly generate a therapeutic human mAb, by-passing months of time-consuming work, normally needed for developing therapeutic mAbs. The present invention involves the development of a TCR-like, fully human mAb that recognizes, for example, the WT1 peptide/HLA-A2 complex (RMFPNAPYL, SEQ ID NO: 1) for cancer therapy.

Recombinant antibodies with TCR-like specificity represent a new and valuable tool for research and therapeutic applications in tumor immunology and immunotherapy. WT1 is a well-established and validated tumor antigen that has been investigated throughout the world as a marker, prognostic factor and therapeutic target. It was recently prioritized as the top priority tumor antigen by an NCI task force (29).

Identification of Peptides with High Predictive Binding to HLA Molecules

In one embodiment, the present invention relates to a method for the generation of antibodies that specifically bind to HLA-restricted peptides, which, when presented as part of a peptide/MHC complex are able to elicit a specific cytotoxic T-cell response. HLA class I molecules present endogenous derived peptides of about 8-12 amino acids in length to $CD8^+$ cytotoxic T lymphocytes. Peptides to be used in the method of the present invention are generally about 6-22 amino acids in length, and in some embodiments, between about 9 and 20 amino acids and comprise an amino acid sequence derived from a protein of interest, for example, human WT1 protein (Genbank accession no. P19544) or an analog thereof.

Peptides suitable for use in generating antibodies in accordance with the method of the present invention can be determined based on the presence of HLA-A0201-binding motifs and the cleavage sites for proteasomes and immune-proteasomes using computer prediction models known to those of skill in the art. For predicting MHC class I binding sites, such models include, but are not limited to, ProPred1 (described in more detail in Singh and Raghava, *ProPred: prediction of HLA-DR binding sites. BIOINFORMATICS* 17(12):1236-1237 2001), and SYFPEITHI (see Schuler et al. *SYFPEITHI, Database for Searching and T-Cell Epitope Prediction.* in *Immunoinformatics Methods in Molecular Biology,* vol 409(1): 75-93 2007)

HLA-A*0201 is expressed in 39-46% of all caucasians and therefore, represents a suitable choice of MHC antigen for use in the present method. For preparation of one embodiment of a WT1 peptide antigen, amino acid sequences and predicted binding of putative $CD84^+$ epitopes to HLA-A0201 molecules were identified using the predictive algorithm of the SYFPEITHI database (see Schuler et al. *SYFPEITHI, Database for Searching and T-Cell Epitope Prediction.* in *Immunoinformatics Methods in Molecular Biology,* vol 409(1): 75-93 2007).

Once appropriate peptides have been identified, peptide synthesis may be done in accordance with protocols well known to those of skill in the art. Because of their relatively small size, the peptides of the invention may be directly synthesized in solution or on a solid support in accordance with conventional peptide synthesis techniques. Various automatic synthesizers are commercially available and can be used in accordance with known protocols. The synthesis of peptides in solution phase has become a well-established procedure for large-scale production of synthetic peptides and as such is a suitable alternative method for preparing the peptides of the invention. (See for example, *Solid Phase Peptide Synthesis* by John Morrow Stewart and Martin et al. *Application of Almez-mediated Amidation Reactions to Solution Phase Peptide Synthesis,* Tetrahedron Letters Vol. 39, pages 1517-1520 1998.)

Each of the peptides used in the protocols described herein was purchased and synthesized by Genemed Synthesis, Inc. (San Antonio, Tex.) using fluorenylmethoxycarbonyl chemistry and solid-phase synthesis and purified by high-pressure liquid chromatography. The quality of the peptides was assessed by high-performance liquid chromatography analysis, and the expected molecular weight was observed using matrix-assisted laser desorption mass spectrometry. Peptides were sterile and 70% to 90% pure. The peptides were dissolved in DMSO and diluted in PBS (pH 7.4) or saline at 5 mg/mL and stored at −80° C.

Subsequent to peptide selection, binding activity of selected peptides is tested using the antigen-processing-deficient T2 cell line, which increases expression of HLA-A when stabilized by a peptide in the antigen-presenting groove. Briefly, T2 cells are pulsed with peptide for a time sufficient to induce HLA-A expression. HLA-A expression of T2 cells is then measured by immunostaining with a fluorescently labeled monoclonal antibody specific for HLA-A (for example, BB7.2) and flow cytometry. Fluorescence index (FI) is calculated as the mean fluorescence intensity (MFI) of HLA-A0201 on T2 cells as determined by fluorescence-activated cell-sorting analysis, using the formula FI=(MFI[T2 cells with peptide]/MFI [T2 cells without peptide]−1.

Fully human T-cell receptor (TCR)-like antibodies to Wilm's tumor oncognene protein (WT1) were produced using the method disclosed herein. TCR-like anti-WT1 antibodies generated by phage display technology are specific for a WT1 peptide/HLA complex similar to that which induces HLA-restricted cytotoxic CD8 T-cells.

The WT1 protein sequence was screened using the SYFPEITHI algorithm and WT1 peptides (for example, peptides designated 428, 328, and 122) were identified that had predicted high-affinity binding to multiple HLA molecules that are highly expressed in the Caucasian population. Peptide 428 spans WT1 amino acids 428-459, peptide 328 spans WT1 amino acids 328-349, and peptide 122 spans WT1 amino acids 122-140 (see FIG. 1)

Heteroclitic peptides can also be designed by conservative amino acid substitutions of MHC-binding residues expected to enhance the affinity toward the MHC class 1 allele, as predicted by the prediction algorithm. WT1 peptide 122 comprises within it a known CD8$^+$ epitope (126-134). In one embodiment, therefore, a modified peptide of the peptide that spans the WT1 amino acid residues 126-134 and contains a modified amino acid at positions may be used. Peptides used for alanine mutagenesis of WT1A (otherwise designated RFM) were named based on the position where the substitution was made. Examples of WT1 peptides which may be used are shown in Table 10 along with irrelevant peptides, RHAMM-R3 and EW.

TABLE 10

| | | |
|---|---|---|
| WT1A (RMF) | RMFPNAPYL | SEQ ID NO.: 1 |
| WT1A1-B | AMFPNAPYL | SEQ ID NO.: 110 |
| WT1A-3 | RMAPNAPYL | SEQ ID NO.: 111 |
| WT1A-4 | RMFANAPYL | SEQ ID NO.: 112 |
| WT1A-5 | RMFPAAPYL | SEQ ID NO.: 113 |
| WT1A-7 | RMFPNAAYL | SEQ ID NO.: 114 |
| WT1A-8 | RMFPNAPAL | SEQ ID NO.: 115 |
| RHAMM-R3 | ILSLELMKL | SEQ ID NO.: 116 |
| EW | QLQNPSYDK | SEQ ID NO.: 117 |
| RSDELVRHHNMHQRNMTKL | | SEQ ID NO.: 118 |
| PGCNKRYFKLSHLQMHSRKHTG | | SEQ ID NO.: 119 |
| SGQARMFPNAPYLPSCLES | | SEQ ID NO.: 120 |
| SGQAYMFPNAPYLPSCLES | | SEQ ID NO.: 121 |

Once a suitable peptide has been identified, the target antigen to be used for phage display library screening, that is, a peptide/HLA complex (for example, WT1 peptide/HLA-A0201) is prepared by bringing the peptide and the histocompatibility antigen together in solution to form the complex.

Selecting a High Affinity ScFV Against a WT1 Peptide

The next step is the selection of phage that bind to the target antigen of interest with high affinity, from phage in a human phage display library that either do not bind or that bind with lower affinity. This is accomplished by iterative binding of phage to the antigen, which is bound to a solid support, for example, beads or mammalian cells followed by removal of non-bound phage and by elution of specifically bound phage. In one embodiment, antigens are first biotinylated for immobilization to, for example, streptavidin-conjugated Dynabeads M-280. The phage library is incubated with the cells, beads or other solid support and non binding phage is removed by washing. Clones that bind are selected and tested.

Once selected, positive scFv clones are tested for their binding to HLA-A2/peptide complexes on live T2 cell surfaces by indirect flow cytometry. Briefly, phage clones are incubated with T2 cells that have been pulsed with Wt1-A peptide, or an irrelevant peptide (control). The cells are washed and then with a mouse anti-M13 coat protein mAb. Cells are washed again and labeled with a FITC-goat (Fab)$_2$ anti-mouse Ig prior to flow cytometry.

In other embodiments, the anti-WT1/A antibodies may comprise one or more framework region amino acid substitutions designed to improve protein stability, antibody binding, expression levels or to introduce a site for conjugation of therapeutic agents. These scFv are then used to produce recombinant human monoclonal Igs in accordance with methods known to those of skill in the art.

Methods for reducing the proliferation of leukemia cells is also included, comprising contacting leukemia cells with a WT1 antibody of the invention. In a related aspect, the antibodies of the invention can be used for the prevention or treatment of leukemia. Administration of therapeutic antibodies is known in the art.

Antibody Conjugates with Anti-Cancer Agents

Monoclonal antibodies represent the preferred vehicle for the targeted delivery of bioactive agents to cancer sites, including antibody-based delivery of cytotoxics, radionuclides or immunomodulatory cytokines. Conjugates of the antibodies of the invention with therapeutic agents, including without limitation, drugs (such as calecheamicin, aureastatin, doxorubicin), or toxins (such as ricin, diphtheria, gelonin) or radioisotopes emitting alpha or beta particles (such as, $^{90}$Y, $^{131}$I, $^{225}$Ac, $^{213}$Bi, $^{223}$Ra and $^{227}$Th), inflammatory peptides (such as IL2, TNF, IFN-γ) are encompassed by the invention.

Pharmaceutical Compositions and Methods of Treatment

WT1 antibodies of the present invention can be administered for therapeutic treatments to a patient suffering from a tumor or WT1-associated pathologic condition in an amount sufficient to prevent, inhibit, or reduce the progression of the tumor or pathologic condition. Progression includes, e.g, the growth, invasiveness, metastases and/or recurrence of the tumor or pathologic condition. Amounts effective for this use will depend upon the severity of the disease and the general state of the patient's own immune system. Dosing schedules will also vary with the disease state and status of the patient, and will typically range from a single bolus dosage or continuous infusion to multiple administrations per day (e.g., every 4-6 hours), or as indicated by the treating physician and the patient's condition.

The identification of medical conditions treatable by WT1 antibodies of the present invention is well within the ability and knowledge of one skilled in the art. For example, human individuals who are either suffering from a clinically significant leukemic disease or who are at risk of developing clinically significant symptoms are suitable for administration of the present WT1 antibodies. A clinician skilled in the art can readily determine, for example, by the use of clinical tests, physical examination and medical/family history, if an individual is a candidate for such treatment.

Non-limiting examples of pathological conditions characterized by WT1 expression include chronic myelocytic leukemia, acute lymphoblastic leukemia (ALL), acute myeloid/myelogenous leukemia (AML) and myelodysplastic syndrome (MDS). Additionally, solid tumors, in general and in particular, tumors associated with mesothelioma, ovarian cancer, gastrointestinal cancers, breast cancer, prostate cancer and glioblastoma are amenable to treatment using WT1 antibodies.

In another embodiment, therefore, the present invention provides a method of treating a medical condition by administering a WT1 antibody of the present invention in combination with one or more other agents. For example, an embodiment of the present invention provides a method of treating a medical condition by administering a WT1 antibody of the present invention with an antineoplastic or antiangiogenic agent. The WT1 antibody can be chemically or biosynthetically linked to one or more of the antineoplastic or antiangiogenic agents.

Any suitable method or route can be used to administer a WT1 antibody of the present invention, and optionally, to coadminister antineoplastic agents and/or antagonists of other receptors. Routes of administration include, for example, oral, intravenous, intraperitoneal, subcutaneous, or intramuscular administration. It should be emphasized, however, that the present invention is not limited to any particular method or route of administration.

It is noted that a WT1 antibody of the present invention can be administered as a conjugate, which binds specifically to the receptor and delivers a toxic, lethal payload following ligand-toxin internalization.

It is understood that WT1 antibodies of the invention will be administered in the form of a composition additionally comprising a pharmaceutically acceptable carrier. Suitable pharmaceutically acceptable carriers include, for example, one or more of water, saline, phosphate buffered saline, dextrose, glycerol, ethanol and the like, as well as combinations thereof. Pharmaceutically acceptable carriers may further comprise minor amounts of auxiliary substances such as wetting or emulsifying agents, preservatives or buffers, which enhance the shelf life or effectiveness of the binding proteins. The compositions of the injection may, as is well known in the art, be formulated so as to provide quick, sustained or delayed release of the active ingredient after administration to the mammal.

Other aspects of the invention include without limitation, the use of antibodies and nucleic acids that encode them for treatment of WT1 associated disease, for diagnostic and prognostic applications as well as use as research tools for the detection of WT1 in cells and tissues. Pharmaceutical compositions comprising the disclosed antibodies and nucleic acids are encompassed by the invention. Vectors comprising the nucleic acids of the invention for antibody-based treatment by vectored immunotherapy are also contemplated by the present invention. Vectors include expression vectors which enable the expression and secretion of antibodies, as well as vectors which are directed to cell surface expression of the antigen binding proteins, such as chimeric antigen receptors.

Cells comprising the nucleic acids, for example cells that have been transfected with the vectors of the invention are also encompassed by the disclosure.

For use in diagnostic and research applications, kits are also provided that contain a WT1 antibody or nucleic acids of the invention, assay reagents, buffers, and the like.

The method of the present invention will now be described in more detail with respect to representative embodiments.

Materials

Cell Samples, Cell Lines and Antibodies.

After informed consent on Memorial Sloan-Kettering Cancer Center Institutional Review Board approved protocols, peripheral blood mononuclear cells (PBMC) from HLA-typed healthy donors and patients were obtained by Ficoll density centrifugation. The sources for obtaining human mesothelioma cell lines are described previously (29). The cell lines include: H-Meso1A, JMN, VAMT, H2452, H2373, H28, MSTO, Meso 11, Meso 34, Meso 37, Meso 47, and Meso 56. All cells were HLA typed by the Department of Cellular Immunology at Memorial Sloan-Kettering Cancer Center. Leukemia cell lines LAMA81, BV173, and 697, (WT1+, A0201+) were kindly provided by Dr. H. J. Stauss (University College London, London, United Kingdom). Melanoma cell line MeWo (WT1−, A201+), SKLY16 (B-cell lymphoma; WT1−, A0201+); K562, RwLeu4, and HL60, all WT1+ leukemias, and a TAP-deficient T2 cell line were obtained from the American Type Culture Collection. The cell lines were cultured in RPMI 1640 supplemented with 5% FCS, penicillin, streptomycin, 2 mmol/L glutamine, and 2-mercaptoethanol at 37 C/5% CO2.

Monoclonal Ab against human HLA-A2 (clone BB7.2) conjugated to FITC or APC, and its isotype control mouse IgG2b/FITC or APC, to human or mouse CD3, CD19, CD56, CD33, CD34 (BD Biosciences, San Diego), goat F(ab)2 anti-human IgG conjugated with PE or FITC and goat F(ab)2 anti-mouse Ig's conjugated to fluorescent (In Vitrogen, City) were purchased. Mouse mAb to HLA-class I (W6/32) was obtained from the MSKCC Monoclonal antibody Core Facility.

Peptides.

All peptides were purchased and synthesized by Genemed Synthesis, Inc. (San Antonio, Tex.). Peptides were >90% pure. (Table 1.) The peptides were dissolved in DMSO and diluted in saline at 5 mg/mL and frozen at −180 C. Biotinylated single chain WT1 peptide/HLA-A0201 and RHAMM-3/HLA-A0201 complexes were synthesized by refolding the peptides with recombinant HLA-A2 and beta2 microglobulen (β2M) at the Tetramer facility at MSKCC.

Animals.

Eight to 10 week-old NOD.Cg-Prkdc scid IL2rgtm1WjI/SzJ mice, known as NOD scid gamma (NSG), were purchased from the Jackson Laboratory (Bar Harbor, Me.) or obtained from MSKCC animal breeding facility.

Methods

Flow Cytometry Analysis.

For cell surface staining, cells were incubated with appropriate mAbs for 30 minutes on ice, washed, and incubated with secondary antibody reagents when necessary. Flow cytometry data were collected on a FACS Calibur (Becton Dickinson) and analyzed with FlowJo V8.7.1 and 9.4.8 software.

Selection and Characterization of scFv Specific for WT1 Peptide/HLA-A0201 Complexes.

A human scFv antibody phage display library was used for the selection of mAb clones. In order to reduce the conformational change of MHC1 complex introduces by immobilizing onto plastic surfaces, a solution panning method was used in place of conventional plate panning. In brief, biotinylated antigens were first mixed with the human scFv phage library, then the antigen-scFv antibody complexes were pulled down by streptavidin-conjugated Dynabeads M-280 through a magnetic rack. Bound clones were then eluted and were used to infect E. Coli XL1-Blue. The scFv phage clones expressed in the bacteria were purified (35, 36). Panning was performed for 3-4 cycles to enrich scFv phage clones binding to HLA-A0201/WT1 complex specifically. Positive clones were determined by standard ELISA method against biotinylated single chain HLA-A0201/WT1 peptide complexes. Positive clones were further tested for their binding to HLA-A2/peptide complexes on live cell surfaces by flow cytometry, using a TAP-deficient, HLA-A0201+ cell line, T2. T2 cells were pulsed with peptides (50 ug/ml) in the serum-free RPM11640 medium, in the presence of 20 µg/ml β2 M ON. The cells were washed, and the staining was performed in following steps.

The cells were first stained with purified scFv phage clones, and followed by staining with a mouse anti-M13 mAb, and finally the goat F(ab)2 anti-mouse Ig's conjugate to FITC. Each step of the staining was done between 30-60 minutes on ice and the cells were washed twice between each step of the staining.

Engineering Full Length mAb Using the Selected ScFv Fragments.

Full-length human IgG1 of the selected phage clones were produced in HEK293 and Chinese hamster ovary (CHO) cell lines, as described (37). In brief, antibody variable regions were subcloned into mammalian expression vectors, with matching human lambda or kappa light chain constant region and human IgG1 constant region sequences. Molecular weight of the purified full length IgG antibodies were measured under both reducing and non-reducing conditions by electrophoresis.

Engineering Chimeric Antigen Receptors and Immune Effector Cells.

Nucleic acids that encode antibodies and antigen binding proteins identified herein can be used engineer recombinant immune effector cells. Methods and vectors to generate genetically modified T-cells, for example, are known in the art (See Brentjens et al., *Safety and persistence of adoptively transferred autologous CD19-targeted T cells in patients with relapsed or chemotherapy refractory B-cell leukemias* in Blood 118(18):4817-4828, November 2011).

Characterization of the Full-Length Human IgG1 for the WT1p/A2 Complex.

Initially, specificities of the fully human IgG1 mAbs for the WT1 peptide/A2 complex were determined by staining T2 cells pulsed with or without RMF or RHAMM-R3 control peptides, followed by secondary goat F(ab)2 anti-human IgG mAb conjugate to PE or FITC. The fluorescence intensity was measured by flow cytometry. The same method was used to determine the binding of the mAbs to fresh tumor cells and cell lines.

Radioimmunoassays.

WT1 ab1 was labeled with 125-I (Perkin Elmer) using the chloramine-T method (38). 100 µg antibody was reacted with 1 mCi 125-I and 20 µg chloramine-T, quenched with 200 µg Na metabisulfite, then separated from free 125-I using a 10DG column (company) equilibrated with 2% bovine serum albumin in PBS. Specific activities of products were in the range of 7-8 mCi/mg.

Hematopoietic cell lines, adherent cell lines (harvested with a non-enzymatic cell stripper (name)), PBMCs from normal donors and AML patients were obtained as described. Cells were washed once with PBS and re-suspended in 2% human serum in PBS at $10^7$ cells/mL at 0°. Cells ($10^6$ tube in duplicate) were incubated with 125-I-labeled WT1 AB1 (1 µg/mL) for 45 minutes on ice, then washed extensively with 1% bovine serum albumin in PBS at 0°. To determine specific binding, a duplicate set of cells was assayed after pre-incubation in the presence of 50-fold excess unlabeled WT1 AB1 for 20 minutes on ice. Bound radioactivity was measured by a gamma counter, specific binding was determined, and the number of bound antibodies per cell was calculated from specific activity.

Antibody-Dependent Cellular Cytotoxicity (ADCC).

Target cells used for ADCC were T2 cells pulsed with or without WT1 or RHAAM-3 peptides, and tumor cell lines without peptide pulsing. WT1 ab1 or its isotype control human IgG1 at various concentrations were incubated with target cells and fresh PBMCs at different effector: target (E:T) ratio for 16 hrs. The supernatant were harvested and the cytotoxicity was measured by LDH release assay using Cytotox 96 non-radioreactive kit from Promega following their instruction. Cytotoxicity is also measured by standard 4 hours 51Cr-release assay.

Transduction and selection of luciferase/GFP positive cells. BV173 and JMN cells were engineered to express high level of GFP-luciferase fusion protein, using lentiviral vectors containing a plasmid encoding the luc/GFP (39). Using single cell cloning, only the cells showing high level GFP expression were selected by flow cytometry analysis and were maintained and used for the animal study.

Therapeutic Trials of the WT1 Ab 1 in a Human Leukemia Xenograft NSG Model.

Two million BV173 human leukemia cells were injected IV into NSG mice. On day 5, tumor engraftment was confirmed by firefly luciferase imaging in all mice that were to be treated; mice were then randomly divided into different treatment groups. On day 6 and day 10, mAb WT1 ab1 or the isotype control mAb were injected IV. In animals that also received human effector cells with or without mAb, cells (CD34 and CD3-depleted healthy donor human PBMCs) were injected IV into mice ($10^7$ cells/mouse) 4 hr before the mAb injections. Tumor growth was assessed by luminescence imaging once to twice a week, and clinical activity was assessed daily.

Selection and Characterization of scFv Specific for WT1 Peptide/HLA-A0201 Complexes.

Selection of an WT1-specific scFV is achieved using a 9-mer WT1-derived peptide comprising amino acids 126-134 (RMFPNAPYL, SEQ ID NO: 1) of WT1. This peptide has been shown to be processed and presented by HLA-A0201 to induce cytotoxic $CD8^+$ T cells that are capable of killing WT1-positive tumor cells.

Representative data from a patient with AML after 6 vaccinations with a WT1 RMF peptide are shown in FIG. 2 as evidence that the WT1 peptides are immunogenic in humans. CD3 T cells were stimulated with WT1-A peptide (amino acids 126-134) and cytotoxicity was measured using a standard $^{51}$Cr release assay against 697 (A0201$^+$WT1$^+$) or SKLY-16 (A0201$^+$WT1$^-$) cell lines. The SKLY-16 cells pulsed with WT1-A or irrelevant peptide EW were used as positive and negative controls for the specificity of the killing. Effector: Target (E:T) ratios are indicated on the X-axis. Data demonstrates that T cells killed WT1$^+$ tumor cells in a HLA-A0201-restricted manner.

Well established phage display libraries and screening methods known to those of skill in the art were used to select scFv fragments highly specific for an WT1-A peptide/HLA-A2 complex. In one embodiment, a human scFv antibody phage display library (7×10$^{10}$ clones) was used for the selection of mAb clones. In order to reduce the conformational change of MHC1 complex introduced by immobilizing onto plastic surfaces, a solution panning method was used in place of conventional plate panning. In brief, biotinylated antigens were first mixed with the human scFv phage library, then the antigen-scFv phage antibody complexes were pulled down by streptavidin-conjugated Dynabeads M-280 through a magnetic rack.

Figure 3:
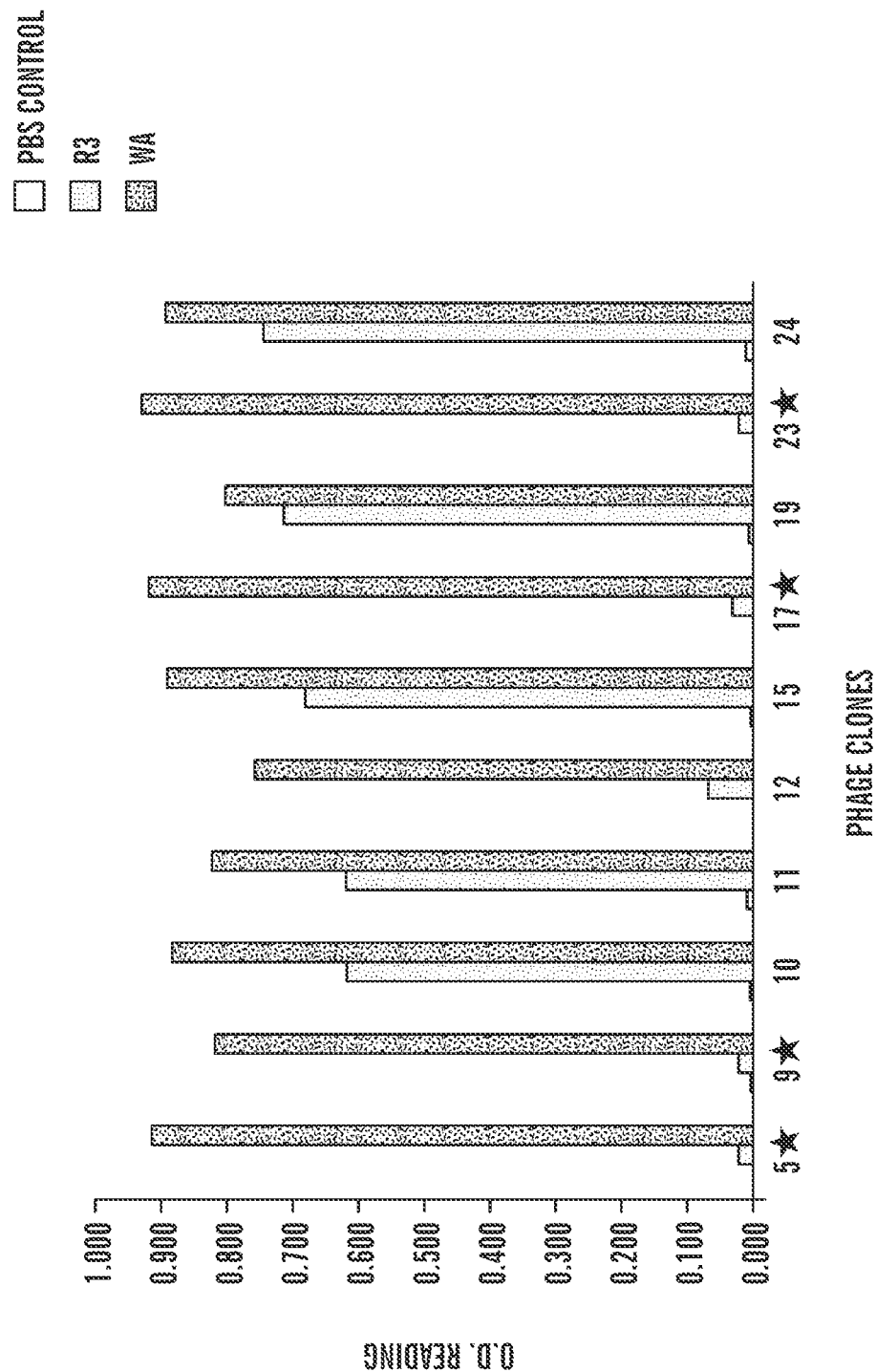
FIG. 3 shows the results of a phage ELISA for specific binding of WT1/A2 (WA) versus PBS control or R3/HLAA0201 (R3).

Bound clones were then eluted and were used to infect *E. Coli* XL1-Blue. The scFv phage clones expressed in the bacteria were purified (35, 36). Panning was performed for 3-4 cycles to enrich scFv phage clones binding to HLA-A0201/WT1 complex specifically. Positive clones were determined by standard ELISA method against biotinylated single chain HLA-A0201/WT1 peptide complexes (FIG. 3). Positive clones were further tested for their binding to HLA-A2/peptide complexes on live cell surfaces by flow cytometry, using a TAP-deficient, HLA-A0201$^+$ cell line, T2. T2 cells were pulsed with peptides (50 µm/ml) in serum-free RPM11640 medium, in the presence of 20 µg/ml 2 M overnight. The cells were washed, and staining was performed as follows.

Figure 4:
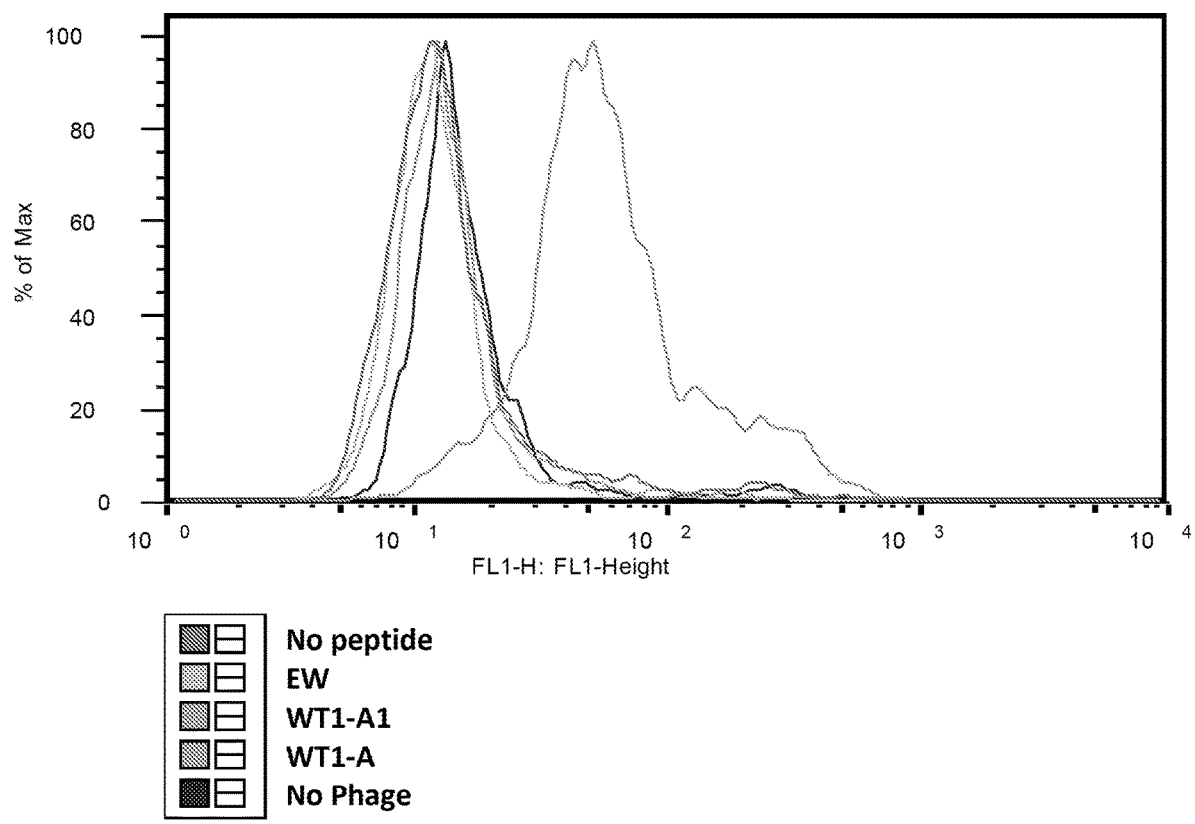
FIG. 4 shows specific binding of only WT1 phage antibodies that bind to T2 cells pulsed with WT1A peptide were selected.

The cells were first stained with purified scFv phage clones, followed by staining with a mouse anti-M13 mAb, and finally, a goat F(ab)2 anti-mouse lg conjugated to FITC. Each step of the staining was done for 30-60 minutes on ice. The cells were washed twice between each staining step. Results are shown in FIG. 4. The phage clone of WT1 ab1 was shown to bind to T2 cells pulsed with only WT1-A peptide (RMFPNAPYL: abbreviated hereinafter as RMF), but not to T2 cells alone, T2 cells pulsed with control EW peptide, or heteroclitic peptide WT1-A.

Figure 5:
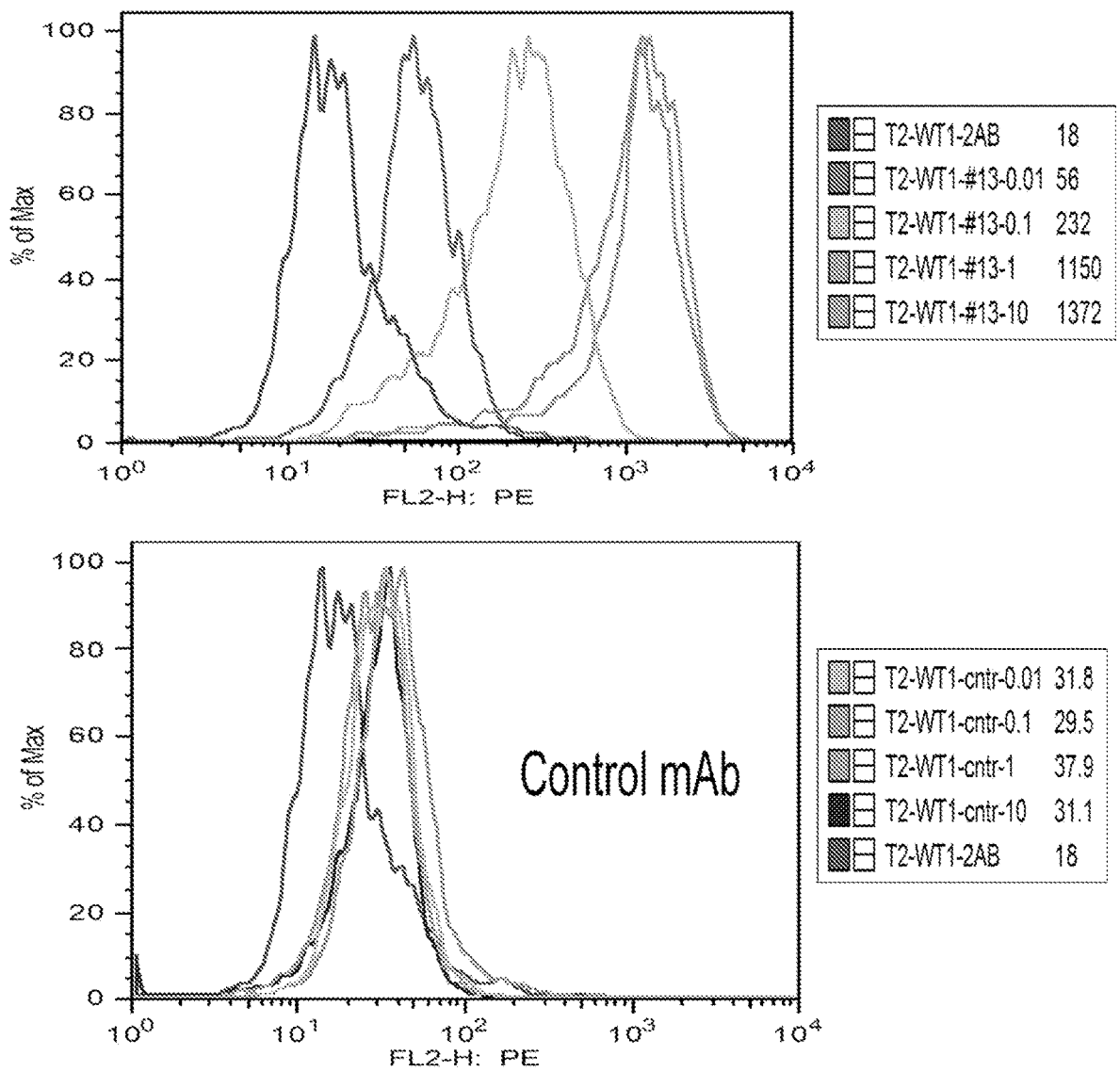
FIG. 5 shows the binding affinity of a full-length IgG1 of a WT1 antibody to RMF/A0201 complex tested by titration of the antibody at various concentrations. Results are shown for T2 cells pulsed with 50 ug/ml RMF (upper panel). Control antibody is shown in the lower panel.

Binding affinity of the full-length lgG1 of WT1 ab1 to the peptide/A0201 complex was tested by titration of WT1 ab1 at indicated concentrations. T2 cells were pulsed with 50 µg/ml or 10 µg/ml, followed by secondary goat F(ab) anti-human lgG/PE. Results are shown in FIG. 5.

FIG. 6 shows the density of peptide/HLA-A0201 complex recognized by WT1 ab. T2 cells were pulsed overnight (ON) with RMF (upper panel) or RHAMM-R3 (lower panel) peptides at indicated concentrations, and binding of WT1 ab1, WT1 ab3 and WT1 ab5 at a concentration of 1 µg/ml was analyzed by flow cytometry.

TABLE 11

Summary of phage panning for WTI/A2

| Phage Libraries | Rounds of Panning | Number of single clones screened | Solution ELISA positive Rate | Number of Unique Clones |
|---|---|---|---|---|
| scFv-spleen A | 4 | 72 | 41/96 | 13 |
| scFv-spleen B | 4 | 47 | 3/47 | 2 |
| scFv-spleen C | 3 | 58 | 0/58 | 0 |

TABLE 11-continued

Summary of phage panning for WTI/A2

| Phage Libraries | Rounds of Panning | Number of single clones screened | Solution ELISA positive Rate | Number of Unique Clones |
|---|---|---|---|---|
| scFv-PBMCA | 4 | 68 | 34/68 | 10 |
| scFv-PBMC B | 3 | 90 | 19/90 | 7 |
| Fab-spleen A | 4 | 12 | 2/12 | 0 |
| Fab-spleen B | 4 | 36 | 0/36 | 0 |
| Fab-spleen C | 4 | 24 | 2/24 | 1 |
| Fab-spleen C | 3 | 72 | 38/72 | 5 |
| Fab-spleen D | 4 | 72 | 4/72 | 1 |
| Fab-spleen D | 4 | 72 | 4/72 | 3 |

The positive scFv clones were tested for their binding to HLA-A2/peptide complexes on live cell surfaces by indirect flow cytometry on: (i) a TAP deficient HLA-A0201+ T2 cells pulsed with WT1 peptide or irrelevant peptide; (ii) a WT1+ HLAA0201+ cell lines such as BV173, U266 and control WTr HLA-A0201+ cell line SKLY16, or WT1+ HLA-A0201-cell line, K562, without pulsing with the peptide. The latter determine the recognition and binding affinity of the scFv to the naturally processed WT1p/A2 complex on tumor cells.

A total of 28 phage clones were screened for their ability to produce mAb specific for the WTI-A peptide/A2 complex. The recognition of the WT1p/A2 complex on live cells was measured by the binding of the phage scFv to T2 cells pulsed with the WTI-A peptide and the other HLA-A2-binding peptides (50 µg/ml). These include: T2 cells alone; T2 cells pulsed with WTI-A peptide; T2 cells pulsed with heteroclitic peptide WT1-A1; T2 cells pulsed with irrelevant EW peptide (HLA-A0201-binding 9-mer peptide, derived from Ewing sarcoma) or RHAMM-R3 (FIG. 4).

TABLE 12

| Clone # | Positive for binding to T2 pulsed with WT1A | Selected for Construction of full-length IgG1 |
|---|---|---|
| 1 | + | |
| 2 | + | |
| 3 | + | + |
| 4 | + | |
| 5 | + | + |
| 6 | + | |
| 7 | | |
| 8 | + | |
| 9 | | |
| 10 | | |
| 11 | | |
| 12 | | |
| 13 | + | + |
| 14 | | |
| 15 | + | + |
| 16 | | |
| 17 | + | |
| 18 | + | + |
| 19 | + | |
| 20 | + | |
| 21 | | |
| 22 | + | |
| 23 | + | + |
| 24-28 | | |

Engineering Full Length mAb Using the Selected ScFv Fragments.

Phage display technology allows for the rapid selection and production of antigen-specific scFv and Fab fragments, which are useful in and of themselves, or which can be further developed to provide complete antibodies, antigen binding proteins or antigen binding fragments thereof. Complete mAbs with Fc domains have a number of advantages over the scFv and Fab antibodies. First, only full length Abs exert immunological function such as CDC and ADCC mediated via Fc domain. Second, bivalent mAbs offer stronger antigen-binding affinity than monomeric Fab Abs. Third, plasma half-life and renal clearance will be different with the Fab and bivalent mAb. The particular features and advantages of each can be matched to the planned effector strategy. Fourth, bivalent mAb may be internalized at different rates than scFv and Fab, altering immune function or carrier function. Alpha emitters, for example, do not need to be internalized to kill the targets, but many drugs and toxins will benefit from internalization of the immune complex. In one embodiment, therefore, once scFv clones specific for WT1p/A2 were obtained from phage display libraries, a full length IgG mAb using the scFv fragments was produced.

Figure 7:
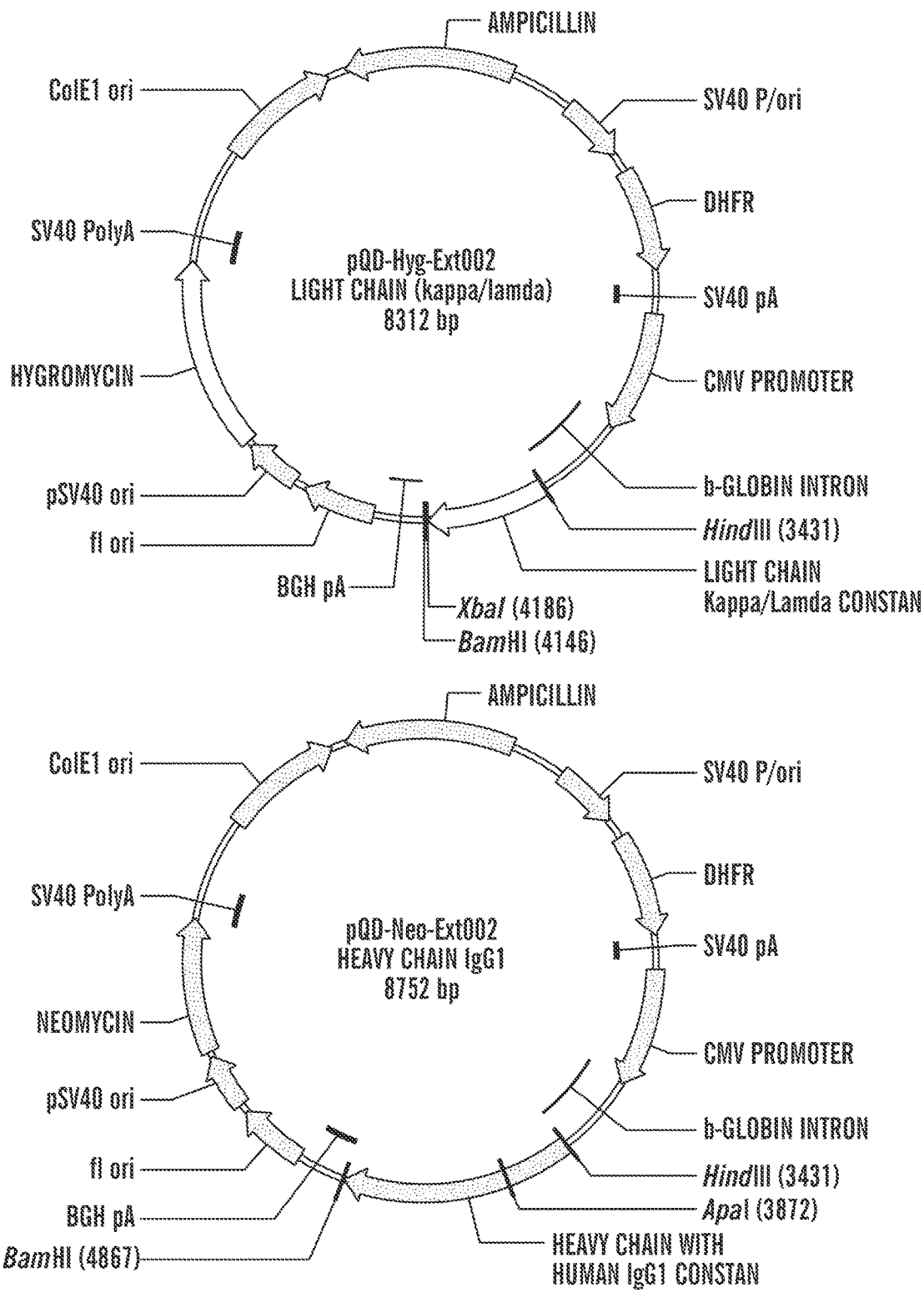
FIG. 7 shows an expression vector for expression of human antibodies.
Figure 8:
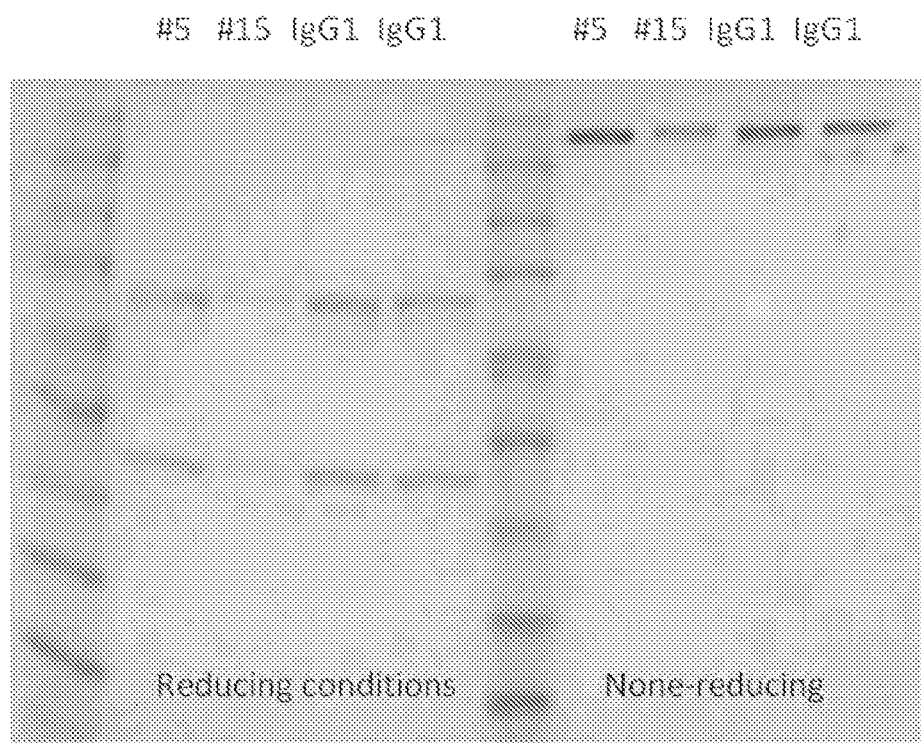
FIG. 8 shows the results of SDS-PAGE analysis of WT1/A2 antibodies under reducing and non-reducing conditions.
Figure 9:
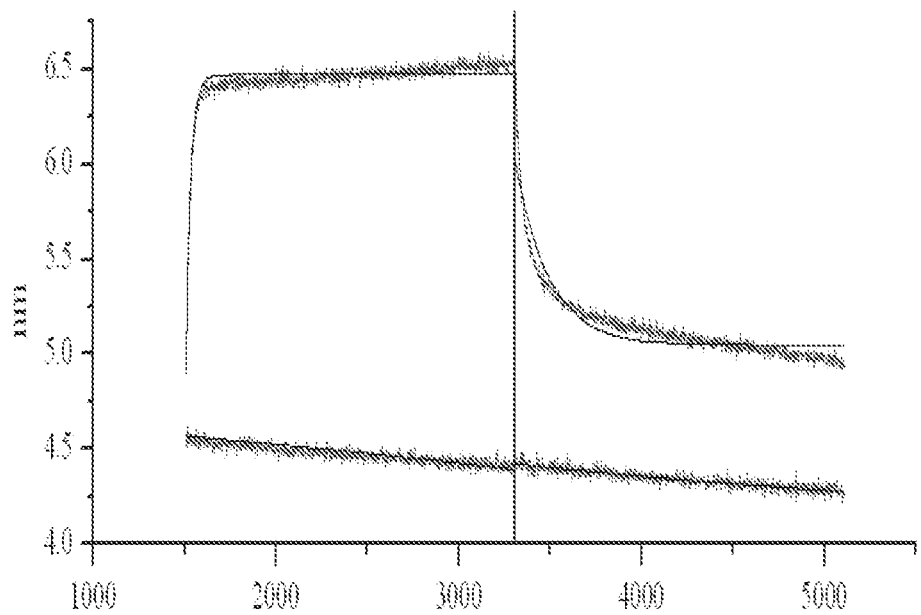
FIG. 9 shows the results of kinetic binding analysis of an WT1/A2 antibody demonstrating affinity of the antibody toward WT1/A2.
Figure 10:
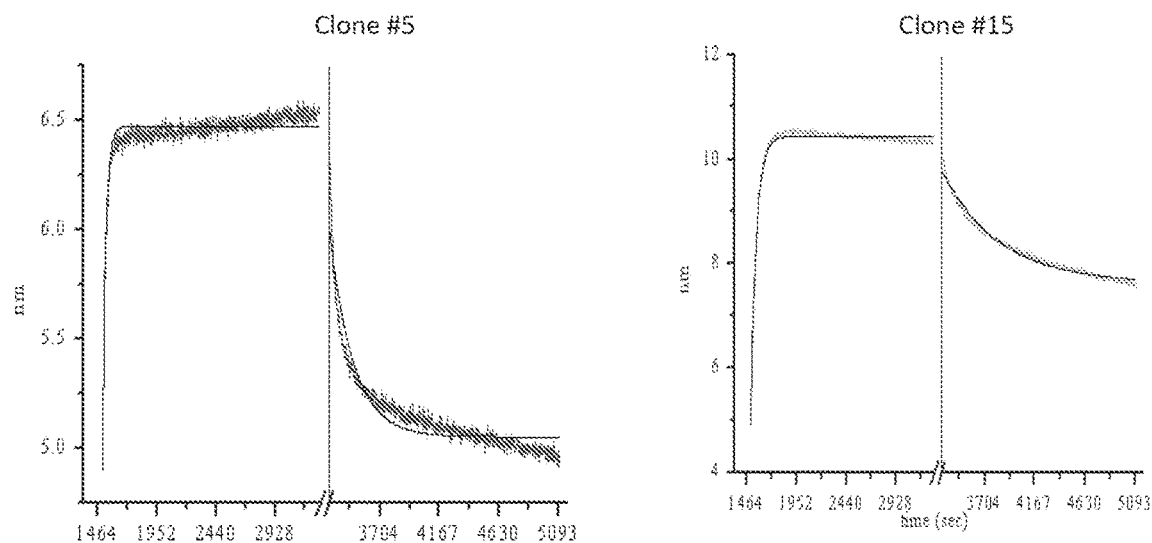
FIG. 10 shows the affinity ($K_D$) of antibody binding to WT1/A2 complex.
Figure 11:
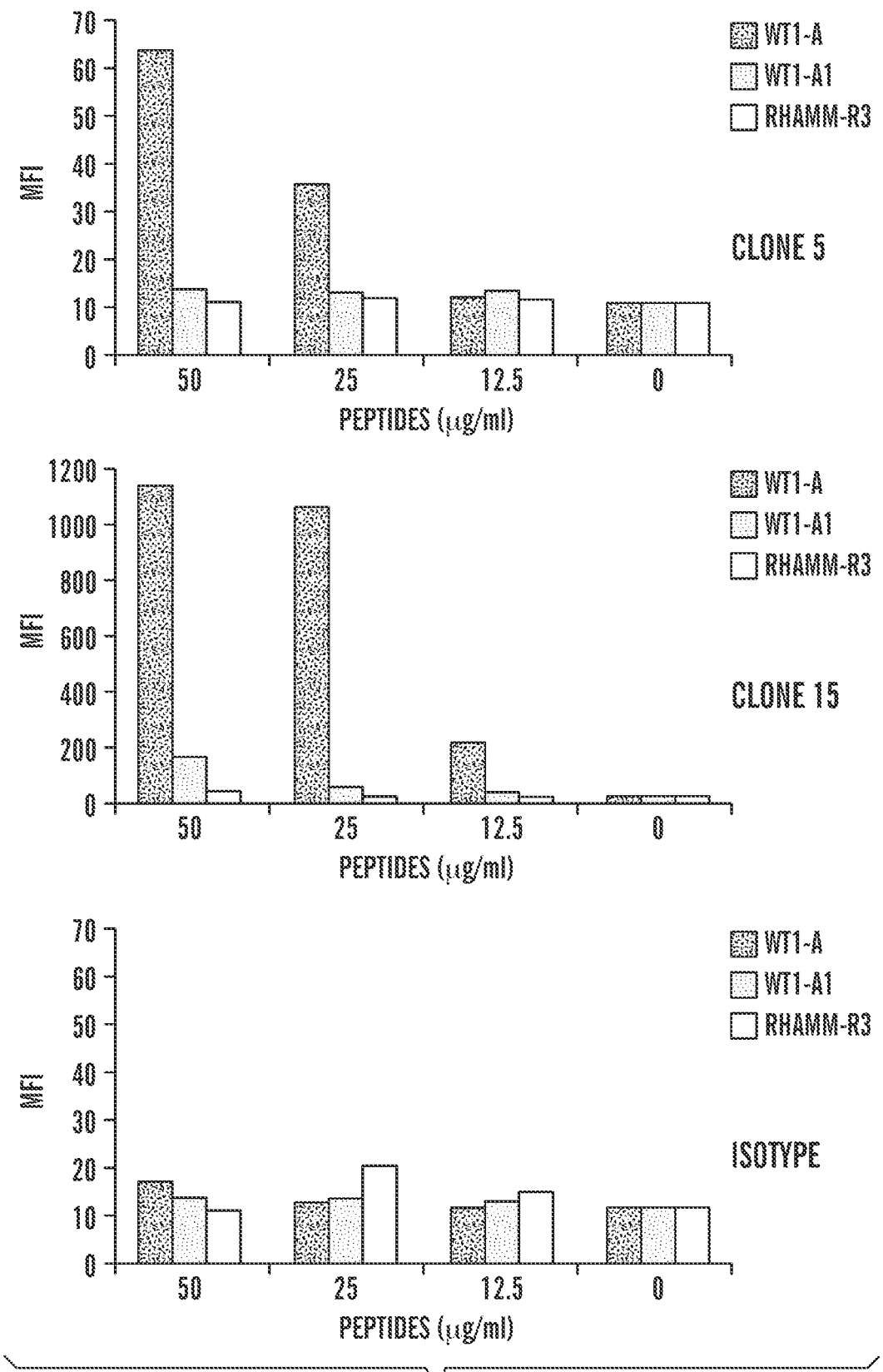
FIG. 11 shows the mean fluorescence intensity (MFI) by flow cytometry of peptide titration on binding of some embodiments, mAb clone 5 (upper panel), clone 15 (middle panel) and control (lower panel) to live T2 cells pulsed with varying concentrations of peptide, WT1-A, WT1-A1 or control.
Figure 12:
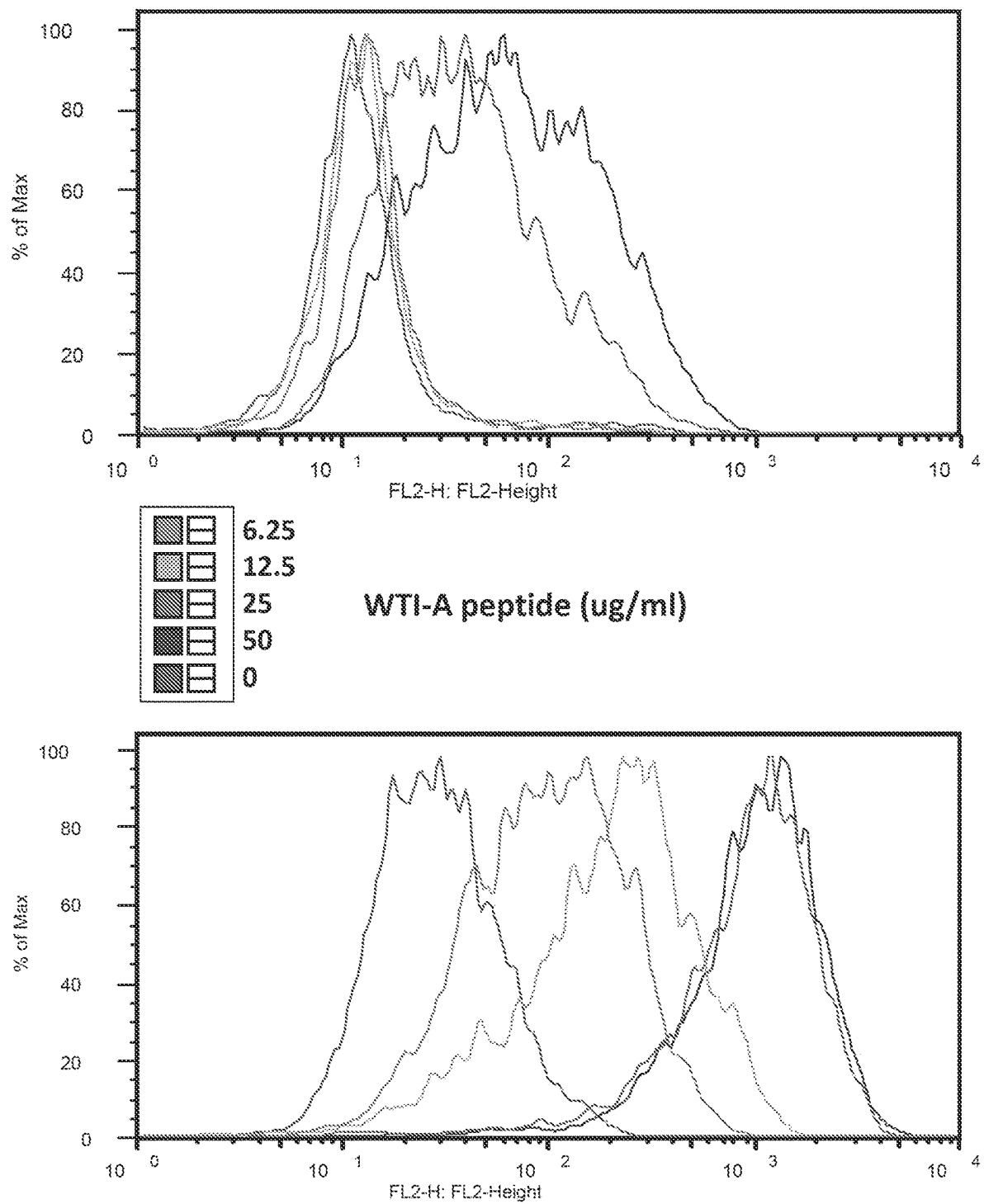
FIG. 12 shows the results of peptide titration on binding of a WT1 antibody, mAb 5 (upper panel), mAb 15 (lower panel) to live T2 cells pulsed with varying concentrations of WT1A peptide.
Figure 13:
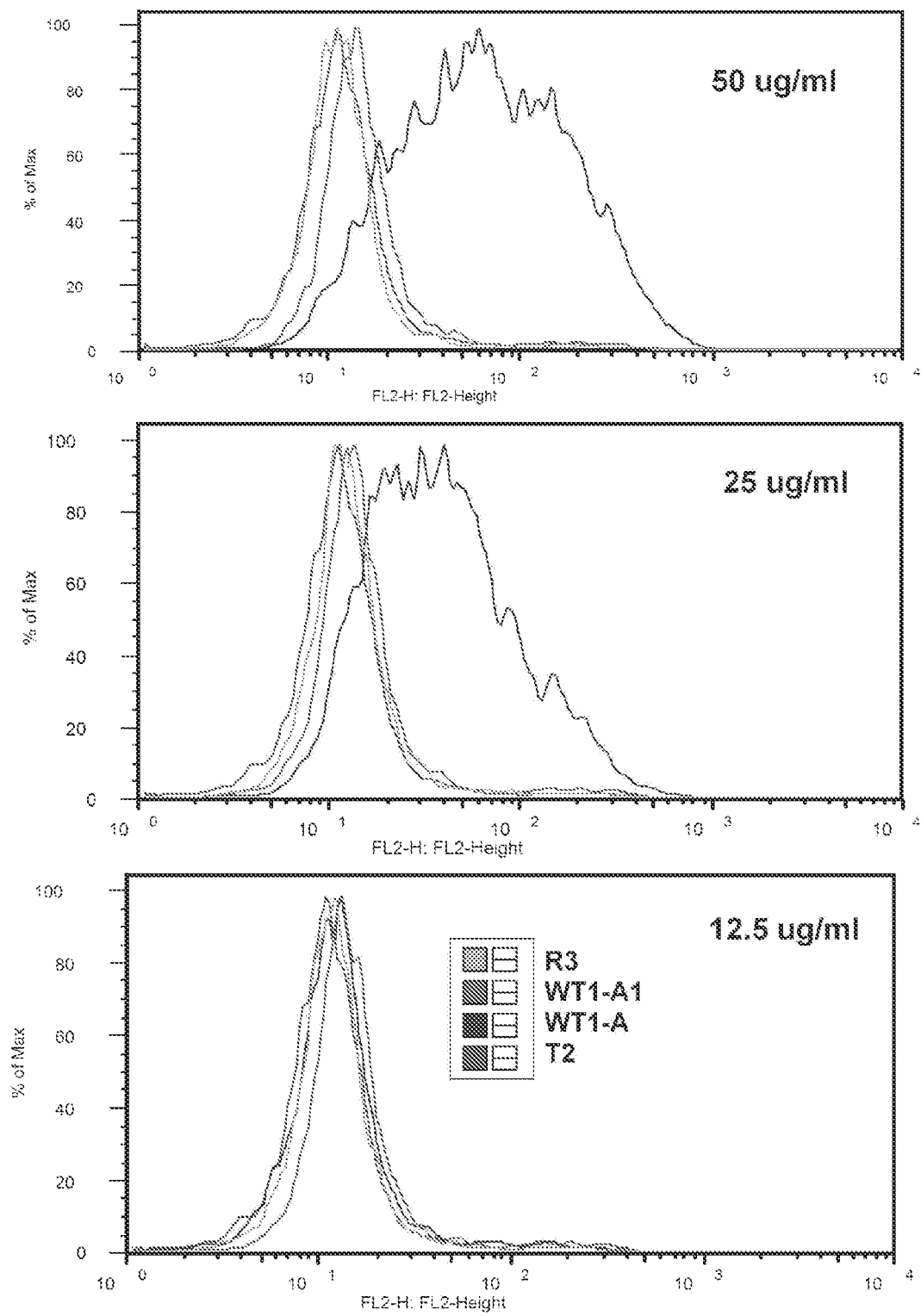
FIG. 13 shows the binding specificity of one embodiment, mAb 5, at different concentrations (50 µg/ml upper; 25 µg/ml middle; and 12.5 µg/ml lower) of peptide (R3, WT1-A1, WT1-A or no peptide.)
Figure 15:
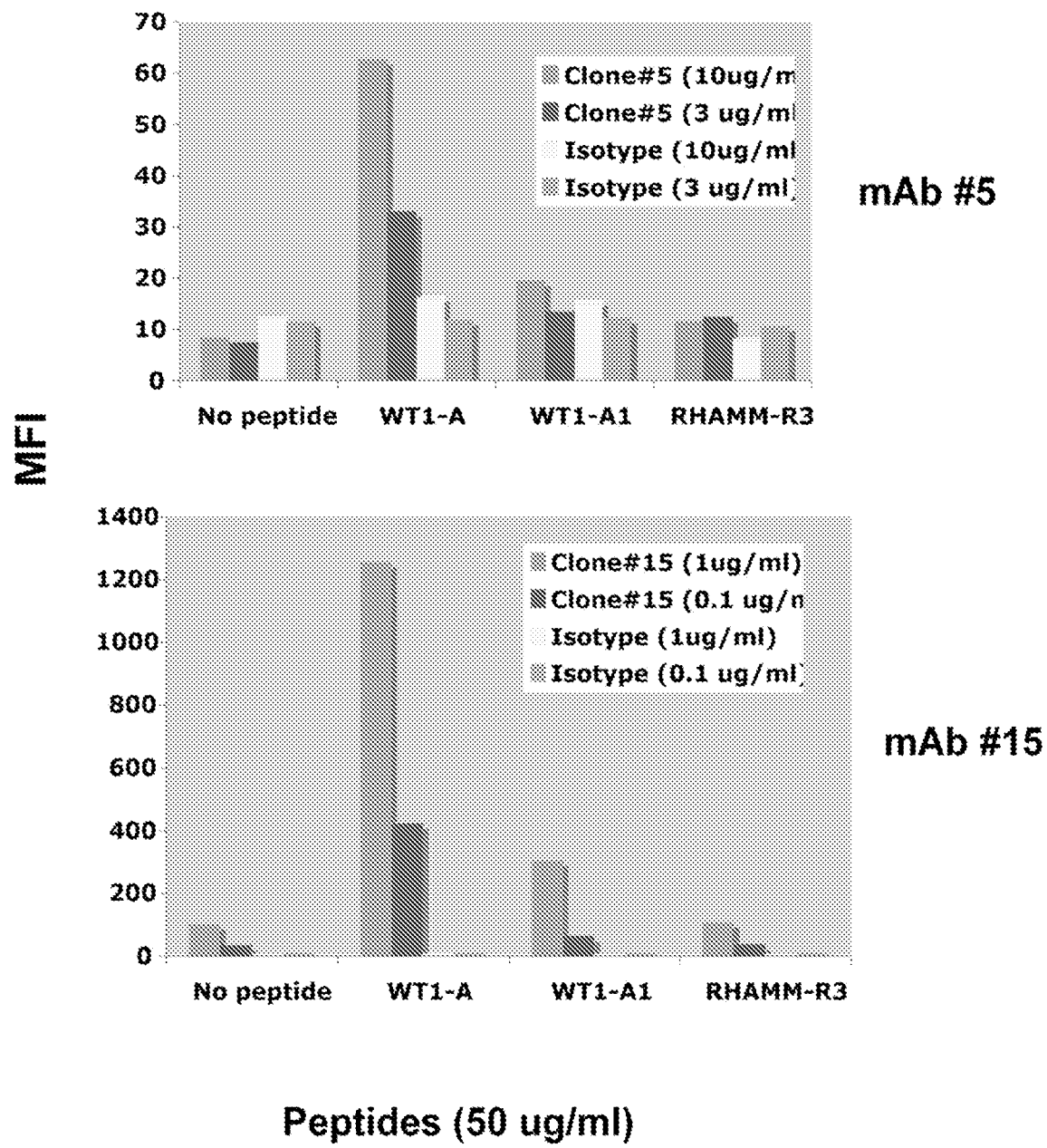
FIG. 15 shows dose-dependent binding of mAbs 5 (upper panel) and 15 (lower panel) to T2 cells pulsed with WT1-A, WT1-A1, or RHAMM-R3 peptide.
Figure 17:
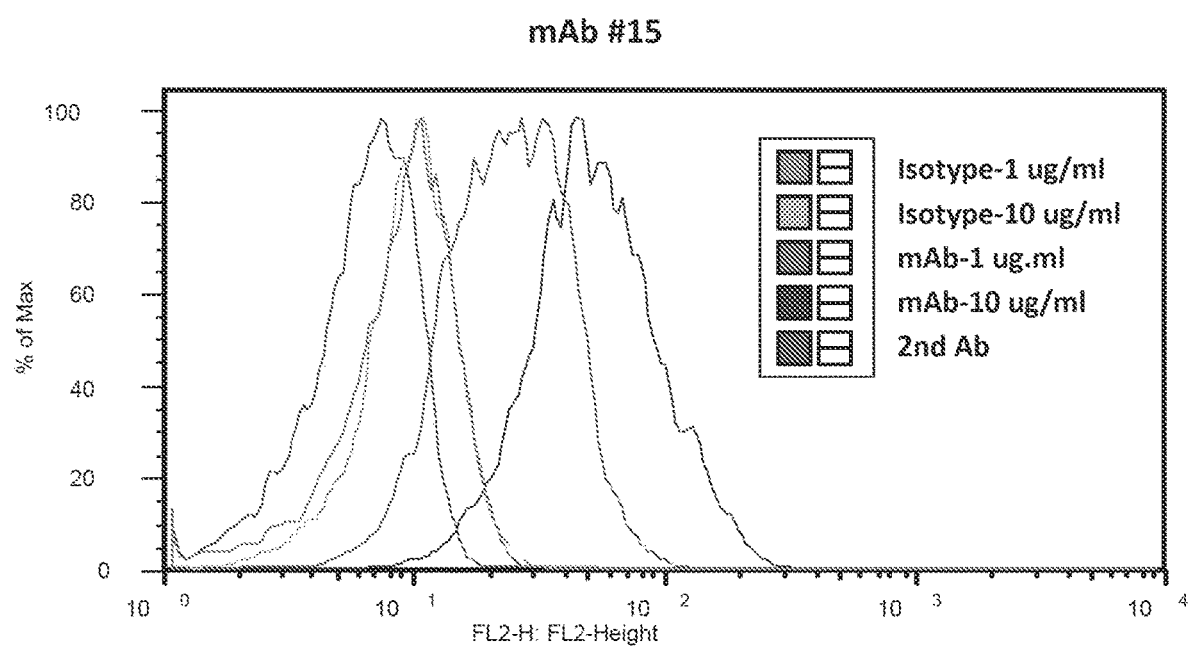
FIG. 17 shows binding of mAb 15 to BV173, a cell line derived from an individual with (Ph1)-positive acute leukemia.
Figure 18:
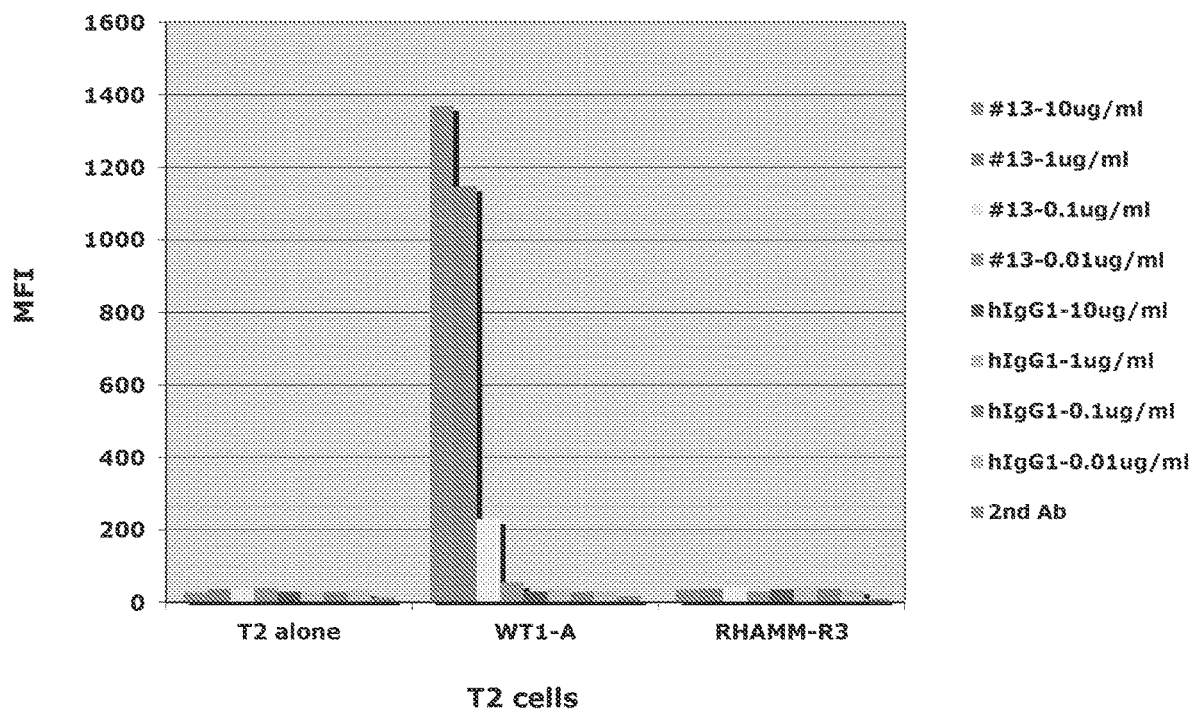
FIG. 18 shows the specific binding of ESK1 (#13) to WT1/A2 complex on the surface of T2 cells pulsed with WT1 peptide.

To produce recombinant human monoclonal IgG in Chinese hamster ovary (CHO) cells, a full length IgG mAb was engineered based on a method known to those of skill in the art (Tomomatsu et al., Production of human monoclonal antibodies against FceRIa by a method combining in vitro immunization with phage display. Biosci Biotechnol Biochem 73(7): 1465-1469 2009). Briefly, antibody variable regions were subcloned into mammalian expression vectors (FIG. 7), with matching Lambda or Kappa light chain constant sequences and IgG1 subclass Fc (for example, see Table 9) (33,34). Purified full length IgG antibodies showed expected molecular weight under both reducing and non-reducing conditions (FIG. 8). Kinetic binding analysis (35) confirmed specific binding of full length IgG to WT1/A2, with a KD in nanomolar range (FIGS. 9 and 10.)

Example 1

Selection of ScFv Specific for WT1p/A2 Complex Using a Fully Human Phage Display Library.

Phage display against HLA-A0201/WT1 peptide complex was performed for 3-4 panning rounds to enrich the scFv phage clones binding to HLA-A0201/WT1 peptide complex specifically. Individual scFv phage clones positive for the WT1 peptide/A2 complex were determined by ELISA and the clones that possessed unique DNA coding sequences were subjected to further characterization. To test if the ScFv bound to the WT1p/A2 complex on live cells, the positive phage clones were tested for binding to a TAP deficient, HLA-A0201-positive cell line, T2. T2 cells can only present the exogenous peptides and therefore have been widely used for detection of specific epitopes presented by HLA-A2 molecules. A total 35 phage clones were screened on T2 cells and 15 clones showed specific binding to T2 cells pulsed with only WT1 RMF peptide, but not to T2 cells alone or pulsed with control RHAMM-3 peptide (FIG. 4). The scFv phage clones were unable to bind to several tumor cell lines that are WT1– and HLA-A2 positive suggesting the affinity of the ScFv was weak, compared to full-length bivalent mAb.

Example 2

Generation of Full-Length Human IgG1.

Immunological function such as CDC and ADCC depend on the Fc domain of bivalent IgG. In addition, bivalent mAbs offer stronger antigen-binding avidity than monomeric scFv Abs. Therefore, 6 ScFv phage clones among 15 positive phage clones were selected to produce the full-length human monoclonal IgG1 in HEK293 and Chinese hamster ovary (CHO) cells. In brief, variable regions of the mAbs were subcloned into mammalian expression vectors with matching human lambda or kappa light chain constant region and human IgG1 constant region sequences. Purified full length IgG antibodies showed expected molecular weight under both reducing and non-reducing conditions (FIG. 8). Five clones were successfully engineered into human IgG1.

Example 3

Specificity and Binding Avidity of the IgG1 mAb Binding to Human Cell Lines.

T2 cells, pulsed with or without RMF or RHAMM-3 peptides initially were used to determine the binding specificity of the mAb. Three out of five human IgG1, including WT1 ab1, showed specific binding to the T2 cells that were pulsed only with WT1 peptide, but not to T2 alone or T2 pulsed with control peptide RHAMM-R3. The binding avidity of the mAb were substantially enhanced (50 to 100 fold), compared to their parental scFv phage clones. Two mAbs among the five showed binding to T2 cells alone or pulsed with the control peptide RHAMM-R3, although the binding was greatly enhanced by pulsing the cells with RMF peptide. This suggested that these two mAb also had high avidity for epitopes on the HLA-A2 molecule alone and therefore were excluded from further investigation. This was not unexpected, as it has been a common problem for producing such mAb against peptide/MHC complexes, given the predominance of the MHC class I molecule epitopes within the complexes. It also suggests that the precise specificity of the mAb for the complexes might not be determined easily at the scFv stage, due to the lower affinity compared to the bivalent IgG1 mAb.

The binding affinity of the three remaining mAb specific for the WT1p/A2 complex first was investigated on T2 cells pulsed with or without RMF and control RHAMM-R3 peptides (50 ug/ml) by titration of the mAbs. Mab WT1 ab1 showed the strongest binding, down to a concentration of 0.01 ug/ml. Isotype control human IgG1 showed no binding at any concentrations tested (FIG. 5). In addition to WT1 ab1, the two other mAb, WT1 ab3 and WT1 ab5, showed specific binding at a range of <1 ug/ml of the mAb concentrations used. The specific recognition of the mAb also depended on the antigenic density on the cell surface. T2 cells were pulsed with RMF or R3 peptides at 50, 25, 12.5, 6.25, 3.13 and 1.6 ug/ml; the test mAb were used at 1 ug/ml for the T2 binding assay. WT1 ab1 could detect the RMF peptide/A2 complex on T2 cells in a concentration-dependent manner at concentrations as low as 1.6 ug/ml, with significantly higher fluorescence intensity than the other 2 mAb (FIG. 6). These results further confirmed that the WT1 ab1 possessed the highest avidity for the RMFp/A0201 complex.

Example 4

Epitope Mapping.

Figure 19:
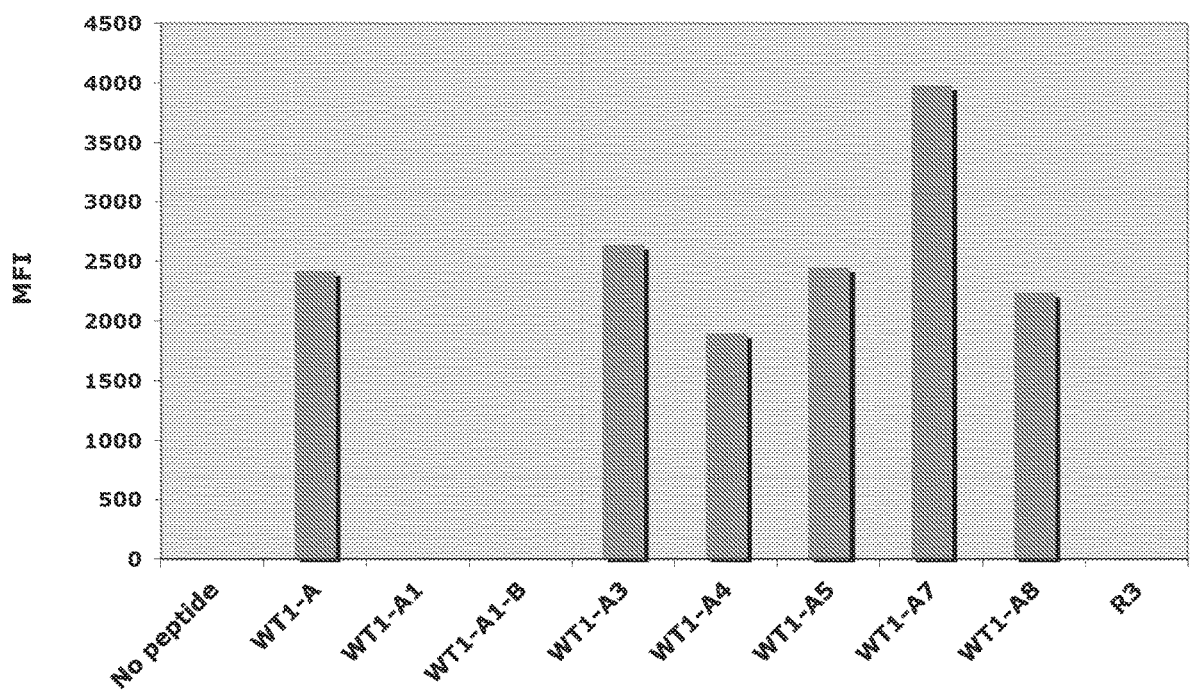
FIG. 19 and FIG. 20 show that WT1 antibody is able to recognize RMF peptide in which substitution of different positions of the RMF peptide with alanine is made (see also Table 10) and that the loss of binding seen with substitution of position 1 by either alanine (WT1-A1-B) or tyrosine (WT1-A1), was not due to the reduction of peptide binding affinity to the HLA-A2 molecule, as both peptides showed the strongest binding in T2 stabilization assay using the mAb specific for the HLA-A2 molecule, clone BB7.
Figure 20:
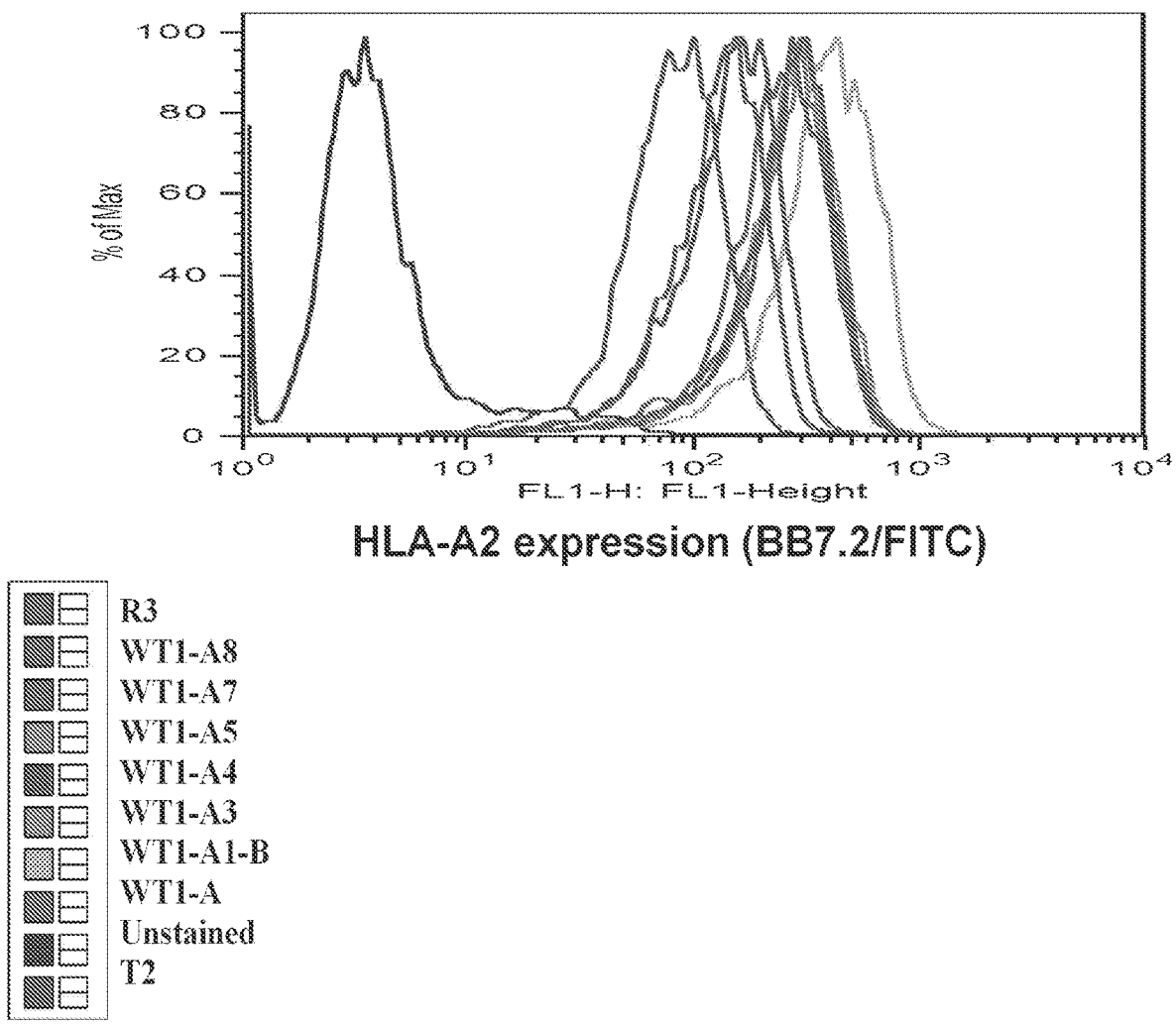

To investigate with more precision the epitope for WT1 ab1 recognition, RMF peptides were substituted at positions 1, 3, 4, 5, 6, 7 and 8 with alanine and pulsed onto T2 cells and were tested for binding of WT1 ab1. Positions 2 and 9 of the RMF were left intact, as these are the anchor residues for peptide binding to the HLA-A0201 molecule. Except for position 1, alanine substitutions at other positions did not greatly affect the binding of the WT1 ab1, as compared to the native RMF peptide (FIG. 19). However, substitution of position 1 by either alanine (WT1-A1-B) or tyrosine (WT1-A1), completely abrogated the binding of WT1 ab1. The loss of binding was not due to the reduction of peptide binding affinity to the HLA-A2 molecule, as both peptides showed the strongest binding in T2 stabilization assay using the mAb specific for the HLA-A2 molecule, clone BB7 (FIG. 20). These results show that the arginine at position 1 of the RMF peptide is one of the most crucial for the WT1 ab1 recognition. The role of the residues at positions #2 and 9, could not be assessed.

The next important question was whether WT1 ab1 was able to recognize naturally processed WT1 epitope RMF presented by HLA-A0201 molecules on the cell surface. A panel of cell lines was selected based on the expression of WT1 mRNA and HLA genotyping (Table 12).

TABLE 12

| | HLA-A2 genotype | WT1 mRNA | WT1 AB binding | Ratio of BB7.2: Isotype |
|---|---|---|---|---|
| Mesothelioma/solid tumor | | | | |
| JMN | + | + | + | 248 |
| Meso 37 | + | + | + | 68 |
| Meso 47 | + (02xx) | + | + | 17 |
| H2452 | + | + | + | 20 |
| Meso34 | + | + | + | 37.3 |
| Meso-56 | + (02xx) | + | + | 23 |
| H2373 | + | + | − | 1.6 |
| MSTO | − | + | − | 1.4 |
| VAMT | − | 3+ | − | NT |
| Mewo | + | − | − | 3 |
| Leukemias and other hematopoietic cell lines | | | | |
| BV173 | + | ++ | + | 196 |
| BA25 | + | ? | + | 117.5 |
| ALL-3 | + | + | + | 60 |
| U266 | + | + | − | 1.8 |
| 697 | + | 5+ | − | 4.1 |
| LAMA | + | 2+ | − | 6 |
| SKLY-16 | + | − | − | 1.9 |
| HL-60 | − | 3+ | − | 0.4 |
| K562 | − | 2+ | − | 1.5 |
| T2 | + | NT | − | >20 |

WT1 mRNA expression level was estimated according to a previous study (Rena), by quantitative RT-PCR.

Figure 21:
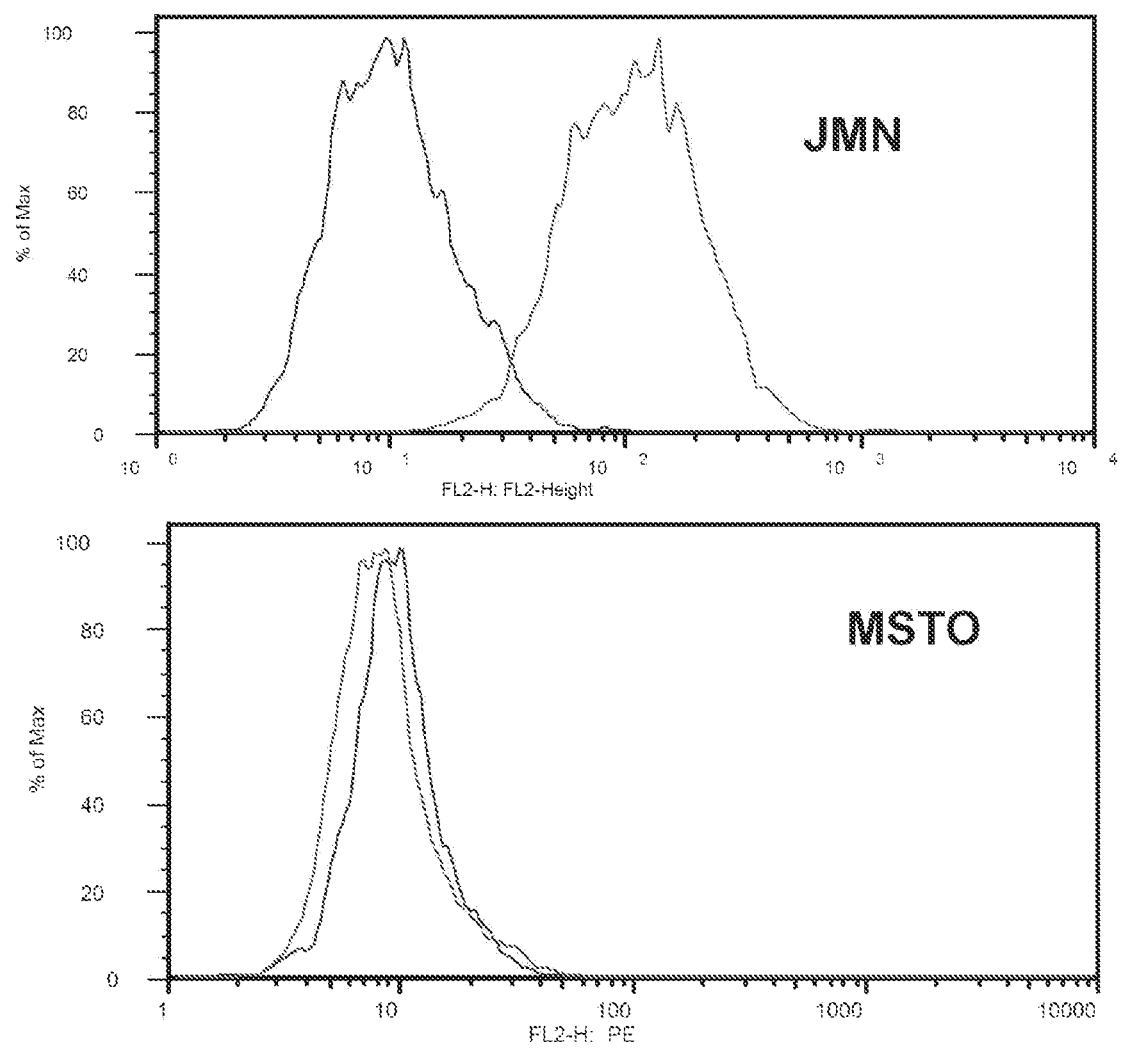
FIG. 21 shows recognition by WT1 antibody of naturally presented RMF/HLA-A0201 complex on the cell surface of human mesothelioma cell lines, JMN (WT1$^+$/A0201$^+$) but not MSTO (WT1$^+$/HLA-A0201$^-$).

Among 7 human mesothelioma cell lines that are positive for both HLA-A0201 and WT1 mRNA, WT1 ab1 bound to 6 out of 7 cell lines, but not to the cells that were either HLA-A0201 negative (MSTO and VAMT) or WT1 mRNA negative, such as melanoma cell line, Mewo (FIG. 21).

Figure 22:
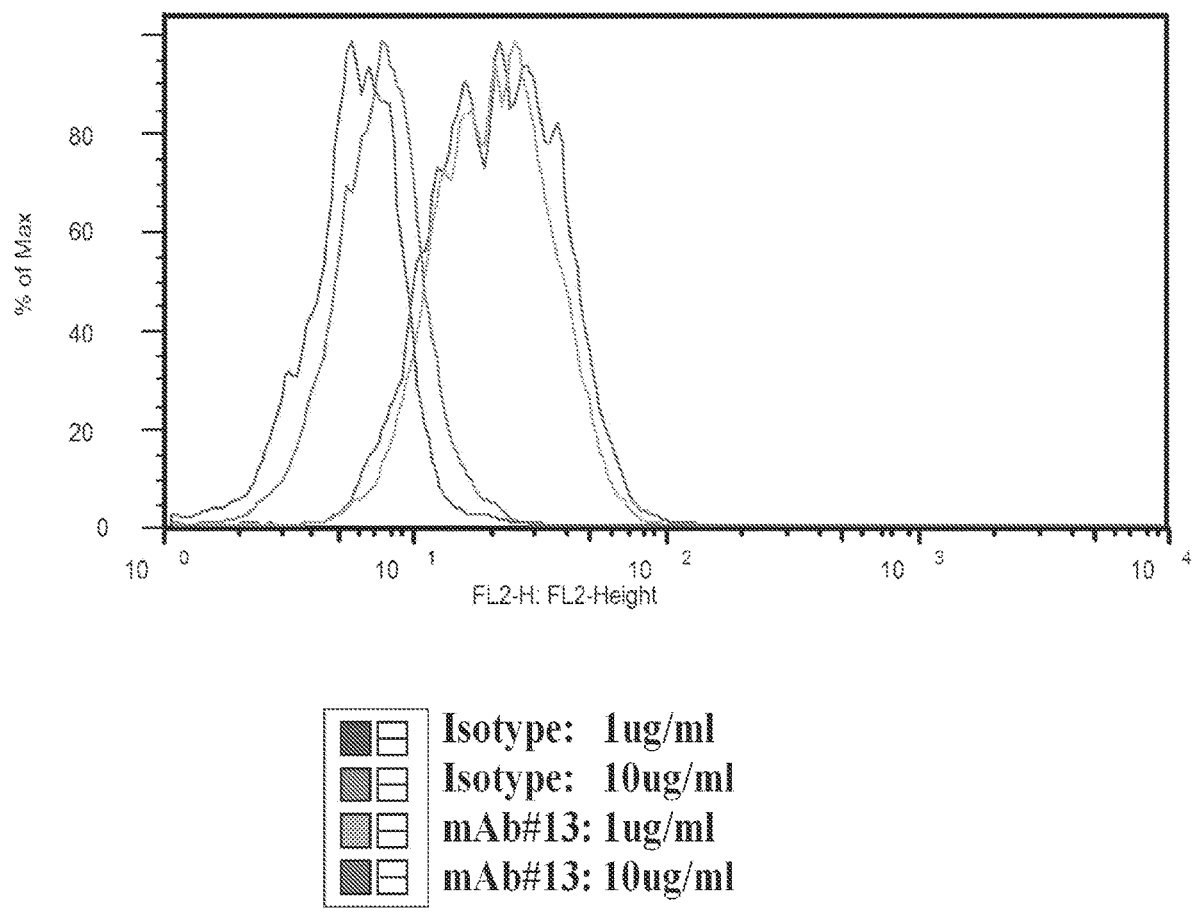
FIG. 22 shows binding of WT1 antibodies to human CML-derived cell line BV173.

Similarly, among 9 leukemia cell lines tested, WT1 ab1 bound to 3 cell lines BV173 (FIG. 22), BA25 and ALL-3, that are positive for both WT1 mRNA and HLA-A0201, but not to HLA-A2-negative cell lines HL60 and K562, that have been demonstrated to express a high level of WT1 transcripts in numerous studies.

As expected, intensity of binding of the WT1 AB1 also appeared to be directly associated with the expression level of HLA-A0201 molecule, as shown in mesothelioma cells H2373, leukemia cell lines 697 and LAMA, and myeloma cell line U266. Although these cell lines were positive for both WT1 transcripts and HLA-A2, the expression level of the HLA-A2 was low (Table 12) and the mAb did not show binding. On the other hand, the results obtained with T2 cells argue against the possibility of WT1 ab1 binding to HLA-A0201 alone as T2 cells expressed a high level of HLA-A2 molecule. Notably, WT1 ab1 did not bind to T2 cells alone or pulsed with R3 and other HLA-A0201-binding peptides such as Ewing sarcoma-derived (EW) or the heteroclitic peptide for the RMF peptide, WT1-A1; these two peptides have been shown to have higher affinity for the HLA-A0201 molecule in T2 stabilization assay (28). These results provided strong evidences that WT1 ab1 recognition was specific for epitopes jointly composed of the RMF peptide and the A0201 molecule in a complex. The binding of the other two mAb, WT1 ab3 and WT1 ab5, to the BV173 and JMN cells was also weaker than WT1 ab1.

Example 5

Quantitation of WT1 ab1 Binding Sites on Cells.

Figure 23:
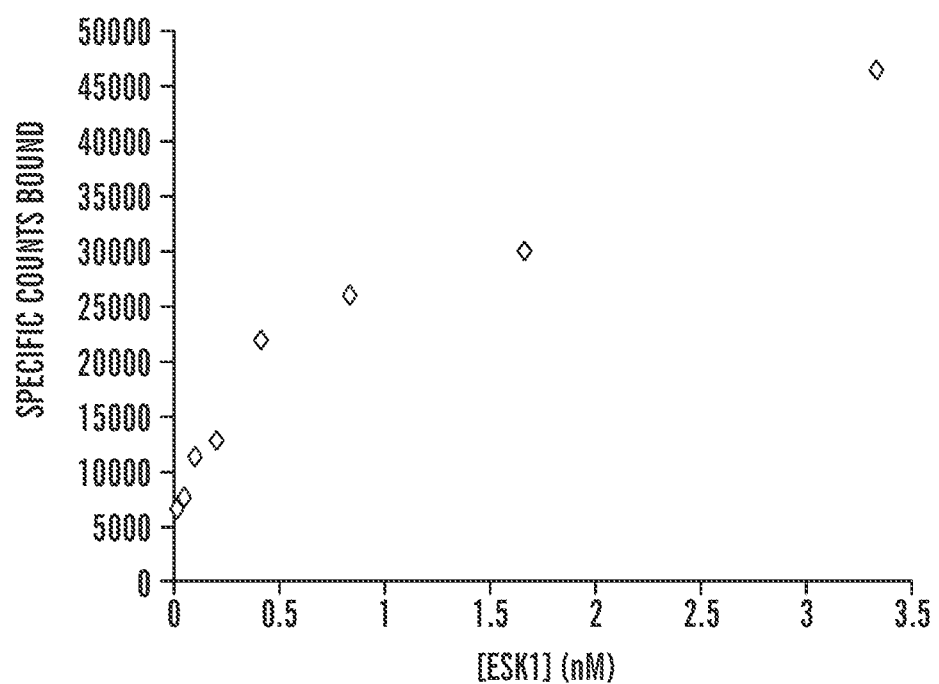
FIG. 23 is a Scatchard analysis based on binding of WT1 antibody to JMN cells and shows an avidity constant of about 0.2 nM.
Figure 24:
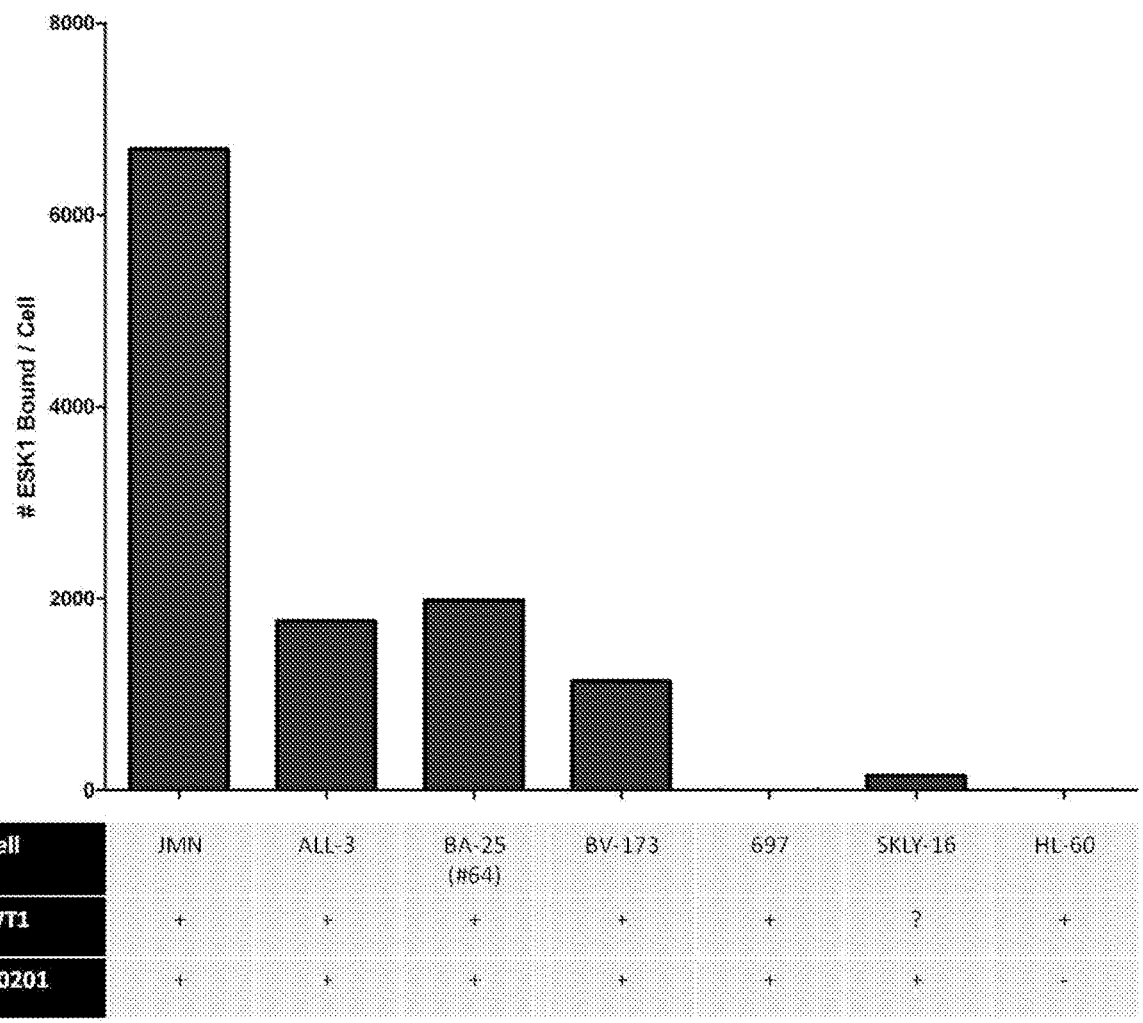
FIG. 24 shows WT1 antibody binding to a panel of mesothelioma and leukemia cells.

A radioimmunoassay using 125I-labeled WT1 ab1 was used to confirm the specificity of the antibody for WT1$^+$ HLA-A0201$^+$ cell lines, to determine an affinity constant and to assess the number of antibody binding sites per cell on a panel of cell lines. Scatchard analysis based on binding to JMN cells showed an avidity constant of about 0.2 nM (FIG. 23). This number was confirmed by interferometry using a Forte Bio device. 125-I-labeled WT1 ab1 was used to confirm the specificity of the antibody for WT1$^+$ HLA-A0201$^+$ cell lines, and to assess the number of antibody binding sites on a panel of cell lines (FIG. 24). Because we cannot determine whether the bivalent mAb is binding to 1 or 2 complexes on the surface, total epitopes per cell could be as high as twice the number of mAb binding sites. Again, WT1 ab1 bound to JMN, ALL-3, BA25, BV173, which are positive for both HLA-A0201 and WT1 mRNA, but not HLA-A0201 negative (HL60) or WT1 mRNA negative (SKLY-16) cells. WT1 ab1 did not bind to 697 cells, which are both HLA-A0201 and WT1 positive, but contain low levels of HLA-A0201 (Table 12), confirming that a certain level of total MHC complex is needed to present sufficient WT1 peptide for WT1 ab1 binding. T2 pulsed with RMF bound the highest number of mAb (50,000 per cell), followed by JMN cells which bound ~$6 \times 10^3$ WT1 ab1 molecules per cell, translating to between $6 \times 10^3$ and $1.2 \times 10^4$ RMFpeptide/A2 complexes per cell assuming monovalent or bivalent antibody binding, respectively. The three positive leukemia cell lines bound between $1 \times 10^3$ and $2 \times 10^3$ WT1 ab1 molecules, or $2 \times 10^3$-$4 \times 10^3$ binding sites (FIG. 24). These results were confirmed by quantitative flow cytometry.

Example 6

WT1 Ab 1 Binding to Leukemic Patient Samples.

Figure 25:
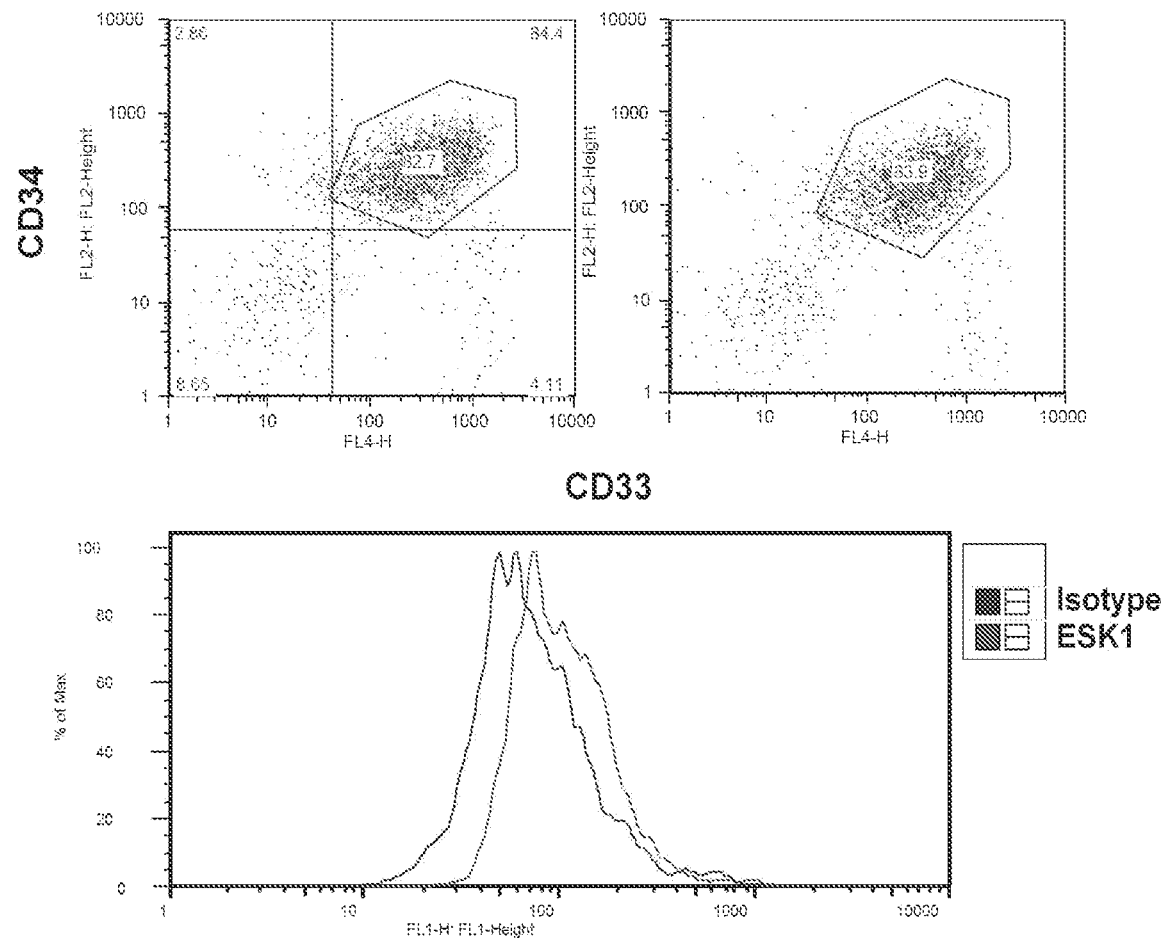
FIG. 25 shows the results of flow cytometric analyses gated on CD33 and CD34 double positive AML blast cells from an HLA-A2 positive patient. ESK1 binds to the leukemia blasts.

We next investigated if WT1 ab1 is able to detect the RMF epitope on primary AML cells. Radioimmunoassay showed significant binding of the WT1 AB1 to AML blasts of patient 1, who is HLA-A2 positive and WT1 mRNA$^+$. WT1 ab1 bound to CD33$^+$ and CD34$^+$ double positive cells that account for more than 83% of the whole cell populations (FIG. 25). WT1 ab1 did not bind to the cells of 3 other patients who are either HLA-A2 positive but mRNA negative or HLA-A2 negative. WT1 ab1 did not bind to PBMCs from either HLA-A2 positive or negative healthy donors. The results were confirmed by flow cytometry analysis. WT1 AB1 did not show significant binding to the blasts from the patients who were A0201 negative (FIG. 26). The results were consistent with the results obtained with mRNA expression of the cells. These data confirm that the level of RMFp/HLA-A0201 on the surface of leukemia cells is adequate to allow reactivity with the WT1 ab1 and the levels on WT1 negative healthy cells is not significant.

Example 7

WT1 AB1 Mediates ADCC Against Tumor Cells

Figure 27:
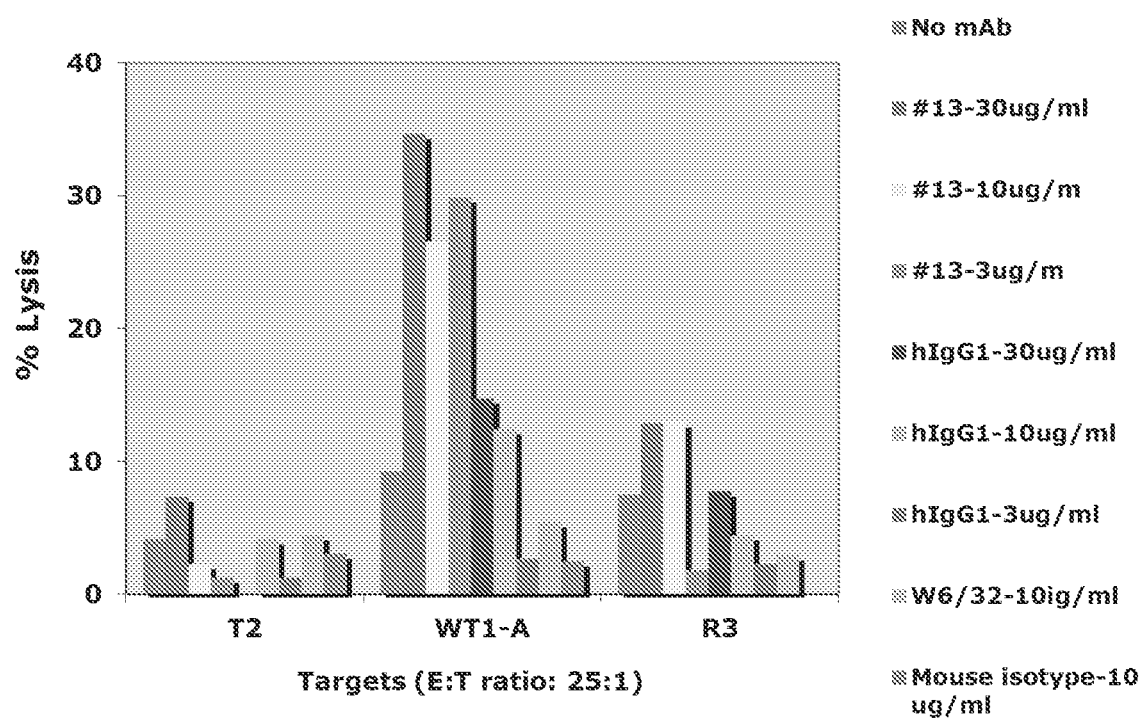
FIG. 27 shows WT1 mAb ESK1 mediated ADCC against T2 cells pulsed with RMF peptide.
Figure 28:
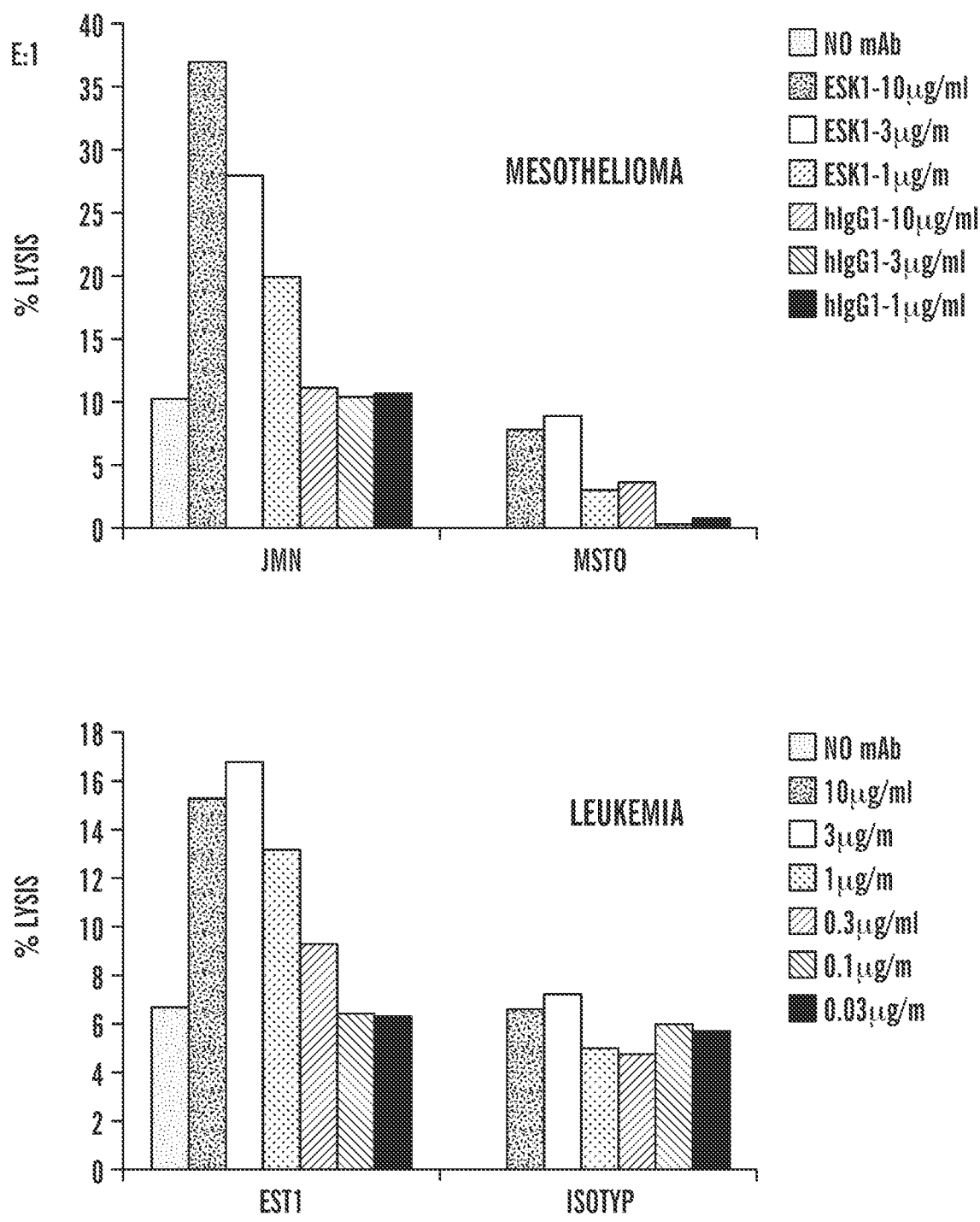
FIG. 28 shows the ability of WT1 antibody to mediate ADCC with human effectors in JMN and leukemia cell line BV173 (lower panel) but not MSTO cells.
Figure 29:
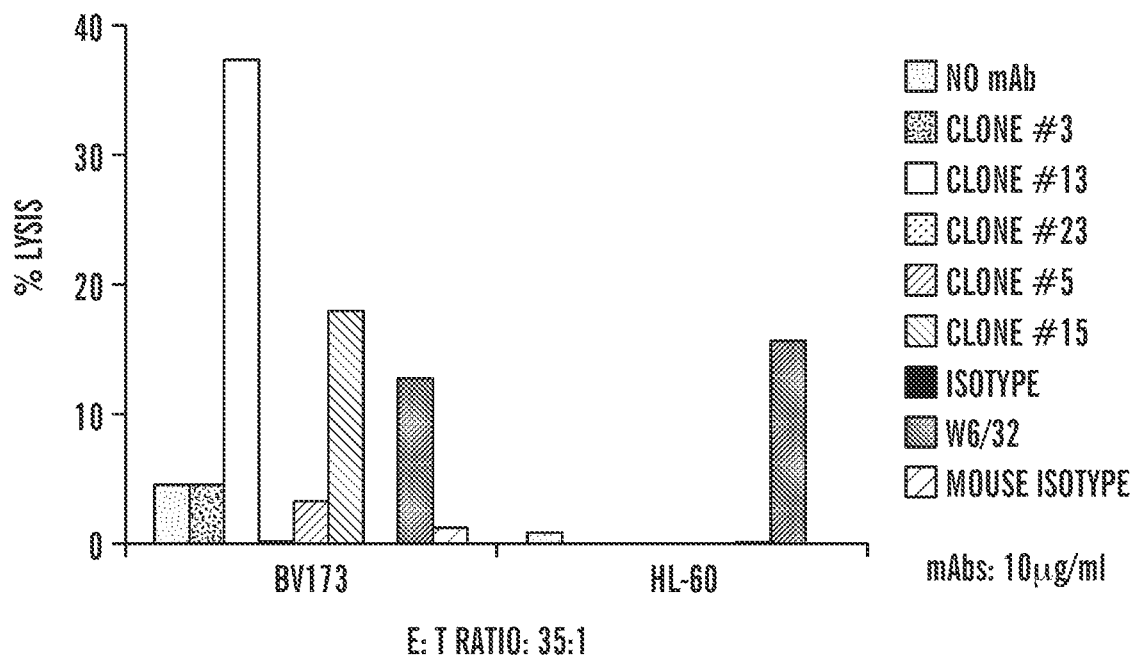
FIG. 29 shows that WT1 mAbs are effective against human leukemia cell line BV173 but not HL60 cells, which are not HLA-A2$^+$.
Figure 30:
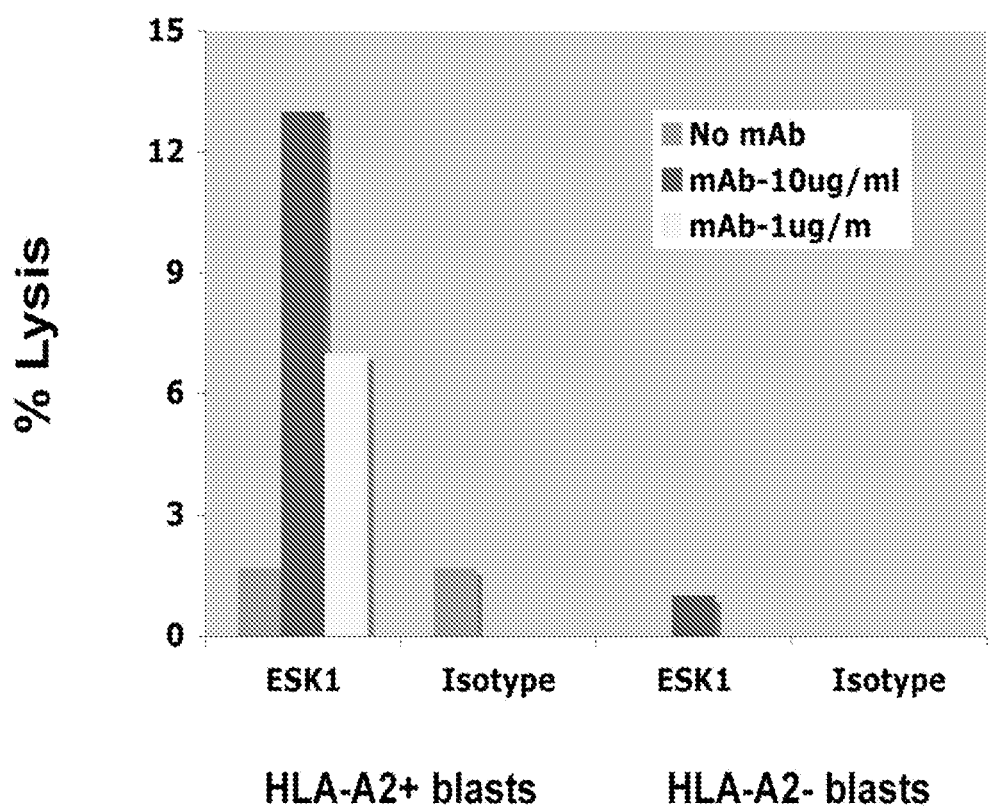
FIG. 30 shows that WT1 antibody induces ADCC against primary AML blasts from an HLA-A2 positive patient.

ADCC is considered to be one of the major effector mechanisms of therapeutic mAb in humans. In the presence of human PBMC, WT1 ab1 mediated dose-dependent PBMC ADCC against the T2 cells loaded with RMF peptide, but not T2 cells alone or T2 cells pulsed with control R3 peptide (FIG. 27). Importantly, WT1 ab1 was able to mediate ADCC against naturally presented RMF epitope by HLA-A0201 molecule on tumor cells, such as the mesothelioma cell line, JMN (FIG. 33), and the leukemia cell line BV173 (FIG. 34), but not the HLA-A2 negative cells MSTO (FIG. 28) or HL-60 (FIG. 29). The killing was consistently observed at 1 μg/ml or below of WT1 ab1 using PBMCs as effector cells from multiple healthy donors. Importantly, WT1 ab1 also killed primary A0201-positive AML blasts that were positive for the WT1 ab1 binding, but not the blasts that were HLA-A0201 negative (FIG. 30). These results demonstrated that WT1 ab1 mediates specific ADCC against cells that naturally express RMF and HLA-A0201 complex at physiologic levels as well as on cell lines.

Example 8

WT1 AB1 Eliminates Human Leukemia Cells in NSG Mice

Figure 31:
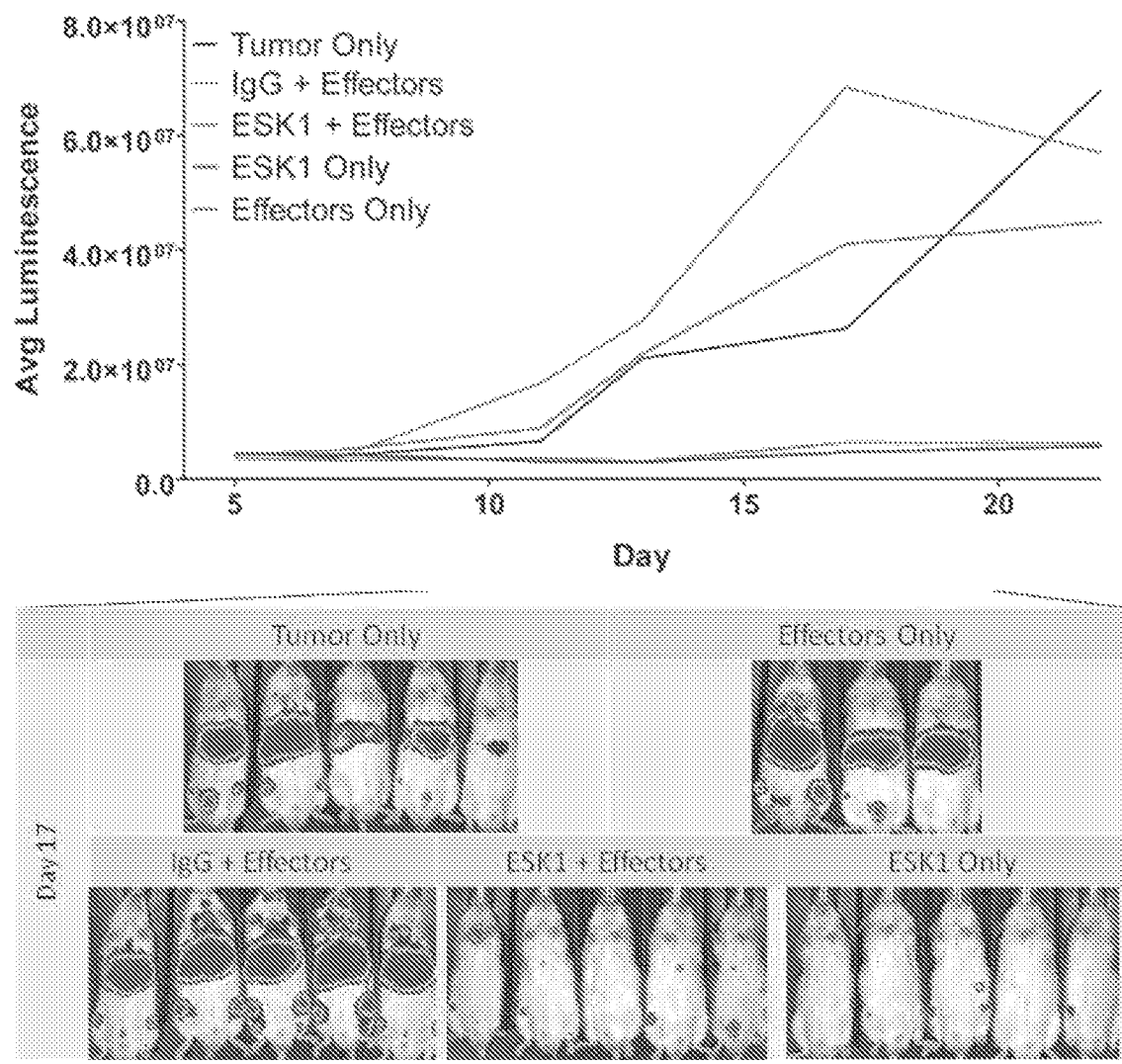
FIG. 31 shows the results of treatment of human BV173 in NSG mice using antibodies of the invention.
Figure 32:
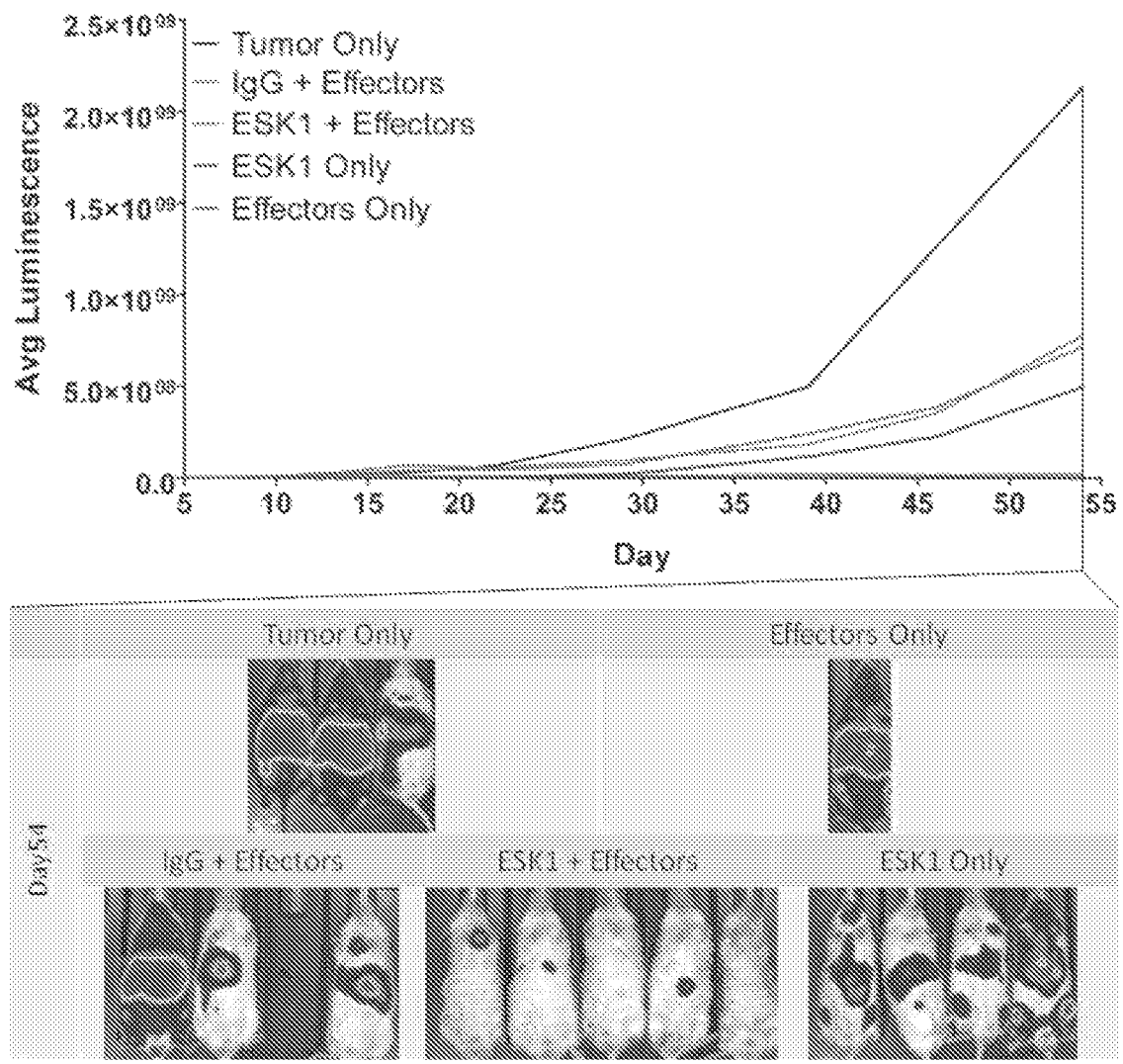
FIG. 32 shows that at later time points, mice treated with WT1 antibody only began to relapse, while antibody with effectors cured 2 of 5 mice.

The efficacy of WT1 ab1 in vivo was tested in NOD SCID gamma (NSG) mice xenografted intravenously 6 days previously with BV173 bcr/abl positive acute lymphoblastic leukemia. At the time of treatment, mice had leukemia in their liver, spleen, and BM visible by luciferase imaging. NSG mice lack mature B-, T- and NK-cells, and we hypothesized that introducing human effector cells (CD3$^-$, CD34$^-$, PBMCs) along with WT1 ab1 treatment would recapitulate in vivo the ADCC-mediated anti-tumor effects observed in vitro. Injection of effectors along with two 100 μg doses of WT1 ab1 nearly ablated tumor growth compared to controls (FIG. 31). This effect was durable over the course of the experiment (FIG. 32). Interestingly, early on in the trials, effector cells alone or combined with control IgG appeared to promote more rapid growth of leukemia relative to mice injected with leukemia alone, demonstrating that the anti-tumor effect was unrelated to the effectors by themselves. Several of the mice given effectors (with or without control mAb) died early in the experiment with massive infiltration of the BV173.

Figure 33:
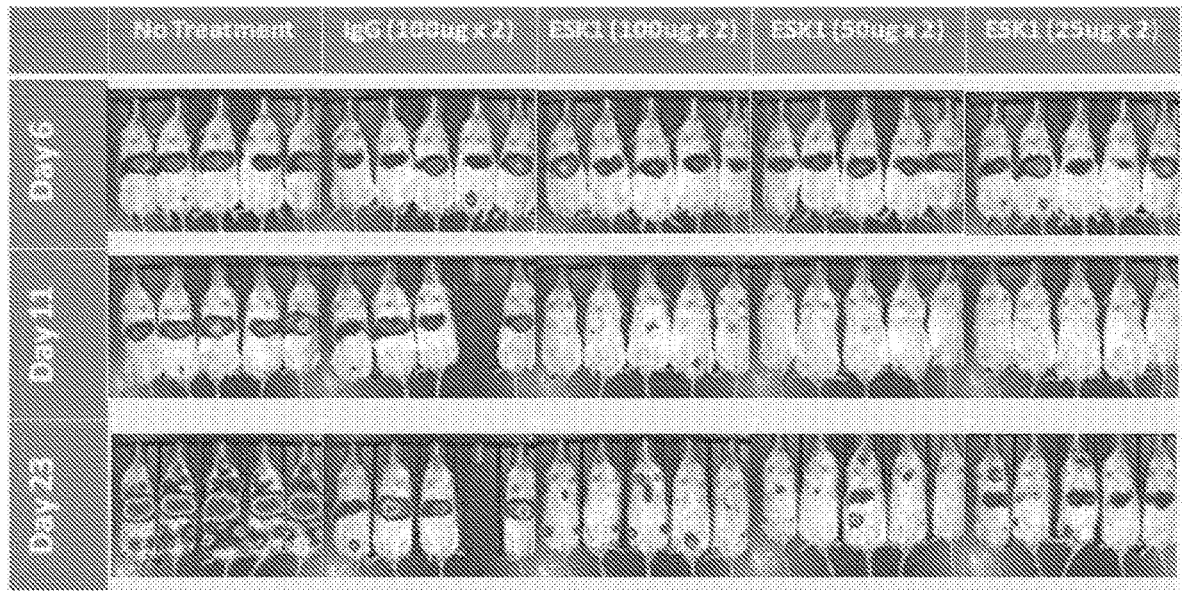
FIG. 33 shows that WT1 antibody significantly reduces tumor burden in a dose-dependent manner.

Surprisingly, WT1 ab1 treatment without human effectors also dramatically reduced tumor burden as well as the WT1 ab1 combined with effectors for approximately 30 days (FIG. 32), though tumors eventually relapsed far more quickly in the WT1 ab1 alone group, when compared to WT1 ab1 combined with effectors group (FIG. 32). We confirmed the effect of WT1 ab1 alone and titrated the dosage to evaluate potency. WT1 ab1 alone produced a marked reduction in tumor burden at early time points at all doses tested (25-100 μg times 2 doses). Tumors in all treatment groups relapsed slowly after antibody therapy was stopped; and by day 23 (13 days after the last antibody injection), significantly more tumor relapse could be observed in the 25 μg group compared to the 100 μg dose group, indicating a dose-response to WT1 ab1 therapy (FIG. 33). Before treatment, mice displayed the largest tumor burden in the liver, which was quickly cleared by WT1 ab1. Upon relapse, tumor in the highest dose group appeared to develop mainly in bone marrow, while tumor returned more quickly to the liver in mice treated with the lowest dose.

Example 9

Engineering Antibodies to Enhance their Cytotoxic Abilities.

Bispecific antibodies are constructed that recognize both WT1/A2 complex and CD3 on immune T cells as described (43,44) with a human IgG1 Fc. Bispecific antibodies are expected to recruit and target cytotoxic T cells to WT1/A2 positive cancer cells, while maintaining Fc effector functions and long half life in vivo. Three mechanisms are involved in the specific killing of cancer cells mediated by bispecific antibodies: i) killing by activated T cells; ii) ADCC activity; iii) CDC activity. Other formats of bispecific antibodies can be constructed, such tandem scFv molecules (taFv), diabodies (Db), or single chain diabodies (scDb), and fusion protein with human serum albumin (45, 46, 47, 48), but are devoid of Fc effector functions with distinct pharmacokinetic profiles.

WT1/A2 target specific-ADCC activity is enhanced by expressing antibodies recombinantly in glycol-engineered CHO cells as described in U.S. Pat. Nos. 8,025,879; 8,080, 415; and 8,084,022. The modified oligosaccharide N-glycan on Asn297 alters effector functions as follows: 1) higher affinity binding to CD16/FcRIIIa for improved ADCC activity mediated by human Natural Killer cells; 2) reduced binding affinity to CD32b/FcRIIb, an inhibitory receptor expressed in multiple types of immune cells (except NK cells), for improved ADCC activity mediated by effector cells such as neutrophils and antigen presentation by macrophage and DC cells (50, 51, 52). Enhanced antibodies are expected to achieve better efficacy for cancer treatment in vivo.

Glycosylation (specifically fucosylation) variants of IgG Fc can be produced using host expression cells and methods described in U.S. Pat. Nos. 8,025,879; 8,080,415; and 8,084, 022, the contents of which are incorporated by reference. Briefly, messenger RNA (mRNA) coding for heavy or light chain of the antibodies disclosed herein, is obtained by employing standard techniques of RNA isolation purification and optionally size based isolation. cDNAs corresponding to mRNAs coding for heavy or light chain are then produced and isolated using techniques known in the art, such as cDNA library construction, phage library construction and screening or RT-PCR using specific relevant primers. In some embodiments, the cDNA sequence may be one that is wholly or partially manufactured using known in vitro DNA manipulation techniques to produce a specific desired cDNA. The cDNA sequence can then be positioned in a vector which contains a promoter in reading frame with the gene and compatible with the low fucose-modified host cell.

Figure 34:
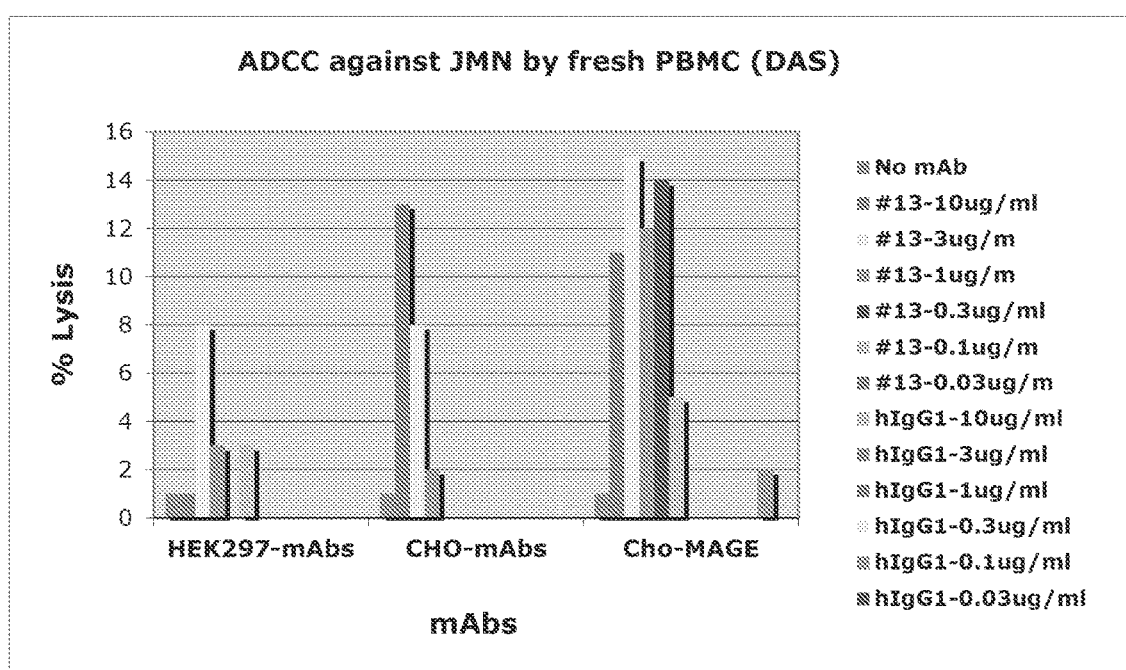
FIG. 34 shows that antibody with altered carbohydrate in Fc (MAGE) is more active in ADCC than original antibody.

Numerous plasmids that contain appropriate promoters, control sequences, ribosome binding sites, and transcription termination sites, and optionally convenient markers are known in the art, these include but are not limited to, vectors described in U.S. Pat. Nos. 4,663,283 and 4,456,748. In one embodiment, the cDNA coding for the light chain and that coding for the heavy chain may be inserted into separate expression plasmids. In an alternative embodiment, the cDNA coding for the light chain and that coding for the heavy chain may be inserted together in the same plasmid, so long as each is under suitable promoter and translation control. Results are shown in FIG. 34.

REFERENCES

1. Mundlos S, et al. Nuclear localization of the protein encoded by the Wilms' tumor gene WT1 in embryonic and adult tissues. *Development* 1993; 119: 1329-41.
2. Keilholz U, et al. Wilms' tumor gene 1 (WT1) in human neoplasia. *Leukemia* 2005; 19: 1318-1323.
3. Inoue K, et al. WT1 as a new prognostic factor and a new marker for the detection of minimal residual disease in acute leukemia. Blood 1994; 84 (9): 3071-3079.
4. Ogawa H, et al. The usefulness of monitoring WT1 gene transcripts for the prediction and management of relapse following allogeneic stem cell transplantation in acute type leukemia. Blood 2003; 101 (5): 1698-1704.
5. Yarnagarni T, et al. Growth Inhibition of Human Leukemic Cells by WTI (Wilms Tumor Gene) Antisense Oligodeoxynucleotides: Implications for the Involvement of WT1 in Leukemogenesis. *Blood* 1996; 87: 2878-2884.
6. Bellantuono I, et al. Two distinct HLA-A0201-presented epitopes of th Wilms tumor antigen 1 can function as targets for leukemia-reactive CTL. *Blood* 2002; 100 (10): 3835-3837.
7. Gaiger A, et al. WT1-specific serum antibodies in patients with leukemia. *Clin. Cancer Res.* 2001; 7 (suppl 3): 761-765.
8. Oka Y, et al. WT1 peptide cancer vaccine for patients with hematopoietic malignancies and solid cancers. *The Scientific World Journal* 2007; 7: 649-665.
9. Kobayashi H, et al. Defining MHC class II T helper epitopes from WT1 antigen. *Cancer Immunol. Immunother.* 2006; 55 (7): 850-860.
10. Pinilla-Ibarz J, et al. Improved human T-cell responses against synthetic HLA-A0201 analog peptides derived from the WT1 oncoprotein. *Leukemia* 2006; 20 (11): 2025-2033.
11. May R J, et al. Peptide epitopes from the Wilms tumor 1 oncoprotein stimulate CD4+ and CD8+ T cells that recognize and kill human malignant mesothelioma tumor cells. *Clin Cancer Res.* 2007; 13:4547-4555.
12. Keiholz U, et al. A clinical and immunologic phase 2 trial of Wils tumor gene product (WT1) peptide vaccination in patients with AML and MDS. Blood 2009; 113: 6541-6548.
13. Rezwani K, et al. Leukemia-associated antigen-specific T-cell responses following combined PR1 and WT1 peptide vaccination in patients with myeloid malignancies. Blood 2008; 111 (1): 236-242.
14. Maslak P, et al. Vaccination with synthetic analog peptides derived from WT1 oncoprotein induces T cell responses in patients with complete remission from acute myeloid leukemia. Blood 2010; Accpt Minor rev.
15. Krug L M, et al. WT1 peptide vaccinations induce CD4 and CD8 T cell immune responses in patients with mesothelioma and non-small cell lung cancer. *Cancer Immunol Immunother* 2010; in revision.
16. Morris E, et al. Generation of tumor-specific T-cell therapies. *Blood Reviews* 2006; 20: 61-69.
17. Houghton A N et al. Monoclonal antibody therapies—a "constant" threat to cancer. *Nat Med* 2000; 6:373-374.
18. Miederer M, et al. Realizing the potential of the Actinium-225 radionuclide generator in targeted alpha particle therapy applications. *Adv Drug Deliv Rev* 2008; 60 (12): 1371-1382.
19. Noy R, T-cell-receptor-like antibodies: novel reagents for clinical cancer immunology and immunotherapy. *Expert Rev Anticancer Ther* 2005: 5 (3): 523-536.
20. Chames P, et al. Direct selection of a human antibody fragment directed against the tumor T-cell epitope HLA-A1-MAGE-A1 from a nonimmunized phage-Fab library. Proc Natl Acad Sci USA 2000; 97: 7969-7974.
21. Held G, et al. Dissecting cytotoxic T cell responses towards the NY-ESO-1 protein by peptide/MHC-specific antibody fragments. *Eur J Immunol.* 2004: 34:2919-2929.
22. Lev A, et al. Isolation and characterization of human recombinant antibodies endowed with the antigen-specific, major histocompatibility complex-restricted specificity of T cells directed toward the widely expressed tumor T cell-epitopes of the telomerase catalytic subunit. *Cancer Res* 2002; 62: 3184-3194.
23. Klechevsky E, et al. Antitumor activity of immunotoxins with T-cell receptor-like specificity against human melanoma xenografts. *Cancer Res* 2008; 68 (15): 6360-6367.
24. Azinovic I, et al. Survival benefit associated with human anti-mouse antibody (HAMA) in patients with B-cell malignancies. *Cancer Immunol Immunother* 2006; 55(12):1451-8.
25. Tjandra J J, et al. Development of human anti-murine antibody (HAMA) response in patients. *Immunol Cell Biol* 1990; 68(6):367-76.
26. Riechmann L, et al. Reshaping human antibodies for therapy. *Nature* 1988; 332 (6162): 332:323.
27. Queen C, et al. A humanized antibody that binds to the interleukin 2 receptor. *Proc Natl Acad Sci USA* 1989; 86 (24): 10029-33.
28. Gerd R, et al. Serological Analysis of Human Anti-Human Antibody Responses in Colon Cancer Patients Treated with Repeated Doses of Humanized Monoclonal Antibody A33. *Cancer Res* 2001; 61, 6851-6859.
29. Cheever M A, et al. The prioritization of cancer antigens: A national Cancer Institute pilot project for the acceleration of translational research. *Clin Cancer Res* 2009; 15 (17): 5323-5337.
30. Drakos E, et al. Differential expression of WT1 gene product in non-Hodgkin lymphomas. *Appl Immunohistochem Mol Morphol* 2005; 13 (2): 132-137.
31. Asemissen A M, et al. Identification of a highly immunogenic HLA-A*01-binding T cell epitope of WT1. *Clin Cancer Res* 2006; 12 (24):7476-7482.
32. Tomimatsu K, et al. Production of human monoclonal antibodies against FceRIa by a method combining in vitro immunization with phage display. *Biosci Biotechnol Biochem* 2009; 73 (7): 1465-1469.
33. Lidija P, et al. An integrated vector system for the eukaryotic expression of antibodies or their fragments after selection from phage display libraries. *Gene* 1997; 187(1): 9-18.
34. Lisa J H, et al. Crystallographic structure of an intact IgG1 monoclonal antibody. *Journal of Molecular Biology* 1998; 275 (5): 861-872.
35. Yasmina N A, et al. Probing the binding mechanism and affinity of tanezumab, a recombinant humanized anti-NGF monoclonal antibody, using a repertoire of biosensors. *Protein Science* 2008; 17(8): 1326-1335.
36. Roberts W K, et al. Vaccination with CD20 peptides induces a biologically active, specific immune response in mice. *Blood* 2002: 99 (10): 3748-3755.
37. Caron P C, Class K, Laird W, Co M S, Queen C, Scheinberg D A. Engineered humanized dimeric forms of IgG are more effective antibodies. *J Exp Med* 176:1191-1195. 1992.
38. McDevitt M, et al. Tumor targeting with antibody-functionalized, radiolabeled carbon nanotubes. *J. Nuclear Med* 2207; 48 (7))1180-1189.

39. Xue S A, et al. Development of a Wilms' tumor-specific T-cell receptor for clinical trials: engineered patient's T cells can eliminate autologous leukemia blasts in NOD/SCID mice. *Haematologica* 2010; 95 (1): 126-134.
40. McDevitt M R, et al. Tumor therapy with targeted atomic nanogenerators. *Science* 2001; 294 (5546): 1537-1540.
41. Borchardt P E, et al. Targeted Actinium-225 in vivo generators for therapy of ovarian cancer. *Cancer Res* 2003; 63: 5084-5090.
42. Singh Jaggi J, et al. Selective alpha-particle mediated depletion of tumor vasculature with vascular normalization. *Plos One* 2007; 2 (3): e267.
43. Yan W, et al. Enhancing antibody Fc heterodimer formation through electrostatic steering effects. *J. Biol. Chem.* 2010; 285: 19637-19646.
44. Rossi E, et al. Stably tethered multi-functional structures of defined composition made by the dock and lock method for use in cancer targeting. *Proc Natl Aca Sci USA* 2006; 103:6841-6.
45. Ryutaro A, et al. Cytotoxic enhancement of a bispecific diabody by format conversion to tandem single-chain variable fragment (taFv). *J Biol Chem* 2011; 286: 1812-1818.
46. Anja L, et al. A recombinant bispecific single-chain antibody, CD19×CD3, induces rapid and high lymphoma-directed cytotoxicity by unstimulated T lymphocytes. *Blood* 2000; 95(6): 2098-2103.
47. Weiner G J, et al. The role of T cell activation in anti-CD3× antitumor bispecific antibody therapy. *J. Immunology* 1994; 152(5): 2385-2392.
48. Dafne M, et al. Improved pharmacokinetics of recombinant bispecific antibody molecules by fusion to human serum albumin. *J Biol Chem* 2007; 282: 12650-12660.
49. Liu C, et al. Modified host cells and uses thereof, PCT/US2010/0081195.
50. Francisco J, et al. Neutrophils Contribute to the Biological Antitumor Activity of Rituximab in a Non-Hodgkin's Lymphoma Severe Combined Immunodeficiency Mouse Model. *Clin Cancer Res* 2003; 9: 5866.
51. Kavita M, et al. Selective blockade of inhibitory Fc receptor enables human dendritic cell maturation with IL-12p70 production and immunity to antibody-coated tumor cells. *Proc Natl Aca Sci USA* 2005; 102(8): 2910-2915.
52. Raphael A, et al. Inhibitory Fc receptors modulate in vivo cytotoxicity against tumor targets. *Nature Medicine* 2000; 6:443-446.
53. Milenic E D. Monoclonal antibody-based therapy strategies: providing options for the cancer patient. *Curr Pharm Des.* 2002; 8: 1794-1764.
54. Grillo-Lopez A J. Anti-CD20 mAbs: modifying therapeutic strategies and outcomes in the treatment of lymphoma patients. *Expert Rev Anticancer Ther.* 2002: 2 (3): 323-329.
55. Jones K L & Buzdar A U. Evolving novel anti-Her2 strategies. *Lancet Oncol.* 2009: 10 (12): 1179-1187.
56. Reddy M M, Deshpande A & Sattler M. targeting JAK2 in the therapy of myeloproliferative neoplasms. Exper Opin Ther targets 2012: 3: 313-324.
57. Takeuchi K & Ito F. Receptor tyrosine kinases and targeted cancer therapeutics. Biol Pharm Bull. 2011; 34 (12) 1774-1780.
58. Roychowdhury S & Talpaz M. Managing resistance in chronic myeloid leukemia. Blood Rev. 2011; (6): 279-290.
59. Konnig R. Interactions between MHC molecules and co-receptors of the TCR. *Curr Opin Immunol* 2002: 14 (1) 75-83.
60. Sergeeva A, Alatrash G, He H, Ruisaard K, Lu S, Wygant J, McIntyre B W, Ma Q, Li D, St John L, Clise-Dwyer K & Molldrem J J. An anti-PR1/HLA-A2 T-cell receptor-like antibody mediated complement-dependent cytotoxicity against acute myeloid leukemia progenitor cells. *Blood* 2011; 117 (16): 4262-4272).
61. Takigawa N, Kiura K & Kishimoto T. Medical Treatment of Mesothelioma: Anything New? *Curr Oncol Rep* 2011; DOI 10.1007/s11912-011-0172-1.
62. Raja S, Murthy S C & Mason D P. Malignant Pleural Mesothelioma. *Curr Oncol Rep* 2011; DOI 10. 1007/s11912-0177-9.
63. Gerber J M, Qin L, Kowalski J, Smith D, Griffin C A, Vala M S, Collector M I, Perkins B, Zahurak M, Matsui W, Gocke C D, Sharkis S, Levitsky H & Jones R J. Characterization of chronic myeloid leukemia stem cells. 2011; *Am J Hematol.* 86: 31-37.
64. Rezwani K, Yong A S, Savani B N, Mielke S, Keyvanfar K, Gostick E, Price D A, Douek D C & Barrett A J. Graft-versus-leukemia effects associated with detectable Wilms tumor-1 specific T lymphocytes after allogeneic stem-cell transplantation for acute lymphoblastic leukemia. *Blood* 2007: 110 (6): 1924-1932.
65. Persic L, Roberts A, Wilton J et al. An integrated vector system for the eukaryotic expression of antibodies or their fragments after selection from phage display libraries. *Gene* 1997; 187(1): 9-18.
66. Cheng L, Xiang J Y, Yan S et al. Modified host cells and uses thereof. PCT/US2010/0081195.
67. Lindmo T, Boven E, Cuttitta F, Fedorko J & Bunn P A Jr. Determination of the immunoreactive fraction of radiolabeled monoclonal antibodies by linear extrapolation to binding at infinite antigen excess. *J Immunol Methods.* 1984; 72 (1): 77-89.
68. Feng M, Zhang J L, Anver M, Hassan R & Ho M. In vivo imaging of human malignant mesothelioma growth orthotopically in the peritoneal cavity of nude mice. *J Cancer* 2011; 2: 123-131.

What is claimed is:

1. A bispecific antibody comprising:
a first antigen binding fragment, comprising one of:
(a) a heavy chain (HC) variable region comprising HC-CDR1, HC-CDR2 and HC-CDR3 respectively, comprising amino acid sequences SEQ ID NOS: 2, 3, and 4; and a light chain (LC) variable region comprising LC-CDR1, LC-CDR2 and LC-CDR3 respectively, comprising amino acid sequences SEQ ID NOS: 8, 9 and 10;
(b) a heavy chain (HC) variable region comprising HC-CDR1, HC-CDR2 and HC-CDR3 respectively, comprising amino acid sequences SEQ ID NOS: 20, 21 and 22; and a light chain (LC) variable region comprising LC-CDR1, LC-CDR2 and LC-CDR3 respectively, comprising amino acid sequences SEQ ID NOS: 26, 27 and 28;
(c) a heavy chain (HC) variable region comprising HC-CDR1, HC-CDR2 and HC-CDR3 respectively, comprising amino acid sequences SEQ ID NOS: 38, 39 and 40; and a light chain (LC) variable region comprising LC-CDR1, LC-CDR2 and LC-CDR3 respectively, comprising amino acid sequences selected from SEQ ID NOS: 44, 45 and 46;
(d) a heavy chain (HC) variable region comprising HC-CDR1, HC-CDR2 and HC-CDR3 respectively, comprising amino acid sequences SEQ ID NOS: 56, 57 and 58; and a light chain (LC) variable region comprising LC-CDR1, LC-CDR2 and LC-CDR3 respectively, comprising amino acid sequences SEQ ID NOS: 62, 63 and 64;
(e) a heavy chain (HC) variable region comprising HC-CDR1, HC-CDR2 and HC-CDR3 respectively, comprising amino acid sequences SEQ ID NOS: 74, 75 and 76; and a light chain (LC) variable region comprising LC-CDR1, LC-CDR2 and LC-CDR3 respectively, comprising amino acid sequences SEQ ID NOS: 80, 81 and 82; or
(f) a heavy chain (HC) variable region comprising HC-CDR1, HC-CDR2 and HC-CDR3 respectively, comprising amino acid sequences SEQ ID NOS: 92, 93 and 94; and a light chain (LC) variable region comprising LC-CDR1, LC-CDR2 and LC-CDR3 respectively, comprising amino acid sequences SEQ ID NOS: 98, 99 and 100; and a second antigen binding fragment that binds to CD3.

2. The bispecific antibody of claim 1, wherein the first antigen binding fragment, comprises a $V_H$ and $V_L$ comprising first and second amino acid sequences, respectively, selected from SEQ ID NOS: 14 and 16; 32 and 34; 50 and 52; 68 and 70; 86 and 88; and 104 and 106.

3. The bispecific antibody of claim 1, wherein the first antigen binding fragment, comprises an amino acid sequence selected from SEQ ID NOS: 18, 36, 54, 72, 90, and 108.

4. The bispecific antibody of claim 1, wherein first antigen binding fragment specifically binds to an WT1 peptide bound to HLA-A2.

5. The bispecific antibody of claim 4, wherein said WT1 peptide has the amino acid sequence RMFPNAPYL (SEQ ID NO: 1).

6. The bispecific antibody of claim 4, wherein said HLA-A2 is HLA-A0201.

7. A method for treatment of a subject having a WT1-positive disease, comprising administering to the subject a therapeutically effective amount of the bispecific antibody of claim 1.

8. The method of claim 7, wherein the WT1-positive disease is a chronic leukemia or acute leukemia or WT1$^+$ cancer.

9. The method of claim 8, wherein the WT1-positive disease is selected from the group consisting of chronic myelocytic leukemia, multiple myeloma (MM), acute lymphoblastic leukemia (ALL), acute myeloid/myelogenous leukemia (AML), myelodysplastic syndrome (MDS), mesothelioma, ovarian cancer, gastrointestinal cancers, breast cancer, prostate cancer and glioblastoma.

10. A pharmaceutical composition comprising the bispecific antibody of claim 1.

* * * * *

SEQUENCE LISTING

```
<160> NUMBER OF SEQ ID NOS: 238

<210> SEQ ID NO 1
<211> LENGTH: 9
<212> TYPE: PRT
<213> ORGANISM: Homo sapiens

<400> SEQUENCE: 1

Arg Met Phe Pro Asn Ala Pro Tyr Leu
1               5
```

<210> SEQ ID NO 2
<211> LENGTH: 10
<212> TYPE: PRT
<213> ORGANISM: Homo sapiens

<400> SEQUENCE: 2

Gly Gly Thr Phe Ser Ser Tyr Ala Ile Ser
1               5                   10

<210> SEQ ID NO 3
<211> LENGTH: 17
<212> TYPE: PRT
<213> ORGANISM: Homo sapiens

<400> SEQUENCE: 3

Gly Ile Ile Pro Ile Phe Gly Thr Ala Asn Tyr Ala Gln Lys Phe Gln
1               5                   10                  15

Gly

<210> SEQ ID NO 4
<211> LENGTH: 10
<212> TYPE: PRT
<213> ORGANISM: Homo sapiens

<400> SEQUENCE: 4

Arg Ile Pro Pro Tyr Tyr Gly Met Asp Val
1               5                   10

<210> SEQ ID NO 5
<211> LENGTH: 30
<212> TYPE: DNA
<213> ORGANISM: Homo sapiens

<400> SEQUENCE: 5
ggaggcacct tcagcagcta tgctatcagc                              30

<210> SEQ ID NO 6
<211> LENGTH: 51
<212> TYPE: DNA
<213> ORGANISM: Homo sapiens

<400> SEQUENCE: 6
gggatcatcc ctatctttgg tacagcaaac tacgcacaga gttccagggc         51

<210> SEQ ID NO 7
<211> LENGTH: 30
<212> TYPE: DNA
<213> ORGANISM: Homo sapiens

<400> SEQUENCE: 7
cggattcccc cgtactacgg tatggacgtc                              30

<210> SEQ ID NO 8
<211> LENGTH: 13
<212> TYPE: PRT
<213> ORGANISM: Homo sapiens

<400> SEQUENCE: 8

Ser Gly Ser Ser Ser Asn Ile Gly Ser Asn Tyr Val Tyr
1               5                   10

<210> SEQ ID NO 9

<211> LENGTH: 7
<212> TYPE: PRT
<213> ORGANISM: Homo sapiens

<400> SEQUENCE: 9

Arg Ser Asn Gln Arg Pro Ser
1               5

<210> SEQ ID NO 10
<211> LENGTH: 11
<212> TYPE: PRT
<213> ORGANISM: Homo sapiens

<400> SEQUENCE: 10

Ala Ala Trp Asp Asp Ser Leu Asn Gly Val Val
1               5                   10

<210> SEQ ID NO 11
<211> LENGTH: 39
<212> TYPE: DNA
<213> ORGANISM: Homo sapiens

<400> SEQUENCE: 11
tctggaagca gctccaacat cggaagtaat tatgtatac                   39

<210> SEQ ID NO 12
<211> LENGTH: 21
<212> TYPE: DNA
<213> ORGANISM: Homo sapiens

<400> SEQUENCE: 12
aggagtaatc agcggccctc a                                      21

<210> SEQ ID NO 13
<211> LENGTH: 33
<212> TYPE: DNA
<213> ORGANISM: Homo sapiens

<400> SEQUENCE: 13
gcagcatggg atgacagcct gaatggtgtg gta                         33

<210> SEQ ID NO 14
<211> LENGTH: 119
<212> TYPE: PRT
<213> ORGANISM: Homo sapiens

<400> SEQUENCE: 14

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Ile Pro Pro Tyr Tyr Gly Met Asp Val Trp Gly Gln Gly
            100                 105                 110

Thr Thr Val Thr Val Ser Ser
        115

<210> SEQ ID NO 15
<211> LENGTH: 357
<212> TYPE: DNA
<213> ORGANISM: Homo sapiens

<400> SEQUENCE: 15
caggtgcagc tggtgcagtc tggggctgag gtgaagaagc ctgggtcctc ggtgaaggtc     60
tcctgcaagg cttctggagg caccttcagc agctatgcta tcagctgggt gcgacaggcc    120
cctggacaag gcttgagtg gatgggaggg atcatcccta tctttggtac agcaaactac    180
gcacagaagt tccagggcag agtcacgatt accgcggacg aatccacgag cacagcctac    240
atggagctga gcagcctgag atctgaggac acggccgtgt attactgtgc gagacggatt    300
cccccgtact acggtatgga cgtctggggc caagggacca cggtcaccgt ctcctca      357

<210> SEQ ID NO 16
<211> LENGTH: 111
<212> TYPE: PRT
<213> ORGANISM: Homo sapiens

<400> SEQUENCE: 16

Gln Thr Val Val Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Arg Ser Asn Gln Arg Pro Ser Gly Val Pro Asp Arg Phe Ser
    50                  55                  60

Gly Ser Lys Ser Gly Thr Ser Ala Ser Leu Ala Ile Ser Gly Pro Arg
65                  70                  75                  80

Ser Val Asp Glu Ala Asp Tyr Tyr Cys Ala Ala Trp Asp Asp Ser Leu
                85                  90                  95

Asn Gly Val Val Phe Gly Gly Gly Thr Lys Leu Thr Val Leu Gly
            100                 105                 110

<210> SEQ ID NO 17
<211> LENGTH: 333
<212> TYPE: DNA
<213> ORGANISM: Homo sapiens

<400> SEQUENCE: 17
cagactgtgg tgactcagcc accctcagcg tctgggaccc ccgggcagag ggtcaccatc     60
tcttgttctg gaagcagctc caacatcgga agtaattatg tatactggta ccaacagctc    120
ccaggaacgg cccccaaact cctcatctat aggagtaatc agcggccctc agggtccct    180 gaccgattct ctggctccaa gtctggcacc tcagcctccc tggccatcag tgggccccgg    240
tccgtggatg aggctgatta ttactgtgca gcatgggatg acagcctgaa tggtgtggta    300
ttcggcggag ggaccaagct gaccgtccta ggt                                333

<210> SEQ ID NO 18
<211> LENGTH: 250
<212> TYPE: PRT
<213> ORGANISM: Homo sapiens

<400> SEQUENCE: 18

```
Gln Thr Val Val Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Arg Ser Asn Gln Arg Pro Ser Gly Val Pro Asp Arg Phe Ser
    50                  55                  60

Gly Ser Lys Ser Gly Thr Ser Ala Ser Leu Ala Ile Ser Gly Pro Arg
65                  70                  75                  80

Ser Val Asp Glu Ala Asp Tyr Tyr Cys Ala Ala Trp Asp Asp Ser Leu
                85                  90                  95

Asn Gly Val Val Phe Gly Gly Gly Thr Lys Leu Thr Val Leu Gly Ser
            100                 105                 110

Arg Gly Gly Gly Gly Ser Gly Gly Gly Gly Ser Gly Gly Gly Ser Leu
        115                 120                 125

Glu Met Ala Gln Val Gln Leu Val Gln Ser Gly Ala Glu Val Lys Lys
    130                 135                 140

Pro Gly Ser Ser Val Lys Val Ser Cys Lys Ala Ser Gly Gly Thr Phe
145                 150                 155                 160

Ser Ser Tyr Ala Ile Ser Trp Val Arg Gln Ala Pro Gly Gln Gly Leu
                165                 170                 175

Glu Trp Met Gly Gly Ile Ile Pro Ile Phe Gly Thr Ala Asn Tyr Ala
            180                 185                 190

Gln Lys Phe Gln Gly Arg Val Thr Ile Thr Ala Asp Glu Ser Thr Ser
        195                 200                 205

Thr Ala Tyr Met Glu Leu Ser Ser Leu Arg Ser Glu Asp Thr Ala Val
    210                 215                 220

Tyr Tyr Cys Ala Arg Arg Ile Pro Pro Tyr Tyr Gly Met Asp Val Trp
225                 230                 235                 240

Gly Gln Gly Thr Thr Val Thr Val Ser Ser
                245                 250

<210> SEQ ID NO 19
<211> LENGTH: 750
<212> TYPE: DNA
<213> ORGANISM: Homo sapiens

<400> SEQUENCE: 19
cagactgtgg tgactcagcc accctcagcg tctgggaccc ccgggcagag ggtcaccatc      60
tcttgttctg gaagcagctc caacatcgga agtaattatg tatactggta ccaacagctc     120
ccaggaacgg ccccccaaact cctcatctat aggagtaatc agcggccctc agggtccct     180 gaccgattct ctggctccaa gtctggcacc tcagcctccc tggccatcag tgggccccgg     240
tccgtggatg aggctgatta ttactgtgca gcatgggatg acagcctgaa tggtgtggta     300
ttcggcggag ggaccaagct gaccgtccta ggttctagag gtggtggtgg tagcggcggc     360
ggcggctctg gtggtggatc cctcgagatg gcccaggtgc agctggtgca gtctggggct     420
gaggtgaaga agcctgggtc ctcggtgaag gtctcctgca aggcttctgg aggcaccttc     480
agcagctatg ctatcagctg ggtgcgacag gcccctggac aagggcttga gtggatggga     540
gggatcatcc ctatctttgg tacagcaaac tacgcacaga agttccaggg cagagtcacg     600
attaccgcgg acgaatccac gagcacagcc tacatggagc tgagcagcct gagatctgag     660
```

```
gacacggccg tgtattactg tgcgagacgg attcccccgt actacggtat ggacgtctgg    720
ggccaaggga ccacggtcac cgtctcctca                                     750
```

<210> SEQ ID NO 20
<211> LENGTH: 12
<212> TYPE: PRT
<213> ORGANISM: Homo sapiens

<400> SEQUENCE: 20

```
Gly Asp Ser Val Ser Ser Asn Ser Ala Ala Trp Asn
1               5                   10
```

<210> SEQ ID NO 21
<211> LENGTH: 18
<212> TYPE: PRT
<213> ORGANISM: Homo sapiens

<400> SEQUENCE: 21

```
Arg Thr Tyr Tyr Gly Ser Lys Trp Tyr Asn Asp Tyr Ala Val Ser Val
1               5                   10                  15

Lys Ser
```

<210> SEQ ID NO 22
<211> LENGTH: 9
<212> TYPE: PRT
<213> ORGANISM: Homo sapiens

<400> SEQUENCE: 22

```
Gly Arg Leu Gly Asp Ala Phe Asp Ile
1               5
```

<210> SEQ ID NO 23
<211> LENGTH: 36
<212> TYPE: DNA
<213> ORGANISM: Homo sapiens

<400> SEQUENCE: 23

```
ggggacagtg tctctagcaa cagtgctgct tggaac                              36
```

<210> SEQ ID NO 24
<211> LENGTH: 54
<212> TYPE: DNA
<213> ORGANISM: Homo sapiens

<400> SEQUENCE: 24

```
aggacatact acgggtccaa gtggtataat gattatgcag tatctgtgaa aagt          54
```

<210> SEQ ID NO 25
<211> LENGTH: 27
<212> TYPE: DNA
<213> ORGANISM: Homo sapiens

<400> SEQUENCE: 25

```
ggtcgcttag gggatgcttt tgatatc                                        27
```

<210> SEQ ID NO 26
<211> LENGTH: 11
<212> TYPE: PRT
<213> ORGANISM: Homo sapiens

<400> SEQUENCE: 26

```
Arg Ala Ser Gln Ser Ile Ser Ser Tyr Leu Asn
1               5                   10
```

```
<210> SEQ ID NO 27
<211> LENGTH: 7
<212> TYPE: PRT
<213> ORGANISM: Homo sapiens

<400> SEQUENCE: 27

Ala Ala Ser Ser Leu Gln Ser
1               5

<210> SEQ ID NO 28
<211> LENGTH: 9
<212> TYPE: PRT
<213> ORGANISM: Homo sapiens

<400> SEQUENCE: 28

Gln Gln Ser Tyr Ser Thr Pro Leu Thr
1               5

<210> SEQ ID NO 29
<211> LENGTH: 33
<212> TYPE: DNA
<213> ORGANISM: Homo sapiens

<400> SEQUENCE: 29
cgggcaagtc agagcattag cagctattta aat                                 33

<210> SEQ ID NO 30
<211> LENGTH: 21
<212> TYPE: DNA
<213> ORGANISM: Homo sapiens

<400> SEQUENCE: 30
gctgcatcca gtttgcaaag t                                              21

<210> SEQ ID NO 31
<211> LENGTH: 27
<212> TYPE: DNA
<213> ORGANISM: Homo sapiens

<400> SEQUENCE: 31
caacagagtt acagtacccc tctcact                                        27

<210> SEQ ID NO 32
<211> LENGTH: 121
<212> TYPE: PRT
<213> ORGANISM: Homo sapiens

<400> SEQUENCE: 32

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Gly Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95
```

Tyr Tyr Cys Ala Arg Gly Arg Leu Gly Asp Ala Phe Asp Ile Trp Gly
            100                 105                 110

Gln Gly Thr Met Val Thr Val Ser Ser
        115                 120

<210> SEQ ID NO 33
<211> LENGTH: 363
<212> TYPE: DNA
<213> ORGANISM: Homo sapiens

<400> SEQUENCE: 33
caggtacagc tgcagcagtc aggtccagga ctggtgaagc cctcgcagac cctctcactc      60
acctgtgcca tctccgggga cagtgtctct agcaacagtg ctgcttggaa ctggatcagg     120
cagtccccat cgagaggcct tgagtggctg gaaggacat actacgggtc caagtggtat      180
aatgattatg cagtatctgt gaaaagtcga ataaccatca cccagacac atccaagaac      240 cagttctccc tgcagctgaa ctctgtgact cccgaggaca cggctgtgta ttactgtgca     300
agaggtcgct taggggatgc ttttgatatc tggggccaag gacaatggt caccgtctct      360 tca                                                                  363

<210> SEQ ID NO 34
<211> LENGTH: 108
<212> TYPE: PRT
<213> ORGANISM: Homo sapiens

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Asp Ile Lys Arg
            100                 105

<210> SEQ ID NO 35
<211> LENGTH: 324
<212> TYPE: DNA
<213> ORGANISM: Homo sapiens

<400> SEQUENCE: 35
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct     240
gaagattttg caacttacta ctgtcaacag agttacagta cccctctcac tttcggcgga     300
gggaccaaag tggatatcaa acgt                                           324

<210> SEQ ID NO 36

```
<211> LENGTH: 250
<212> TYPE: PRT
<213> ORGANISM: Homo sapiens

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Asp Ile Lys Arg Ser Arg Gly Gly
            100                 105                 110

Gly Gly Ser Gly Gly Gly Gly Ser Gly Gly Gly Ser Leu Glu Met
        115                 120                 125

Ala Gln Val Gln Leu Gln Gln Ser Gly Pro Gly Leu Val Lys Pro Ser
    130                 135                 140

Gln Thr Leu Ser Leu Thr Cys Ala Ile Ser Gly Asp Ser Val Ser Ser
145                 150                 155                 160

Asn Ser Ala Ala Trp Asn Trp Ile Arg Gln Ser Pro Ser Arg Gly Leu
                165                 170                 175

Glu Trp Leu Gly Arg Thr Tyr Tyr Gly Ser Lys Trp Tyr Asn Asp Tyr
            180                 185                 190

Ala Val Ser Val Lys Ser Arg Ile Thr Ile Asn Pro Asp Thr Ser Lys
        195                 200                 205

Asn Gln Phe Ser Leu Gln Leu Asn Ser Val Thr Pro Glu Asp Thr Ala
    210                 215                 220

Val Tyr Tyr Cys Ala Arg Gly Arg Leu Gly Asp Ala Phe Asp Ile Trp
225                 230                 235                 240

Gly Gln Gly Thr Met Val Thr Val Ser Ser
                245                 250

<210> SEQ ID NO 37
<211> LENGTH: 750
<212> TYPE: DNA
<213> ORGANISM: Homo sapiens

<400> SEQUENCE: 37
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatgct gcatccagtt tgcaaagtgg ggtcccatca     180
aggttcagtg gcagtggatc tgggacagat tcactctca ccatcagcag tctgcaacct     240
gaagattttg caacttacta ctgtcaacag agttacagta cccctctcac tttcggcgga     300
gggaccaaag tggatatcaa acgttctaga ggtggtggtg gtagcggcgg cggcggctct     360
ggtggtggtg gatccctcga gatggcccag gtacagctgc agcagtcagg tccaggactg     420
gtgaagccct cgcagaccct ctcactcacc tgtgccatct ccggggacag tgtctctagc     480
aacagtgctg cttggaactg gatcaggcag tccccatcga gaggccttga gtggctggga     540
```

-continued

```
aggacatact acgggtccaa gtggtataat gattatgcag tatctgtgaa aagtcgaata      600
accatcaacc cagacacatc caagaaccag ttctccctgc agctgaactc tgtgactccc      660
gaggacacgg ctgtgtatta ctgtgcaaga ggtcgcttag gggatgcttt tgatatctgg      720
ggccaaggga caatggtcac cgtctcttca                                       750
```

<210> SEQ ID NO 38
<211> LENGTH: 10
<212> TYPE: PRT
<213> ORGANISM: Homo sapiens

<400> SEQUENCE: 38

Gly Tyr Ser Phe Thr Asn Phe Trp Ile Ser
1               5                   10

<210> SEQ ID NO 39
<211> LENGTH: 17
<212> TYPE: PRT
<213> ORGANISM: Homo sapiens

<400> SEQUENCE: 39

Arg Val Asp Pro Gly Tyr Ser Tyr Ser Thr Tyr Ser Pro Ser Phe Gln
1               5                   10                  15

Gly

<210> SEQ ID NO 40
<211> LENGTH: 12
<212> TYPE: PRT
<213> ORGANISM: Homo sapiens

<400> SEQUENCE: 40

Val Gln Tyr Ser Gly Tyr Tyr Asp Trp Phe Asp Pro
1               5                   10

<210> SEQ ID NO 41
<211> LENGTH: 30
<212> TYPE: DNA
<213> ORGANISM: Homo sapiens

<400> SEQUENCE: 41

```
ggatacagct tcaccaactt ctggatcagc                                        30
```

<210> SEQ ID NO 42
<211> LENGTH: 51
<212> TYPE: DNA
<213> ORGANISM: Homo sapiens

<400> SEQUENCE: 42

```
agggttgatc ctggctactc ttatagcacc tacagcccgt ccttccaagg c                51
```

<210> SEQ ID NO 43
<211> LENGTH: 36
<212> TYPE: DNA
<213> ORGANISM: Homo sapiens

<400> SEQUENCE: 43

```
gtacaatata gtggctacta tgactggttc gacccc                                 36
```

<210> SEQ ID NO 44
<211> LENGTH: 13
<212> TYPE: PRT
<213> ORGANISM: Homo sapiens

<400> SEQUENCE: 44

Ser Gly Ser Ser Ser Asn Ile Gly Ser Asn Thr Val Asn
1               5                   10

<210> SEQ ID NO 45
<211> LENGTH: 7
<212> TYPE: PRT
<213> ORGANISM: Homo sapiens

<400> SEQUENCE: 45

Ser Asn Asn Gln Arg Pro Ser
1               5

<210> SEQ ID NO 46
<211> LENGTH: 11
<212> TYPE: PRT
<213> ORGANISM: Homo sapiens

<400> SEQUENCE: 46

Ala Ala Trp Asp Asp Ser Leu Asn Gly Trp Val
1               5                   10

<210> SEQ ID NO 47
<211> LENGTH: 39
<212> TYPE: DNA
<213> ORGANISM: Homo sapiens

<400> SEQUENCE: 47
tctggaagca gctccaacat cggaagtaat actgtaaac                          39

<210> SEQ ID NO 48
<211> LENGTH: 21
<212> TYPE: DNA
<213> ORGANISM: Homo sapiens

<400> SEQUENCE: 48
agtaataatc agcggccctc a                                             21

<210> SEQ ID NO 49
<211> LENGTH: 33
<212> TYPE: DNA
<213> ORGANISM: Homo sapiens

<400> SEQUENCE: 49
gcagcatggg atgacagcct gaatggttgg gtg                                33

<210> SEQ ID NO 50
<211> LENGTH: 121
<212> TYPE: PRT
<213> ORGANISM: Homo sapiens

<400> SEQUENCE: 50

Gln Met Gln Leu Val Gln Ser Gly Ala Glu Val Lys Glu Pro Gly Glu
1               5                   10                  15

Ser Leu Arg Ile Ser Cys Lys Gly Ser Gly Tyr Ser Phe Thr Asn Phe
                20                  25                  30

Trp Ile Ser Trp Val Arg Gln Met Pro Gly Lys Gly Leu Glu Trp Met
            35                  40                  45

Gly Arg Val Asp Pro Gly Tyr Ser Tyr Ser Tyr Ser Pro Ser Phe
        50                  55                  60

Gln Gly His Val Thr Ile Ser Ala Asp Lys Ser Thr Ser Thr Ala Tyr

Leu Gln Trp Asn Ser Leu Lys Ala Ser Asp Thr Ala Met Tyr Tyr Cys
                    85                  90                  95

Ala Arg Val Gln Tyr Ser Gly Tyr Tyr Asp Trp Phe Asp Pro Trp Gly
                100                 105                 110

Gln Gly Thr Leu Val Thr Val Ser Ser
            115                 120

<210> SEQ ID NO 51
<211> LENGTH: 363
<212> TYPE: DNA
<213> ORGANISM: Homo sapiens

<400> SEQUENCE: 51
cagatgcagc tggtgcagtc cggagcagag gtgaaagagc ccggggagtc tctgaggatc    60
tcctgtaagg gttctggata cagcttcacc aacttctgga tcagctgggt cgcgcagatg   120
cccgggaaag gcctggagtg gatggggagg gttgatcctg ctactctta  tagcacctac   180 agcccgtcct ccaaggcca  cgtcaccatc tcagctgaca agtctaccag cactgcctac   240
ctgcagtgga cagcctgaa  ggcctcggac accgccatgt attactgtgc gagagtacaa   300
tatagtggct actatgactg gttcgacccc tggggccagg gaaccctggt caccgtctcc   360
tca                                                                 363

<210> SEQ ID NO 52
<211> LENGTH: 111
<212> TYPE: PRT
<213> ORGANISM: Homo sapiens

<400> SEQUENCE: 52

Gln Ala Val Val Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
                20                  25                  30

Thr Val Asn Trp Tyr Gln Gln Val Pro Gly Thr Ala Pro Lys Leu Leu
                35                  40                  45

Ile Tyr Ser Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Trp Val Phe Gly Gly Gly Thr Lys Leu Thr Val Leu Gly
                100                 105                 110

<210> SEQ ID NO 53
<211> LENGTH: 333
<212> TYPE: DNA
<213> ORGANISM: Homo sapiens

<400> SEQUENCE: 53
caggctgtgg tgactcagcc accctcagcg tctgggaccc ccgggcagag ggtcaccatc    60
tcttgttctg gaagcagctc caacatcgga agtaatactg taaactggta ccagcaggtc   120
ccaggaacgg cccccaaact cctcatctat agtaataatc agcggccctc agggtccct   180 gaccgattct ctggctccaa gtctggcacc tcagcctccc tggccatcag tgggctccag   240
tctgaggatg aggctgatta ttactgtgca gcatgggatg acagcctgaa tggttgggtg   300
ttcggcggag ggaccaagct gaccgtccta ggt    333

<210> SEQ ID NO 54
<211> LENGTH: 253
<212> TYPE: PRT
<213> ORGANISM: Homo sapiens

<400> SEQUENCE: 54

Gln Ala Val Val Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Val Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Trp Val Phe Gly Gly Gly Thr Lys Leu Thr Val Leu Gly Ser
            100                 105                 110

Arg Gly Gly Gly Ser Gly Gly Gly Ser Gly Gly Gly Ser
        115                 120                 125

Leu Glu Met Ala Gln Met Gln Leu Val Gln Ser Gly Ala Glu Val Lys
    130                 135                 140

Glu Pro Gly Glu Ser Leu Arg Ile Ser Cys Lys Gly Ser Gly Tyr Ser
145                 150                 155                 160

Phe Thr Asn Phe Trp Ile Ser Trp Val Arg Gln Met Pro Gly Lys Gly
                165                 170                 175

Leu Glu Trp Met Gly Arg Val Asp Pro Gly Tyr Ser Tyr Ser Thr Tyr
            180                 185                 190

Ser Pro Ser Phe Gln Gly His Val Thr Ile Ser Ala Asp Lys Ser Thr
        195                 200                 205

Ser Thr Ala Tyr Leu Gln Trp Asn Ser Leu Lys Ala Ser Asp Thr Ala
    210                 215                 220

Met Tyr Tyr Cys Ala Arg Val Gln Tyr Ser Gly Tyr Tyr Asp Trp Phe
225                 230                 235                 240

Asp Pro Trp Gly Gln Gly Thr Leu Val Thr Val Ser Ser
                245                 250

<210> SEQ ID NO 55
<211> LENGTH: 759
<212> TYPE: DNA
<213> ORGANISM: Homo sapiens

<400> SEQUENCE: 55
caggctgtgg tgactcagcc accctcagcg tctgggaccc ccgggcagag ggtcaccatc    60
tcttgttctg gaagcagctc caacatcgga agtaatactg taaactggta ccagcaggtc    120
ccaggaacgg ccccccaaact cctcatctat agtaataatc agcggccctc agggtcccct    180
gaccgattct ctggctccaa gtctggcacc tcagcctccc tggccatcag tgggctccag    240
tctgaggatg aggctgatta ttactgtgca gcatgggatg acagcctgaa tggttgggtg    300
ttcggcggag ggaccaagct gaccgtccta ggttctagag gtggtggtgg tagcggcggc    360

```
ggcggctctg gtggtggtgg atccctcgag atggcccaga tgcagctggt gcagtccgga      420
gcagaggtga aagagcccgg ggagtctctg aggatctcct gtaagggttc tggatacagc      480
ttcaccaact tctggatcag ctgggtgcgc cagatgcccg ggaaaggcct ggagtggatg      540 gggaggggttg atcctggcta ctcttatagc acctacagcc cgtccttcca aggccacgtc      600
```
(ggagggttg atcctggcta ctcttatagc acctacagcc cgtccttcca aggccacgtc      600)
```
accatctcag ctgacaagtc taccagcact gcctacctgc agtggaacag cctgaaggcc      660
tcggacaccg ccatgtatta ctgtgcgaga gtacaatata gtggctacta tgactggttc      720 gaccccctggg gccagggaac cctggtcacc gtctcctca                            759
```
(gacccctggg gccagggaac cctggtcacc gtctcctca                            759)

<210> SEQ ID NO 56
<211> LENGTH: 10
<212> TYPE: PRT
<213> ORGANISM: Homo sapiens

<400> SEQUENCE: 56

Gly Tyr Asn Phe Ser Asn Lys Trp Ile Gly
1               5                   10

<210> SEQ ID NO 57
<211> LENGTH: 17
<212> TYPE: PRT
<213> ORGANISM: Homo sapiens

<400> SEQUENCE: 57

Ile Ile Tyr Pro Gly Tyr Ser Asp Ile Thr Tyr Ser Pro Ser Phe Gln
1               5                   10                  15

Gly

<210> SEQ ID NO 58
<211> LENGTH: 9
<212> TYPE: PRT
<213> ORGANISM: Homo sapiens

<400> SEQUENCE: 58

His Thr Ala Leu Ala Gly Phe Asp Tyr
1               5

<210> SEQ ID NO 59
<211> LENGTH: 30
<212> TYPE: DNA
<213> ORGANISM: Homo sapiens

<400> SEQUENCE: 59
ggctacaact ttagcaacaa gtggatcggc                                       30

<210> SEQ ID NO 60
<211> LENGTH: 51
<212> TYPE: DNA
<213> ORGANISM: Homo sapiens

<400> SEQUENCE: 60
atcatctatc ccggttactc ggacatcacc tacagcccgt ccttccaagg c               51

<210> SEQ ID NO 61
<211> LENGTH: 27
<212> TYPE: DNA
<213> ORGANISM: Homo sapiens

<400> SEQUENCE: 61
cacacagctt tggccggctt tgactac                                          27

```
<210> SEQ ID NO 62
<211> LENGTH: 11
<212> TYPE: PRT
<213> ORGANISM: Homo sapiens

<400> SEQUENCE: 62

Arg Ala Ser Gln Asn Ile Asn Lys Trp Leu Ala
1               5                   10

<210> SEQ ID NO 63
<211> LENGTH: 7
<212> TYPE: PRT
<213> ORGANISM: Homo sapiens

<400> SEQUENCE: 63

Lys Ala Ser Ser Leu Glu Ser
1               5

<210> SEQ ID NO 64
<211> LENGTH: 8
<212> TYPE: PRT
<213> ORGANISM: Homo sapiens

<400> SEQUENCE: 64

Gln Gln Tyr Asn Ser Tyr Ala Thr
1               5

<210> SEQ ID NO 65
<211> LENGTH: 33
<212> TYPE: DNA
<213> ORGANISM: Homo sapiens

<400> SEQUENCE: 65
cgggccagtc agaatatcaa taagtggctg gcc                                    33

<210> SEQ ID NO 66
<211> LENGTH: 21
<212> TYPE: DNA
<213> ORGANISM: Homo sapiens

<400> SEQUENCE: 66
aaggcgtcta gtttagaaag t                                                 21

<210> SEQ ID NO 67
<211> LENGTH: 24
<212> TYPE: DNA
<213> ORGANISM: Homo sapiens

<400> SEQUENCE: 67
caacaatata atagttatgc gacg                                              24

<210> SEQ ID NO 68
<211> LENGTH: 118
<212> TYPE: PRT
<213> ORGANISM: Homo sapiens

<400> SEQUENCE: 68

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Asn Phe Ser Asn Lys
            20                  25                  30

Trp Ile Gly Trp Val Arg Gln Leu Pro Gly Arg Gly Leu Glu Trp Ile
        35                  40                  45
```

Ala Ile Ile Tyr Pro Gly Tyr Ser Asp Ile Thr Tyr Ser Pro Ser Phe
    50                  55                  60

Gln Gly Arg Val Thr Ile Ser Ala Asp Thr Ser Ile Asn Thr Ala Tyr
65                  70                  75                  80

Leu His Trp His Ser Leu Lys Ala Ser Asp Thr Ala Met Tyr Tyr Cys
                85                  90                  95

Val Arg His Thr Ala Leu Ala Gly Phe Asp Tyr Trp Gly Leu Gly Thr
            100                 105                 110

Leu Val Thr Val Ser Ser
            115

<210> SEQ ID NO 69
<211> LENGTH: 354
<212> TYPE: DNA
<213> ORGANISM: Homo sapiens

<400> SEQUENCE: 69
caggtgcagc tggtgcagtc tggagcagag gtgaaaaagc ccggagagtc tctgaagatc      60
tcctgtaagg gttctggcta caactttagc aacaagtgga tcggctgggt gcgccaattg     120
cccgggagag gcctggagtg gatagcaatc atctatcccg gttactcgga catcacctac     180
agcccgtcct tccaaggccg cgtcaccatc tccgccgaca cgtccattaa caccgcctac     240
ctgcactggc acagcctgaa ggcctcggac accgccatgt attattgtgt gcgacacaca     300
gctttggccg gctttgacta ctggggcctg gcaccctgg tcaccgtctc ctca            354

<210> SEQ ID NO 70
<211> LENGTH: 107
<212> TYPE: PRT
<213> ORGANISM: Homo sapiens

<400> SEQUENCE: 70

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Asn Ile Asn Lys Trp
            20                  25                  30

Leu Ala Trp Tyr Gln Gln Arg Pro Gly Lys Ala Pro Gln Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Tyr Thr Leu Thr Ile Ser Ser Leu Gln Pro
65                  70                  75                  80

Asp Asp Phe Ala Thr Tyr Tyr Cys Gln Gln Tyr Asn Ser Tyr Ala Thr
                85                  90                  95

Phe Gly Gln Gly Thr Lys Val Glu Ile Lys Arg
            100                 105

<210> SEQ ID NO 71
<211> LENGTH: 321
<212> TYPE: DNA
<213> ORGANISM: Homo sapiens

<400> SEQUENCE: 71
gacatccaga tgacccagtc tccttccacc ctgtctgcat ctgtaggaga cagagtcaca     60
atcacttgcc gggccagtca gaatatcaat aagtggctgg cctggtatca gcagagacca    120
gggaaagccc ctcagctcct gatctataag gcgtctagtt tagaaagtgg ggtcccatct    180

```
aggttcagcg gcagtggatc tgggacagaa tacactctca ccatcagcag cctgcagcct      240
gatgattttg caacttatta ctgccaacaa tataatagtt atgcgacgtt cggccaaggg      300
accaaggtgg aaatcaaacg t                                                321
```

<210> SEQ ID NO 72
<211> LENGTH: 246
<212> TYPE: PRT
<213> ORGANISM: Homo sapiens

<400> SEQUENCE: 72

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Asn Ile Asn Lys Trp
            20                  25                  30

Leu Ala Trp Tyr Gln Gln Arg Pro Gly Lys Ala Pro Gln Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Tyr Thr Leu Thr Ile Ser Ser Leu Gln Pro
65                  70                  75                  80

Asp Asp Phe Ala Thr Tyr Tyr Cys Gln Gln Tyr Asn Ser Tyr Ala Thr
                85                  90                  95

Phe Gly Gln Gly Thr Lys Val Glu Ile Lys Arg Ser Arg Gly Gly Gly
            100                 105                 110

Gly Ser Gly Gly Gly Gly Ser Gly Gly Gly Gly Ser Leu Glu Met Ala
        115                 120                 125

Gln Val Gln Leu Val Gln Ser Gly Ala Glu Val Lys Lys Pro Gly Glu
130                 135                 140

Ser Leu Lys Ile Ser Cys Lys Gly Ser Gly Tyr Asn Phe Ser Asn Lys
145                 150                 155                 160

Trp Ile Gly Trp Val Arg Gln Leu Pro Gly Arg Gly Leu Glu Trp Ile
                165                 170                 175

Ala Ile Ile Tyr Pro Gly Tyr Ser Asp Ile Thr Tyr Ser Pro Ser Phe
            180                 185                 190

Gln Gly Arg Val Thr Ile Ser Ala Asp Thr Ser Ile Asn Thr Ala Tyr
        195                 200                 205

Leu His Trp His Ser Leu Lys Ala Ser Asp Thr Ala Met Tyr Tyr Cys
    210                 215                 220

Val Arg His Thr Ala Leu Ala Gly Phe Asp Tyr Trp Gly Leu Gly Thr
225                 230                 235                 240

Leu Val Thr Val Ser Ser
                245
```

<210> SEQ ID NO 73
<211> LENGTH: 738
<212> TYPE: DNA
<213> ORGANISM: Homo sapiens

<400> SEQUENCE: 73

```
gacatccaga tgacccagtc tccttccacc ctgtctgcat ctgtaggaga cagagtcaca      60
atcacttgcc gggccagtca gaatatcaat aagtggctgg cctggtatca gcagagacca     120
gggaaagccc ctcagctcct gatctataag gcgtctagtt tagaaagtgg ggtcccatct     180
aggttcagcg gcagtggatc tgggacagaa tacactctca ccatcagcag cctgcagcct     240
gatgattttg caacttatta ctgccaacaa tataatagtt atgcgacgtt cggccaaggg     300
```

```
accaaggtgg aaatcaaacg ttctagaggt ggtggtggta gcggcggcgg cggctctggt    360
ggtggtggat ccctcgagat ggcccaggtg cagctggtgc agtctggagc agaggtgaaa    420
aagcccggag agtctctgaa gatctcctgt aagggttctg gctacaactt tagcaacaag    480
tggatcggct gggtgcgcca attgcccggg agaggcctgg agtggatagc aatcatctat    540
cccggttact cggacatcac ctacagcccg tccttccaag gccgcgtcac catctccgcc    600
gacacgtcca ttaacaccgc ctacctgcac tggcacagcc tgaaggcctc ggacaccgcc    660
atgtattatt gtgtgcgaca cacagctttg gccggctttg actactgggg cctgggcacc    720
ctggtcaccg tctcctca                                                  738

<210> SEQ ID NO 74
<211> LENGTH: 10
<212> TYPE: PRT
<213> ORGANISM: Homo sapiens

<400> SEQUENCE: 74

Gly Phe Thr Phe Asp Asp Tyr Gly Met Ser
1               5                   10

<210> SEQ ID NO 75
<211> LENGTH: 17
<212> TYPE: PRT
<213> ORGANISM: Homo sapiens

<400> SEQUENCE: 75

Gly Ile Asn Trp Asn Gly Gly Ser Thr Gly Tyr Ala Asp Ser Val Arg
1               5                   10                  15

Gly

<210> SEQ ID NO 76
<211> LENGTH: 12
<212> TYPE: PRT
<213> ORGANISM: Homo sapiens

<400> SEQUENCE: 76

Glu Arg Gly Tyr Gly Tyr His Asp Pro His Asp Tyr
1               5                   10

<210> SEQ ID NO 77
<211> LENGTH: 30
<212> TYPE: DNA
<213> ORGANISM: Homo sapiens

<400> SEQUENCE: 77
gggttcacct ttgatgatta tggcatgagc                                     30

<210> SEQ ID NO 78
<211> LENGTH: 51
<212> TYPE: DNA
<213> ORGANISM: Homo sapiens

<400> SEQUENCE: 78
ggtattaatt ggaatggtgg tagcacaggt tatgcagact ctgtgagggg c             51

<210> SEQ ID NO 79
<211> LENGTH: 36
<212> TYPE: DNA
<213> ORGANISM: Homo sapiens

<400> SEQUENCE: 79
```

```
gagcgtggct acgggtacca tgatccccat gactac                                    36
```

<210> SEQ ID NO 80
<211> LENGTH: 11
<212> TYPE: PRT
<213> ORGANISM: Homo sapiens

<400> SEQUENCE: 80

Gly Arg Asn Asn Ile Gly Ser Lys Ser Val His
1               5                   10

<210> SEQ ID NO 81
<211> LENGTH: 7
<212> TYPE: PRT
<213> ORGANISM: Homo sapiens

<400> SEQUENCE: 81

Asp Asp Ser Asp Arg Pro Ser
1               5

<210> SEQ ID NO 82
<211> LENGTH: 11
<212> TYPE: PRT
<213> ORGANISM: Homo sapiens

<400> SEQUENCE: 82

Gln Val Trp Asp Ser Ser Ser Asp His Val Val
1               5                   10

<210> SEQ ID NO 83
<211> LENGTH: 33
<212> TYPE: DNA
<213> ORGANISM: Homo sapiens

<400> SEQUENCE: 83

```
gggagaaaca acattggaag taaaagtgtg cac                                       33
```

<210> SEQ ID NO 84
<211> LENGTH: 21
<212> TYPE: DNA
<213> ORGANISM: Homo sapiens

<400> SEQUENCE: 84

```
gatgatagcg accggccctc a                                                    21
```

<210> SEQ ID NO 85
<211> LENGTH: 33
<212> TYPE: DNA
<213> ORGANISM: Homo sapiens

<400> SEQUENCE: 85

```
caggtgtggg atagtagtag tgatcatgtg gta                                       33
```

<210> SEQ ID NO 86
<211> LENGTH: 121
<212> TYPE: PRT
<213> ORGANISM: Homo sapiens

<400> SEQUENCE: 86

Glu Val Gln Leu Val Gln Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
            35                  40                  45

Ser Gly Ile Asn Trp Asn Gly Ser Thr Gly Tyr Ala Asp Ser Val
 50                  55                  60

Arg Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Arg Glu Arg Gly Tyr Gly Tyr His Asp Pro His Asp Tyr Trp Gly
            100                 105                 110

Gln Gly Thr Leu Val Thr Val Ser Ser
            115                 120

<210> SEQ ID NO 87
<211> LENGTH: 363
<212> TYPE: DNA
<213> ORGANISM: Homo sapiens

<400> SEQUENCE: 87
gaagtgcagc tggtgcagtc tgggggaggt gtggtacggc ctgggggtc cctgagactc      60 tcctgtgcag cctctgggtt caccttttgat gattatggca tgagctgggt ccgccaagct    120
ccagggaagg gctggagtg gtctctggt attaattgga atggtggtag cacaggttat      180
gcagactctg tgaggggccg attcaccatc tccagagaca acgccaagaa ctccctgtat    240
ctgcaaatga acagtctgag agccgaggac acggccttgt attactgtgc gagagagcgt    300
ggctacgggt accatgatcc ccatgactac tggggccaag gcaccctggt gaccgtctcc    360
tca                                                                   363

<210> SEQ ID NO 88
<211> LENGTH: 109
<212> TYPE: PRT
<213> ORGANISM: Homo sapiens

<400> SEQUENCE: 88

Gln Ser Val Val Thr Gln Pro Pro Ser Val Ser Val Ala Pro Gly Lys
 1               5                   10                  15

Thr Ala Arg Ile Thr Cys Gly Arg Asn Asn Ile Gly Ser Lys Ser Val
            20                  25                  30

His Trp Tyr Gln Gln Lys Pro Gly Gln Ala Pro Val Leu Val Val Tyr
            35                  40                  45

Asp Asp Ser Asp Arg Pro Ser Gly Ile Pro Glu Arg Phe Ser Gly Ser
 50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Ser Asp His
                 85                  90                  95

Val Val Phe Gly Gly Gly Thr Lys Leu Thr Val Leu Gly
            100                 105

<210> SEQ ID NO 89
<211> LENGTH: 327
<212> TYPE: DNA
<213> ORGANISM: Homo sapiens

<400> SEQUENCE: 89
cagtctgtcg tgacgcagcc gccctcggtg tcagtggccc caggaaagac ggccaggatt      60

```
acctgtggga gaaacaacat tggaagtaaa agtgtgcact ggtaccagca gaagccaggc    120
caggcccctg tgctggtcgt ctatgatgat agcgaccggc cctcaggat ccctgagcga     180 ttctctggct ccaactctgg gaacacggcc accctgacca tcagcagggt cgaagccggg    240
gatgaggccg actattactg tcaggtgtgg gatagtagta gtgatcatgt ggtattcggc    300
ggagggacca agctgaccgt cctaggt                                        327
```

<210> SEQ ID NO 90
<211> LENGTH: 249
<212> TYPE: PRT
<213> ORGANISM: Homo sapiens

<400> SEQUENCE: 90

```
Gln Ser Val Val Thr Gln Pro Pro Ser Val Ser Val Ala Pro Gly Lys
1               5                   10                  15

Thr Ala Arg Ile Thr Cys Gly Arg Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu Gly Ser Arg Gly
            100                 105                 110

Gly Gly Gly Ser Gly Gly Gly Gly Ser Gly Gly Ser Leu Glu Met Ala
        115                 120                 125

Glu Val Gln Leu Val Gln Ser Gly Gly Gly Val Val Arg Pro Gly Gly
    130                 135                 140

Ser Leu Arg Leu Ser Cys Ala Ala Ser Gly Phe Thr Phe Asp Asp Tyr
145                 150                 155                 160

Gly Met Ser Trp Val Arg Gln Ala Pro Gly Lys Gly Leu Glu Trp Val
                165                 170                 175

Ser Gly Ile Asn Trp Asn Gly Gly Ser Thr Gly Tyr Ala Asp Ser Val
            180                 185                 190

Arg Gly Arg Phe Thr Ile Ser Arg Asp Asn Ala Lys Asn Ser Leu Tyr
        195                 200                 205

Leu Gln Met Asn Ser Leu Arg Ala Glu Asp Thr Ala Leu Tyr Tyr Cys
    210                 215                 220

Ala Arg Glu Arg Gly Tyr Gly Tyr His Asp Pro His Asp Tyr Trp Gly
225                 230                 235                 240

Gln Gly Thr Leu Val Thr Val Ser Ser
                245
```

<210> SEQ ID NO 91
<211> LENGTH: 747
<212> TYPE: DNA
<213> ORGANISM: Homo sapiens

<400> SEQUENCE: 91

```
cagtctgtcg tgacgcagcc gccctcggtg tcagtggccc caggaaagac ggccaggatt     60
acctgtggga gaaacaacat tggaagtaaa agtgtgcact ggtaccagca gaagccaggc    120
```

| | |
|---|---|
| caggcccctg tgctggtcgt ctatgatgat agcgaccggc cctcagggat ccctgagcga | 180 |
| ttctctggct ccaactctgg gaacacggcc accctgacca tcagcagggt cgaagccggg | 240 |
| gatgaggccg actattactg tcaggtgtgg gatagtagta gtgatcatgt ggtattcggc | 300 |
| ggagggacca agctgaccgt cctaggttct agaggtggtg gtggtagcgg cggcggcggc | 360 |
| tctggtggat ccctcgagat ggccgaagtg cagctggtgc agtctggggg aggtgtggta | 420 |
| cggcctgggg ggtccctgag actctcctgt gcagcctctg gcttcacctt tgatgattat | 480 |
| ggcatgagct gggtccgcca agctccaggg aaggggctgg agtgggtctc tggtattaat | 540 |
| tggaatggtg gtagcacagg ttatgcagac tctgtgaggg gccgattcac catctcccaga | 600 |
| gacaacgcca agaactccct gtatctgcaa atgaacagtc tgagagccga ggacacggcc | 660 |
| ttgtattact gtgcgagaga gcgtggctac gggtaccatg atccccatga ctactggggc | 720 |
| caaggcaccc tggtgaccgt ctcctca | 747 |

<210> SEQ ID NO 92
<211> LENGTH: 10
<212> TYPE: PRT
<213> ORGANISM: Homo sapiens

<400> SEQUENCE: 92

Gly Phe Ser Val Ser Gly Thr Tyr Met Gly
1               5                   10

<210> SEQ ID NO 93
<211> LENGTH: 16
<212> TYPE: PRT
<213> ORGANISM: Homo sapiens

<400> SEQUENCE: 93

Leu Leu Tyr Ser Gly Gly Gly Thr Tyr His Pro Ala Ser Leu Gln Gly
1               5                   10                  15

<210> SEQ ID NO 94
<211> LENGTH: 10
<212> TYPE: PRT
<213> ORGANISM: Homo sapiens

<400> SEQUENCE: 94

Gly Gly Ala Gly Gly Gly His Phe Asp Ser
1               5                   10

<210> SEQ ID NO 95
<211> LENGTH: 30
<212> TYPE: DNA
<213> ORGANISM: Homo sapiens

<400> SEQUENCE: 95
gggttctccg tcagtggcac ctacatgggc                                    30

<210> SEQ ID NO 96
<211> LENGTH: 48
<212> TYPE: DNA
<213> ORGANISM: Homo sapiens

<400> SEQUENCE: 96
cttctttata gtggtggcgg cacataccac ccagcgtccc tgcagggc                48

<210> SEQ ID NO 97
<211> LENGTH: 30
<212> TYPE: DNA

<210> SEQ ID NO 97
<211> LENGTH: 30
<212> TYPE: DNA
<213> ORGANISM: Homo sapiens

<400> SEQUENCE: 97
ggaggggcag gaggtggcca ctttgactcc                               30

<210> SEQ ID NO 98
<211> LENGTH: 14
<212> TYPE: PRT
<213> ORGANISM: Homo sapiens

<400> SEQUENCE: 98

Thr Gly Ser Ser Ser Asn Ile Gly Ala Gly Tyr Asp Val His
1               5                   10

<210> SEQ ID NO 99
<211> LENGTH: 7
<212> TYPE: PRT
<213> ORGANISM: Homo sapiens

<400> SEQUENCE: 99

Gly Asn Ser Asn Arg Pro Ser
1               5

<210> SEQ ID NO 100
<211> LENGTH: 11
<212> TYPE: PRT
<213> ORGANISM: Homo sapiens

<400> SEQUENCE: 100

Ala Ala Trp Asp Asp Ser Leu Asn Gly Tyr Val
1               5                   10

<210> SEQ ID NO 101
<211> LENGTH: 42
<212> TYPE: DNA
<213> ORGANISM: Homo sapiens

<400> SEQUENCE: 101
actgggagca gctccaacat cggggcaggt tatgatgtac ac                 42

<210> SEQ ID NO 102
<211> LENGTH: 21
<212> TYPE: DNA
<213> ORGANISM: Homo sapiens

<400> SEQUENCE: 102
ggtaacagca atcggccctc a                                        21

<210> SEQ ID NO 103
<211> LENGTH: 33
<212> TYPE: DNA
<213> ORGANISM: Homo sapiens

<400> SEQUENCE: 103
gcagcatggg atgacagcct gaatggttat gtc                           33

<210> SEQ ID NO 104
<211> LENGTH: 118
<212> TYPE: PRT
<213> ORGANISM: Homo sapiens

<400> SEQUENCE: 104

Glu Val Gln Leu Val Glu Thr Gly Gly Gly Leu Leu Gln Pro Gly Gly
1               5                   10                  15

Ser Leu Arg Leu Ser Cys Ala Ala Ser Gly Phe Ser Val Ser Gly Thr
            20                  25                  30

Tyr Met Gly Trp Val Arg Gln Ala Pro Gly Lys Gly Leu Glu Trp Val
        35                  40                  45

Ala Leu Leu Tyr Ser Gly Gly Thr Tyr His Pro Ala Ser Leu Gln
50                  55                  60

Gly Arg Phe Ile Val Ser Arg Asp Ser Ser Lys Asn Met Val Tyr Leu
65                  70                  75                  80

Gln Met Asn Ser Leu Lys Ala Glu Asp Thr Ala Val Tyr Tyr Cys Ala
                85                  90                  95

Lys Gly Gly Ala Gly Gly Gly His Phe Asp Ser Trp Gly Gln Gly Thr
            100                 105                 110

Leu Val Thr Val Ser Ser
        115

<210> SEQ ID NO 105
<211> LENGTH: 354
<212> TYPE: DNA
<213> ORGANISM: Homo sapiens

<400> SEQUENCE: 105
gaggtgcagc tggtggagac cggaggaggc ttgctccagc cggggggggtc cctcagactc    60 tcctgtgcag cctctgggtt ctccgtcagt ggcacctaca tgggctgggt ccgccaggct   120
ccagggaagg gactggagtg ggtcgcactt ctttatagtg gtggcggcac ataccaccca   180
gcgtccctgc aggccgatt catcgtctcc agagacagct ccaagaatat ggtctatctt   240
caaatgaata gcctgaaagc cgaggacacg gccgtctatt actgtgcgaa aggaggggca   300
ggaggtggcc actttgactc ctggggccaa ggcaccctgg tgaccgtctc ctca         354

<210> SEQ ID NO 106
<211> LENGTH: 112
<212> TYPE: PRT
<213> ORGANISM: Homo sapiens

<400> SEQUENCE: 106

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
50                  55                  60

Ser Gly Ser Lys Ser Gly Thr Ser Ala Ser Leu Ala Ile Ser Gly Leu
65                  70                  75                  80

Gln Ser Glu Asp Glu Ala Asp Tyr Tyr Cys Ala Ala Trp Asp Asp Ser
                85                  90                  95

Leu Asn Gly Tyr Val Phe Gly Thr Gly Thr Lys Leu Thr Val Leu Gly
            100                 105                 110

<210> SEQ ID NO 107
<211> LENGTH: 336
<212> TYPE: DNA
<213> ORGANISM: Homo sapiens

<400> SEQUENCE: 107

```
cagtctgtgt tgacgcagcc gccctcagtg tctggggccc cagggcagag ggtcaccatc    60
tcctgcactg ggagcagctc caacatcggg gcaggttatg atgtacactg gtaccagcag   120
cttccaggaa cagcccccaa actcctcatc tatggtaaca gcaatcggcc ctcaggggtc   180
cctgaccgat tctctggctc caagtctggc acctcagcct ccctggccat cagtgggctc   240
cagtctgagg atgaggctga ttattactgt gcagcatggg atgacagcct gaatggttat   300
gtcttcggaa ctgggaccaa gctgaccgtc ctaggt                             336
```

```
<210> SEQ ID NO 108
<211> LENGTH: 251
<212> TYPE: PRT
<213> ORGANISM: Homo sapiens

<400> SEQUENCE: 108
```

```
Gln Ser Val Leu Thr Gln Pro Pro Ser Val Ser Gly Ala Pro Gly Gln
 1               5                  10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Gln Ser Glu Asp Glu Ala Asp Tyr Tyr Cys Ala Ala Trp Asp Asp Ser
                85                  90                  95

Leu Asn Gly Tyr Val Phe Gly Thr Gly Thr Lys Leu Thr Val Leu Gly
            100                 105                 110

Ser Arg Gly Gly Gly Gly Ser Gly Gly Gly Gly Ser Gly Gly Gly Gly
        115                 120                 125

Ser Leu Glu Met Ala Glu Val Gln Leu Val Glu Thr Gly Gly Gly Leu
    130                 135                 140

Leu Gln Pro Gly Gly Ser Leu Arg Leu Ser Cys Ala Ala Ser Gly Phe
145                 150                 155                 160

Ser Val Ser Gly Thr Tyr Met Gly Trp Val Arg Gln Ala Pro Gly Lys
                165                 170                 175

Gly Leu Glu Trp Val Ala Leu Leu Tyr Ser Gly Gly Thr Tyr His
            180                 185                 190

Pro Ala Ser Leu Gln Gly Arg Phe Ile Val Ser Arg Asp Ser Ser Lys
        195                 200                 205

Asn Met Val Tyr Leu Gln Met Asn Ser Leu Lys Ala Glu Asp Thr Ala
    210                 215                 220

Val Tyr Tyr Cys Ala Lys Gly Gly Ala Gly Gly His Phe Asp Ser
225                 230                 235                 240

Trp Gly Gln Gly Thr Leu Val Thr Val Ser Ser
                245                 250
```

```
<210> SEQ ID NO 109
<211> LENGTH: 753
<212> TYPE: DNA
<213> ORGANISM: Homo sapiens

<400> SEQUENCE: 109
cagtctgtgt tgacgcagcc gccctcagtg tctggggccc cagggcagag ggtcaccatc    60
tcctgcactg ggagcagctc caacatcggg gcaggttatg atgtacactg gtaccagcag   120
```

```
cttccaggaa cagcccccaa actcctcatc tatggtaaca gcaatcggcc ctcagggtc      180 cctgaccgat tctctggctc caagtctggc acctcagcct ccctggccat cagtgggctc     240
cagtctgagg atgaggctga ttattactgt gcagcatggg atgacagcct gaatggttat     300
gtcttcggaa ctgggaccaa gctgaccgtc ctaggttcta gaggtggtgg tggtagcggc     360
ggcggcggct ctggtggtgg tggatccctc gagatggccg aggtgcagct ggtggagacc     420
ggaggaggct tgctccagcc gggggggtcc ctcagactct cctgtgcagc ctctgggttc     480
tccgtcagtg gcacctacat gggctgggtc cgccaggctc agggaaggg actggagtgg      540 gtcgcacttc tttatagtgg tggcggcaca taccacccag cgtccctgca gggccgattc     600
atcgtctcca gagacagctc caagaatatg gtctatcttc aaatgaatag cctgaaagcc     660
gaggacacgg ccgtctatta ctgtgcgaaa ggaggggcag gaggtggcca ctttgactcc     720
tggggccaag gcaccctggt gaccgtctcc tca                                  753
```

<210> SEQ ID NO 110
<211> LENGTH: 9
<212> TYPE: PRT
<213> ORGANISM: Homo sapiens

<400> SEQUENCE: 110

Ala Met Phe Pro Asn Ala Pro Tyr Leu
1               5

<210> SEQ ID NO 111
<211> LENGTH: 9
<212> TYPE: PRT
<213> ORGANISM: Homo sapiens

<400> SEQUENCE: 111

Arg Met Ala Pro Asn Ala Pro Tyr Leu
1               5

<210> SEQ ID NO 112
<211> LENGTH: 9
<212> TYPE: PRT
<213> ORGANISM: Homo sapiens

<400> SEQUENCE: 112

Arg Met Phe Ala Asn Ala Pro Tyr Leu
1               5

<210> SEQ ID NO 113
<211> LENGTH: 9
<212> TYPE: PRT
<213> ORGANISM: Homo sapiens

<400> SEQUENCE: 113

Arg Met Phe Pro Ala Ala Pro Tyr Leu
1               5

<210> SEQ ID NO 114
<211> LENGTH: 9
<212> TYPE: PRT
<213> ORGANISM: Homo sapiens

<400> SEQUENCE: 114

Arg Met Phe Pro Asn Ala Ala Tyr Leu
1               5

```
<210> SEQ ID NO 115
<211> LENGTH: 9
<212> TYPE: PRT
<213> ORGANISM: Homo sapiens

<400> SEQUENCE: 115

Arg Met Phe Pro Asn Ala Pro Ala Leu
1               5

<210> SEQ ID NO 116
<211> LENGTH: 9
<212> TYPE: PRT
<213> ORGANISM: Homo sapiens

<400> SEQUENCE: 116

Ile Leu Ser Leu Glu Leu Met Lys Leu
1               5

<210> SEQ ID NO 117
<211> LENGTH: 9
<212> TYPE: PRT
<213> ORGANISM: Homo sapiens

<400> SEQUENCE: 117

Gln Leu Gln Asn Pro Ser Tyr Asp Lys
1               5

<210> SEQ ID NO 118
<211> LENGTH: 449
<212> TYPE: PRT
<213> ORGANISM: Homo sapiens

<400> SEQUENCE: 118

Met Gly Ser Asp Val Arg Asp Leu Asn Ala Leu Leu Pro Ala Val Pro
1               5                   10                  15

Ser Leu Gly Gly Gly Gly Gly Cys Ala Leu Pro Val Ser Gly Ala Ala
                20                  25                  30

Gln Trp Ala Pro Val Leu Asp Phe Ala Pro Pro Gly Ala Ser Ala Tyr
            35                  40                  45

Gly Ser Leu Gly Gly Pro Ala Pro Pro Ala Pro Pro Pro Pro Pro Pro
    50                  55                  60

Pro Pro Pro Pro His Ser Phe Ile Lys Gln Glu Pro Ser Trp Gly Gly
65                  70                  75                  80

Ala Glu Pro His Glu Glu Gln Cys Leu Ser Ala Phe Thr Val His Phe
                85                  90                  95

Ser Gly Gln Phe Thr Gly Thr Ala Gly Ala Cys Arg Tyr Gly Pro Phe
            100                 105                 110

Gly Pro Pro Pro Ser Gln Ala Ser Ser Gly Gln Ala Arg Met Phe
        115                 120                 125

Pro Asn Ala Pro Tyr Leu Pro Ser Cys Leu Glu Ser Gln Pro Ala Ile
    130                 135                 140

Arg Asn Gln Gly Tyr Ser Thr Val Thr Phe Asp Gly Thr Pro Ser Tyr
145                 150                 155                 160

Gly His Thr Pro Ser His His Ala Ala Gln Phe Pro Asn His Ser Phe
                165                 170                 175

Lys His Glu Asp Pro Met Gly Gln Gln Gly Ser Leu Gly Glu Gln Gln
            180                 185                 190

Tyr Ser Val Pro Pro Pro Val Tyr Gly Cys His Thr Pro Thr Asp Ser
        195                 200                 205
```

```
Cys Thr Gly Ser Gln Ala Leu Leu Arg Thr Pro Tyr Ser Ser Asp
            210                 215                 220

Asn Leu Tyr Gln Met Thr Ser Gln Leu Glu Cys Met Thr Trp Asn Gln
225                 230                 235                 240

Met Asn Leu Gly Ala Thr Leu Lys Gly Val Ala Ala Gly Ser Ser Ser
                245                 250                 255

Ser Val Lys Trp Thr Glu Gly Gln Ser Asn His Ser Thr Gly Tyr Glu
            260                 265                 270

Ser Asp Asn His Thr Thr Pro Ile Leu Cys Gly Ala Gln Tyr Arg Ile
            275                 280                 285

His Thr His Gly Val Phe Arg Gly Ile Gln Asp Val Arg Arg Val Pro
            290                 295                 300

Gly Val Ala Pro Thr Leu Val Arg Ser Ala Ser Glu Thr Ser Glu Lys
305                 310                 315                 320

Arg Pro Phe Met Cys Ala Tyr Pro Gly Cys Asn Lys Arg Tyr Phe Lys
                325                 330                 335

Leu Ser His Leu Gln Met His Ser Arg Lys His Thr Gly Glu Lys Pro
            340                 345                 350

Tyr Gln Cys Asp Phe Lys Asp Cys Glu Arg Arg Phe Ser Arg Ser Asp
            355                 360                 365

Gln Leu Lys Arg His Gln Arg Arg His Thr Gly Val Lys Pro Phe Gln
370                 375                 380

Cys Lys Thr Cys Gln Arg Lys Phe Ser Arg Ser Asp His Leu Lys Thr
385                 390                 395                 400

His Thr Arg Thr His Thr Gly Lys Thr Ser Glu Lys Pro Phe Ser Cys
                405                 410                 415

Arg Trp Pro Ser Cys Gln Lys Lys Phe Ala Arg Ser Asp Glu Leu Val
            420                 425                 430

Arg His His Asn Met His Gln Arg Asn Met Thr Lys Leu Gln Leu Ala
            435                 440                 445

Leu

<210> SEQ ID NO 119
<211> LENGTH: 7
<212> TYPE: PRT
<213> ORGANISM: Homo sapiens

<400> SEQUENCE: 119

Ser Asn Ala Val Ala Trp Asn
1               5

<210> SEQ ID NO 120
<211> LENGTH: 13
<212> TYPE: PRT
<213> ORGANISM: Homo sapiens

<400> SEQUENCE: 120

Arg Thr Tyr Arg Gly Ser Thr Tyr Tyr Ala Leu Ser Val
1               5                   10

<210> SEQ ID NO 121
<211> LENGTH: 8
<212> TYPE: PRT
<213> ORGANISM: Homo sapiens

<400> SEQUENCE: 121

Gly Ser Asn Ser Ala Phe Asp Phe
1               5
```

```
<210> SEQ ID NO 122
<211> LENGTH: 7
<212> TYPE: PRT
<213> ORGANISM: Homo sapiens

<400> SEQUENCE: 122

Ser Asn Ser Ala Ala Trp Asn
1               5

<210> SEQ ID NO 123
<211> LENGTH: 16
<212> TYPE: PRT
<213> ORGANISM: Homo sapiens

<400> SEQUENCE: 123

Arg Thr Tyr Tyr Gly Ser Lys Trp Tyr Asn Asp Tyr Ala Val Ser Val
1               5                   10                  15

<210> SEQ ID NO 124
<211> LENGTH: 9
<212> TYPE: PRT
<213> ORGANISM: Homo sapiens

<400> SEQUENCE: 124

Gly Arg Leu Gly Asp Ala Phe Asp Ile
1               5

<210> SEQ ID NO 125
<211> LENGTH: 7
<212> TYPE: PRT
<213> ORGANISM: Homo sapiens

<400> SEQUENCE: 125

Ser Asp Gly Ala Ala Trp Asn
1               5

<210> SEQ ID NO 126
<211> LENGTH: 16
<212> TYPE: PRT
<213> ORGANISM: Homo sapiens

<400> SEQUENCE: 126

Arg Thr Tyr Tyr Arg Ser Lys Trp Tyr Asn Asp Tyr Ala Val Ser Val
1               5                   10                  15

<210> SEQ ID NO 127
<211> LENGTH: 9
<212> TYPE: PRT
<213> ORGANISM: Homo sapiens

<400> SEQUENCE: 127

Gly Asp Tyr Tyr Tyr Gly Met Asp Val
1               5

<210> SEQ ID NO 128
<211> LENGTH: 7
<212> TYPE: PRT
<213> ORGANISM: Homo sapiens

<400> SEQUENCE: 128

Ser Asn Ala Ala Ala Trp Asn
1               5
```

```
<210> SEQ ID NO 129
<211> LENGTH: 16
<212> TYPE: PRT
<213> ORGANISM: Homo sapiens

<400> SEQUENCE: 129

Arg Thr Tyr Tyr Gly Ser Lys Trp Tyr Asn Asp Tyr Ala Val Ser Val
1               5                   10                  15

<210> SEQ ID NO 130
<211> LENGTH: 5
<212> TYPE: PRT
<213> ORGANISM: Homo sapiens

<400> SEQUENCE: 130

Gly Ala Phe Asp Ile
1               5

<210> SEQ ID NO 131
<211> LENGTH: 5
<212> TYPE: PRT
<213> ORGANISM: Homo sapiens

<400> SEQUENCE: 131

Ser Tyr Trp Ile Ser
1               5

<210> SEQ ID NO 132
<211> LENGTH: 17
<212> TYPE: PRT
<213> ORGANISM: Homo sapiens

<400> SEQUENCE: 132

Arg Ile Asp Pro Ser Asp Ser Tyr Thr Asn Tyr Ser Pro Ser Phe Gln
1               5                   10                  15

Gly

<210> SEQ ID NO 133
<211> LENGTH: 9
<212> TYPE: PRT
<213> ORGANISM: Homo sapiens

<400> SEQUENCE: 133

Gly Asp Tyr Asp Phe Tyr Leu Asp Pro
1               5

<210> SEQ ID NO 134
<211> LENGTH: 5
<212> TYPE: PRT
<213> ORGANISM: Homo sapiens

<400> SEQUENCE: 134

Ser Tyr Gly Ile Ser
1               5

<210> SEQ ID NO 135
<211> LENGTH: 17
<212> TYPE: PRT
<213> ORGANISM: Homo sapiens

<400> SEQUENCE: 135

Trp Ile Ser Ala Tyr Asn Gly Asn Thr Asn Tyr Ala Gln Lys Leu Gln
1               5                   10                  15

Gly
```

<210> SEQ ID NO 136
<211> LENGTH: 17
<212> TYPE: PRT
<213> ORGANISM: Homo sapiens

<400> SEQUENCE: 136

Asp Leu Tyr Ser Ser Gly Trp Tyr Glu Ser Tyr Tyr Tyr Gly Met Asp
1               5                   10                  15
Val

<210> SEQ ID NO 137
<211> LENGTH: 5
<212> TYPE: PRT
<213> ORGANISM: Homo sapiens

<400> SEQUENCE: 137

Ser Tyr Ala Ile Ser
1               5

<210> SEQ ID NO 138
<211> LENGTH: 17
<212> TYPE: PRT
<213> ORGANISM: Homo sapiens

<400> SEQUENCE: 138

Gly Ile Ile Pro Ile Phe Gly Thr Ala Asn Tyr Ala Gln Lys Phe Gln
1               5                   10                  15
Gly

<210> SEQ ID NO 139
<211> LENGTH: 10
<212> TYPE: PRT
<213> ORGANISM: Homo sapiens

<400> SEQUENCE: 139

Arg Ile Pro Pro Tyr Tyr Gly Met Asp Val
1               5                   10

<210> SEQ ID NO 140
<211> LENGTH: 17
<212> TYPE: PRT
<213> ORGANISM: Homo sapiens

<400> SEQUENCE: 140

Trp Ile Ser Ala His Asn Gly Asn Thr Asn Tyr Ala Gln Lys Leu Gln
1               5                   10                  15
Gly

<210> SEQ ID NO 141
<211> LENGTH: 10
<212> TYPE: PRT
<213> ORGANISM: Homo sapiens

<400> SEQUENCE: 141

Asp Arg Val Trp Phe Gly Asp Leu Ser Asp
1               5                   10

<210> SEQ ID NO 142
<211> LENGTH: 17
<212> TYPE: PRT
<213> ORGANISM: Homo sapiens

<400> SEQUENCE: 142

Gly Ile Ile Pro Ile Phe Gly Thr Ala Asn Tyr Ala Gln Lys Glu Gln
1               5                   10                  15

Gly

<210> SEQ ID NO 143
<211> LENGTH: 12
<212> TYPE: PRT
<213> ORGANISM: Homo sapiens

<400> SEQUENCE: 143

Asn Tyr Asp Phe Trp Ser Gly Asp Ala Phe Asp Ile
1               5                   10

<210> SEQ ID NO 144
<211> LENGTH: 12
<212> TYPE: PRT
<213> ORGANISM: Homo sapiens

<400> SEQUENCE: 144

Ile Pro Gly Thr Asn Tyr Ala Gln Lys Phe Gln Gly
1               5                   10

<210> SEQ ID NO 145
<211> LENGTH: 6
<212> TYPE: PRT
<213> ORGANISM: Homo sapiens

<400> SEQUENCE: 145

Phe Tyr Gly Met Asp Val
1               5

<210> SEQ ID NO 146
<211> LENGTH: 5
<212> TYPE: PRT
<213> ORGANISM: Homo sapiens

<400> SEQUENCE: 146

Asp Tyr Gly Met Ser
1               5

<210> SEQ ID NO 147
<211> LENGTH: 15
<212> TYPE: PRT
<213> ORGANISM: Homo sapiens

<400> SEQUENCE: 147

Gly Ile Asn Trp Asn Gly Gly Ser Thr Gly Tyr Ala Asp Ser Val
1               5                   10                  15

<210> SEQ ID NO 148
<211> LENGTH: 12
<212> TYPE: PRT
<213> ORGANISM: Homo sapiens

<400> SEQUENCE: 148

Glu Arg Gly Tyr Gly Tyr His Asp Pro His Asp Tyr
1               5                   10

<210> SEQ ID NO 149
<211> LENGTH: 5
<212> TYPE: PRT
<213> ORGANISM: Homo sapiens

<400> SEQUENCE: 149

Asn Tyr Thr Met Asn
1               5

<210> SEQ ID NO 150
<211> LENGTH: 15
<212> TYPE: PRT
<213> ORGANISM: Homo sapiens

<400> SEQUENCE: 150

Ser Ile Ser Leu Ser Gly Ala Tyr Ile Tyr Tyr Ala Asp Ser Leu
1               5                   10                  15

<210> SEQ ID NO 151
<211> LENGTH: 13
<212> TYPE: PRT
<213> ORGANISM: Homo sapiens

<400> SEQUENCE: 151

Glu Gly Tyr Ser Ser Val Tyr Asp Ala Phe Asp Leu
1               5                   10

<210> SEQ ID NO 152
<211> LENGTH: 5
<212> TYPE: PRT
<213> ORGANISM: Homo sapiens

<400> SEQUENCE: 152

Ser Tyr Gly Met His
1               5

<210> SEQ ID NO 153
<211> LENGTH: 15
<212> TYPE: PRT
<213> ORGANISM: Homo sapiens

<400> SEQUENCE: 153

Gly Ile Leu Ser Asp Gly Gly Lys Asp Tyr Tyr Val Asp Ser Val
1               5                   10                  15

<210> SEQ ID NO 154
<211> LENGTH: 12
<212> TYPE: PRT
<213> ORGANISM: Homo sapiens

<400> SEQUENCE: 154

Cys Ser Ser Asn Tyr Gly Asn Asp Ala Phe Asp Ile
1               5                   10

<210> SEQ ID NO 155
<211> LENGTH: 5
<212> TYPE: PRT
<213> ORGANISM: Homo sapiens

<400> SEQUENCE: 155

Thr Tyr Ser Met Asn
1               5

<210> SEQ ID NO 156
<211> LENGTH: 15
<212> TYPE: PRT
<213> ORGANISM: Homo sapiens

<400> SEQUENCE: 156

Ser Ile Ser Ser Gly Ala Tyr Ser Ile Phe Tyr Ala Asp Ser Val
1               5                   10                  15

<210> SEQ ID NO 157
<211> LENGTH: 13
<212> TYPE: PRT
<213> ORGANISM: Homo sapiens

<400> SEQUENCE: 157

Asp Gln Tyr Tyr Gly Asp Lys Trp Asp Ala Phe Asp Ile
1               5                   10

<210> SEQ ID NO 158
<211> LENGTH: 5
<212> TYPE: PRT
<213> ORGANISM: Homo sapiens

<400> SEQUENCE: 158

Ser Tyr Gly Met Asn
1               5

<210> SEQ ID NO 159
<211> LENGTH: 14
<212> TYPE: PRT
<213> ORGANISM: Homo sapiens

<400> SEQUENCE: 159

Ser Ile Ser Ser Gly Gly Ser Ile Tyr Tyr Ala Asp Ser Val
1               5                   10

<210> SEQ ID NO 160
<211> LENGTH: 9
<212> TYPE: PRT
<213> ORGANISM: Homo sapiens

<400> SEQUENCE: 160

Glu Tyr Tyr Trp Asp Ala Phe Asp Ile
1               5

<210> SEQ ID NO 161
<211> LENGTH: 14
<212> TYPE: PRT
<213> ORGANISM: Homo sapiens

<400> SEQUENCE: 161

Cys Ser Gly Ser Ser Ser Asn Ile Gly Ser Asn Thr Val Asn
1               5                   10

<210> SEQ ID NO 162
<211> LENGTH: 8
<212> TYPE: PRT
<213> ORGANISM: Homo sapiens

<400> SEQUENCE: 162

Ser Asn Asn Gln Arg Pro Ser Gly
1               5

<210> SEQ ID NO 163
<211> LENGTH: 13
<212> TYPE: PRT
<213> ORGANISM: Homo sapiens

<400> SEQUENCE: 163

Ala Ala Trp Asp Asp Ser Leu Asn Gly Trp Val Phe Gly
1               5                   10

```
<210> SEQ ID NO 164
<211> LENGTH: 13
<212> TYPE: PRT
<213> ORGANISM: Homo sapiens

<400> SEQUENCE: 164

Glu Ala Trp Asp Asp Ser Leu Lys Gly Pro Val Phe Gly
1               5                   10

<210> SEQ ID NO 165
<211> LENGTH: 15
<212> TYPE: PRT
<213> ORGANISM: Homo sapiens

<400> SEQUENCE: 165

Cys Thr Gly Ser Ser Ser Asn Ile Gly Ala Gly Tyr Asp Val His
1               5                   10                  15

<210> SEQ ID NO 166
<211> LENGTH: 8
<212> TYPE: PRT
<213> ORGANISM: Homo sapiens

<400> SEQUENCE: 166

Gly Asn Ser Asn Arg Pro Ser Gly
1               5

<210> SEQ ID NO 167
<211> LENGTH: 15
<212> TYPE: PRT
<213> ORGANISM: Homo sapiens

<400> SEQUENCE: 167

Gln Ser Tyr Asp Ser Ser Leu Ser Ala Asp Asn Tyr Val Phe Gly
1               5                   10                  15

<210> SEQ ID NO 168
<211> LENGTH: 14
<212> TYPE: PRT
<213> ORGANISM: Homo sapiens

<400> SEQUENCE: 168

Cys Ser Gly Ser Ser Ser Asn Ile Gly Arg Asn Ile Val Asn
1               5                   10

<210> SEQ ID NO 169
<211> LENGTH: 8
<212> TYPE: PRT
<213> ORGANISM: Homo sapiens

<400> SEQUENCE: 169

Ser Asn Ile Glu Arg Pro Ser Gly
1               5

<210> SEQ ID NO 170
<211> LENGTH: 13
<212> TYPE: PRT
<213> ORGANISM: Homo sapiens

<400> SEQUENCE: 170

Ala Ser Trp Asp Asp Ser Leu Asn Gly Val Leu Phe Gly
1               5                   10
```

```
<210> SEQ ID NO 171
<211> LENGTH: 14
<212> TYPE: PRT
<213> ORGANISM: Homo sapiens

<400> SEQUENCE: 171

Cys Ser Gly Ser Arg Ser Asn Ile Ala Ser Asn Gly Val Gly
1               5                   10

<210> SEQ ID NO 172
<211> LENGTH: 8
<212> TYPE: PRT
<213> ORGANISM: Homo sapiens

<400> SEQUENCE: 172

Lys Asn Asp Gln Arg Pro Ser Gly
1               5

<210> SEQ ID NO 173
<211> LENGTH: 14
<212> TYPE: PRT
<213> ORGANISM: Homo sapiens

<400> SEQUENCE: 173

Ser Ala Trp Asp Asp Ser Leu Asp Gly His Val Val Phe Gly
1               5                   10

<210> SEQ ID NO 174
<211> LENGTH: 13
<212> TYPE: PRT
<213> ORGANISM: Homo sapiens

<400> SEQUENCE: 174

Ala Ala Trp Asp Asp Ser Leu Asn Gly Tyr Val Phe Gly
1               5                   10

<210> SEQ ID NO 175
<211> LENGTH: 14
<212> TYPE: PRT
<213> ORGANISM: Homo sapiens

<400> SEQUENCE: 175

Cys Ser Gly Ser Ser Ser Asn Ile Gly Ser Ser Thr Val Asn
1               5                   10

<210> SEQ ID NO 176
<211> LENGTH: 8
<212> TYPE: PRT
<213> ORGANISM: Homo sapiens

<400> SEQUENCE: 176

Ser Asn Ser Gln Arg Pro Ser Gly
1               5

<210> SEQ ID NO 177
<211> LENGTH: 13
<212> TYPE: PRT
<213> ORGANISM: Homo sapiens

<400> SEQUENCE: 177

Ala Ala Trp Asp Asp Ser Leu Asn Gly Val Val Phe Gly
1               5                   10

<210> SEQ ID NO 178
<211> LENGTH: 14
```

<212> TYPE: PRT
<213> ORGANISM: Homo sapiens

<400> SEQUENCE: 178

Cys Ser Gly Ser Ser Ser Asn Ile Gly Ser Asn Tyr Val Tyr
1               5                   10

<210> SEQ ID NO 179
<211> LENGTH: 8
<212> TYPE: PRT
<213> ORGANISM: Homo sapiens

<400> SEQUENCE: 179

Arg Ser Asn Gln Arg Pro Ser Gly
1               5

<210> SEQ ID NO 180
<211> LENGTH: 14
<212> TYPE: PRT
<213> ORGANISM: Homo sapiens

<400> SEQUENCE: 180

Cys Ser Gly Ser Ser Ser Asn Ile Gly Arg Asn Thr Val Asn
1               5                   10

<210> SEQ ID NO 181
<211> LENGTH: 14
<212> TYPE: PRT
<213> ORGANISM: Homo sapiens

<400> SEQUENCE: 181

Cys Ser Gly Ser Ser Ser Asn Ile Gly Asn Asp Tyr Val Ser
1               5                   10

<210> SEQ ID NO 182
<211> LENGTH: 8
<212> TYPE: PRT
<213> ORGANISM: Homo sapiens

<400> SEQUENCE: 182

Asp Asn Asn Lys Arg Pro Ser Gly
1               5

<210> SEQ ID NO 183
<211> LENGTH: 13
<212> TYPE: PRT
<213> ORGANISM: Homo sapiens

<400> SEQUENCE: 183

Gly Thr Trp Asp Asn Ser Leu Ser Ala Trp Val Phe Gly
1               5                   10

<210> SEQ ID NO 184
<211> LENGTH: 14
<212> TYPE: PRT
<213> ORGANISM: Homo sapiens

<400> SEQUENCE: 184

Cys Ser Gly Ser Ser Ser Asn Ile Gly Ser Asn Ser Val Tyr
1               5                   10

<210> SEQ ID NO 185
<211> LENGTH: 8
<212> TYPE: PRT
<213> ORGANISM: Homo sapiens

<400> SEQUENCE: 185

Asn Asn Asn Gln Arg Pro Ser Gly
1               5

<210> SEQ ID NO 186
<211> LENGTH: 13
<212> TYPE: PRT
<213> ORGANISM: Homo sapiens

<400> SEQUENCE: 186

Ala Thr Trp Asp Asp Ser Leu Ser Gly Trp Val Phe Gly
1               5                   10

<210> SEQ ID NO 187
<211> LENGTH: 8
<212> TYPE: PRT
<213> ORGANISM: Homo sapiens

<400> SEQUENCE: 187

Arg Asn Asn Gln Arg Pro Ser Gly
1               5

<210> SEQ ID NO 188
<211> LENGTH: 13
<212> TYPE: PRT
<213> ORGANISM: Homo sapiens

<400> SEQUENCE: 188

Ala Ala Trp Asp Asp Ser Leu Ser Ala Trp Val Phe Gly
1               5                   10

<210> SEQ ID NO 189
<211> LENGTH: 14
<212> TYPE: PRT
<213> ORGANISM: Homo sapiens

<400> SEQUENCE: 189

Cys Ser Gly Ser Thr Ser Asn Ile Gly Ser Tyr Tyr Val Ser
1               5                   10

<210> SEQ ID NO 190
<211> LENGTH: 8
<212> TYPE: PRT
<213> ORGANISM: Homo sapiens

<400> SEQUENCE: 190

Asp Asn Asn Asn Arg Pro Ser Gly
1               5

<210> SEQ ID NO 191
<211> LENGTH: 13
<212> TYPE: PRT
<213> ORGANISM: Homo sapiens

<400> SEQUENCE: 191

Gly Thr Trp Asp Ser Ser Leu Ser Ala Trp Val Phe Gly
1               5                   10

<210> SEQ ID NO 192
<211> LENGTH: 14
<212> TYPE: PRT
<213> ORGANISM: Homo sapiens

<400> SEQUENCE: 192

Cys Ser Gly Ser Ser Ser Asn Ile Gly Asn Asn Tyr Val Ser
1               5                   10

<210> SEQ ID NO 193
<211> LENGTH: 14
<212> TYPE: PRT
<213> ORGANISM: Homo sapiens

<400> SEQUENCE: 193

Cys Ser Gly Ser Asn Ser Asn Ile Gly Thr Asn Thr Val Thr
1               5                   10

<210> SEQ ID NO 194
<211> LENGTH: 8
<212> TYPE: PRT
<213> ORGANISM: Homo sapiens

<400> SEQUENCE: 194

Ser Asn Phe Glu Arg Pro Ser Gly
1               5

<210> SEQ ID NO 195
<211> LENGTH: 13
<212> TYPE: PRT
<213> ORGANISM: Homo sapiens

<400> SEQUENCE: 195

Ser Ala Trp Asp Asp Ser Phe Asn Gly Pro Val Phe Gly
1               5                   10

<210> SEQ ID NO 196
<211> LENGTH: 14
<212> TYPE: PRT
<213> ORGANISM: Homo sapiens

<400> SEQUENCE: 196

Cys Ser Gly Ser Ser Ser Asn Ile Gly Ser Asn Tyr Val Ser
1               5                   10

<210> SEQ ID NO 197
<211> LENGTH: 13
<212> TYPE: PRT
<213> ORGANISM: Homo sapiens

<400> SEQUENCE: 197

Ala Ala Trp Asp Asp Gly Leu Arg Gly Tyr Val Phe Gly
1               5                   10

<210> SEQ ID NO 198
<211> LENGTH: 11
<212> TYPE: PRT
<213> ORGANISM: Homo sapiens

<400> SEQUENCE: 198

Arg Ala Ser Gln Ser Ile Ser Ser Tyr Leu Asn
1               5                   10

<210> SEQ ID NO 199
<211> LENGTH: 7
<212> TYPE: PRT
<213> ORGANISM: Homo sapiens

<400> SEQUENCE: 199

Ala Ala Ser Ser Leu Gln Ser

```
1               5

<210> SEQ ID NO 200
<211> LENGTH: 8
<212> TYPE: PRT
<213> ORGANISM: Homo sapiens

<400> SEQUENCE: 200

Gln Gln Ser Tyr Ser Thr Pro Thr
1               5

<210> SEQ ID NO 201
<211> LENGTH: 11
<212> TYPE: PRT
<213> ORGANISM: Homo sapiens

<400> SEQUENCE: 201

Arg Ala Ser Gln Gly Ile Ser Asn Tyr Leu Ala
1               5                   10

<210> SEQ ID NO 202
<211> LENGTH: 7
<212> TYPE: PRT
<213> ORGANISM: Homo sapiens

<400> SEQUENCE: 202

Ala Ala Ser Thr Leu Gln Ser
1               5

<210> SEQ ID NO 203
<211> LENGTH: 10
<212> TYPE: PRT
<213> ORGANISM: Homo sapiens

<400> SEQUENCE: 203

Gln Lys Tyr Asn Ser Ala Pro Gly Val Thr
1               5                   10

<210> SEQ ID NO 204
<211> LENGTH: 11
<212> TYPE: PRT
<213> ORGANISM: Homo sapiens

<400> SEQUENCE: 204

Arg Ala Ser Gln Ser Ile Asn Gly Trp Leu Ala
1               5                   10

<210> SEQ ID NO 205
<211> LENGTH: 7
<212> TYPE: PRT
<213> ORGANISM: Homo sapiens

<400> SEQUENCE: 205

Arg Ala Ser Thr Leu Gln Ser
1               5

<210> SEQ ID NO 206
<211> LENGTH: 9
<212> TYPE: PRT
<213> ORGANISM: Homo sapiens

<400> SEQUENCE: 206

Gln Gln Ser Ser Ser Leu Pro Phe Thr
1               5
```

<210> SEQ ID NO 207
<211> LENGTH: 11
<212> TYPE: PRT
<213> ORGANISM: Homo sapiens

<400> SEQUENCE: 207

Arg Ala Ser Gln Gly Ile Ser Tyr Tyr Leu Ala
1               5                   10

<210> SEQ ID NO 208
<211> LENGTH: 7
<212> TYPE: PRT
<213> ORGANISM: Homo sapiens

<400> SEQUENCE: 208

Ala Ala Ser Thr Leu Lys Ser
1               5

<210> SEQ ID NO 209
<211> LENGTH: 9
<212> TYPE: PRT
<213> ORGANISM: Homo sapiens

<400> SEQUENCE: 209

Gln Gln Leu Asn Ser Tyr Pro Leu Thr
1               5

<210> SEQ ID NO 210
<211> LENGTH: 11
<212> TYPE: PRT
<213> ORGANISM: Homo sapiens

<400> SEQUENCE: 210

Gly Gly Asn Asn Ile Gly Ser Lys Ser Val His
1               5                   10

<210> SEQ ID NO 211
<211> LENGTH: 7
<212> TYPE: PRT
<213> ORGANISM: Homo sapiens

<400> SEQUENCE: 211

Asp Asp Ser Asp Arg Pro Ser
1               5

<210> SEQ ID NO 212
<211> LENGTH: 11
<212> TYPE: PRT
<213> ORGANISM: Homo sapiens

<400> SEQUENCE: 212

Gln Val Trp Asp Ser Ser Ser Asp His Pro Val
1               5                   10

<210> SEQ ID NO 213
<211> LENGTH: 11
<212> TYPE: PRT
<213> ORGANISM: Homo sapiens

<400> SEQUENCE: 213

Gln Val Trp Asp Ser Ser Gly Asp His Pro Val
1               5                   10

<210> SEQ ID NO 214

```
<211> LENGTH: 7
<212> TYPE: PRT
<213> ORGANISM: Homo sapiens

<400> SEQUENCE: 214

Tyr Asp Ser Asp Arg Pro Ser
1               5

<210> SEQ ID NO 215
<211> LENGTH: 11
<212> TYPE: PRT
<213> ORGANISM: Homo sapiens

<400> SEQUENCE: 215

Gly Gly Thr Asn Ile Gly Ser Arg Phe Val His
1               5                   10

<210> SEQ ID NO 216
<211> LENGTH: 11
<212> TYPE: PRT
<213> ORGANISM: Homo sapiens

<400> SEQUENCE: 216

Gly Gly Asn Asn Val Glu Ser Lys Ser Val His
1               5                   10

<210> SEQ ID NO 217
<211> LENGTH: 7
<212> TYPE: PRT
<213> ORGANISM: Homo sapiens

<400> SEQUENCE: 217

Tyr Asp Arg Asp Arg Pro Ser
1               5

<210> SEQ ID NO 218
<211> LENGTH: 11
<212> TYPE: PRT
<213> ORGANISM: Homo sapiens

<400> SEQUENCE: 218

Glu Val Trp Asp Ser Gly Ser Asp His Pro Val
1               5                   10

<210> SEQ ID NO 219
<211> LENGTH: 11
<212> TYPE: PRT
<213> ORGANISM: Homo sapiens

<400> SEQUENCE: 219

Gly Gly Lys Asn Ile Gly Ser Lys Ser Val His
1               5                   10

<210> SEQ ID NO 220
<211> LENGTH: 11
<212> TYPE: PRT
<213> ORGANISM: Homo sapiens

<400> SEQUENCE: 220

Gln Val Trp Asp Ser Gly Ser Asp His Tyr Val
1               5                   10

<210> SEQ ID NO 221
<211> LENGTH: 11
<212> TYPE: PRT
```

<213> ORGANISM: Homo sapiens

<400> SEQUENCE: 221

Gln Val Trp Ile Ser Ser Gly Asp Arg Val Ile
1               5                   10

<210> SEQ ID NO 222
<211> LENGTH: 11
<212> TYPE: PRT
<213> ORGANISM: Homo sapiens

<400> SEQUENCE: 222

Gly Gly Asp Asn Ile Gly Ser Gln Gly Val His
1               5                   10

<210> SEQ ID NO 223
<211> LENGTH: 7
<212> TYPE: PRT
<213> ORGANISM: Homo sapiens

<400> SEQUENCE: 223

Tyr Asp Thr Asp Arg Pro Ser
1               5

<210> SEQ ID NO 224
<211> LENGTH: 11
<212> TYPE: PRT
<213> ORGANISM: Homo sapiens

<400> SEQUENCE: 224

Gln Val Trp Gly Ala Ser Ser Asp His Pro Val
1               5                   10

<210> SEQ ID NO 225
<211> LENGTH: 14
<212> TYPE: PRT
<213> ORGANISM: Homo sapiens

<400> SEQUENCE: 225

Thr Gly Thr Ser Ser Asp Val Gly Gly Tyr Asn Tyr Val Ser
1               5                   10

<210> SEQ ID NO 226
<211> LENGTH: 7
<212> TYPE: PRT
<213> ORGANISM: Homo sapiens

<400> SEQUENCE: 226

Asp Val Ser Lys Arg Pro Ser
1               5

<210> SEQ ID NO 227
<211> LENGTH: 10
<212> TYPE: PRT
<213> ORGANISM: Homo sapiens

<400> SEQUENCE: 227

Gly Ile Tyr Thr Tyr Ser Asp Ser Trp Val
1               5                   10

<210> SEQ ID NO 228
<211> LENGTH: 7
<212> TYPE: PRT
<213> ORGANISM: Homo sapiens

<400> SEQUENCE: 228

Asp Val Gly Asn Arg Pro Ser
1               5

<210> SEQ ID NO 229
<211> LENGTH: 10
<212> TYPE: PRT
<213> ORGANISM: Homo sapiens

<400> SEQUENCE: 229

Ser Ser Tyr Thr Ser Ser Ser Thr Arg Val
1               5                   10

<210> SEQ ID NO 230
<211> LENGTH: 14
<212> TYPE: PRT
<213> ORGANISM: Homo sapiens

<400> SEQUENCE: 230

Thr Gly Thr Arg Ser Asp Val Gly Leu Tyr Asn Tyr Val Ala
1               5                   10

<210> SEQ ID NO 231
<211> LENGTH: 7
<212> TYPE: PRT
<213> ORGANISM: Homo sapiens

<400> SEQUENCE: 231

Asp Val Ile Tyr Arg Pro Gly
1               5

<210> SEQ ID NO 232
<211> LENGTH: 10
<212> TYPE: PRT
<213> ORGANISM: Homo sapiens

<400> SEQUENCE: 232

Ser Ser Tyr Thr Asn Thr Gly Thr Val Leu
1               5                   10

<210> SEQ ID NO 233
<211> LENGTH: 14
<212> TYPE: PRT
<213> ORGANISM: Homo sapiens

<400> SEQUENCE: 233

Thr Gly Thr Ser Ser Asp Phe Gly Asp Tyr Asp Tyr Val Ser
1               5                   10

<210> SEQ ID NO 234
<211> LENGTH: 7
<212> TYPE: PRT
<213> ORGANISM: Homo sapiens

<400> SEQUENCE: 234

Asp Val Ser Asp Arg Pro Ser
1               5

<210> SEQ ID NO 235
<211> LENGTH: 12
<212> TYPE: PRT
<213> ORGANISM: Homo sapiens

<400> SEQUENCE: 235

Gln Ser Tyr Asp Ser Ser Leu Ser Gly Ser Gly Val
1               5                   10

<210> SEQ ID NO 236
<211> LENGTH: 330
<212> TYPE: PRT
<213> ORGANISM: Homo sapiens

<400> SEQUENCE: 236

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 237
<211> LENGTH: 106
<212> TYPE: PRT
<213> ORGANISM: Homo sapiens

```
<400> SEQUENCE: 237

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 238
<211> LENGTH: 105
<212> TYPE: PRT
<213> ORGANISM: Homo sapiens

<400> SEQUENCE: 238

Gln Pro Lys Ala Asn Pro Thr Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Gly Ser Pro Val
        35                  40                  45

Lys Ala Gly Val Glu Thr Thr Lys Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105
```